US006858409B1

(12) United States Patent
Thompson et al.

(10) Patent No.: US 6,858,409 B1
(45) Date of Patent: Feb. 22, 2005

(54) NUCLEIC ACIDS ENCODING INTERLEUKIN-1 INHIBITORS AND PROCESSES FOR PREPARING INTERLEUKIN-1 INHIBITORS

(75) Inventors: Robert C. Thompson, Boulder, CO (US); Charles H. Hannum, Sunnyvale, CA (US); Stephen P. Eisenberg, Boulder, CO (US); William P. Arend, Denver, CO (US); Fenneke G. Joslin, Denver, CO (US); Andreas Sommer, Danville, CA (US)

(73) Assignees: Amgen Inc., Thousand Oaks, CA (US); The Regents of the University of Colorado, Boulder, CO (US)

( * ) Notice: Subject to any disclaimer, the term of this patent is extended or adjusted under 35 U.S.C. 154(b) by 0 days.

(21) Appl. No.: 08/482,283

(22) Filed: Jun. 7, 1995

Related U.S. Application Data

(60) Division of application No. 08/319,506, filed on Oct. 6, 1994, now abandoned, which is a continuation of application No. 07/850,675, filed on Mar. 13, 1992, now abandoned, which is a continuation-in-part of application No. 07/822,296, filed on Jan. 17, 1992, now abandoned, and a continuation-in-part of application No. 07/669,862, filed on Mar. 15, 1991, and a continuation-in-part of application No. 07/555,274, filed on Jul. 19, 1990, and a continuation-in-part of application No. 07/506,522, filed on Apr. 6, 1990, now Pat. No. 5,075,222, which is a continuation of application No. 07/266,531, filed on Nov. 3, 1988, now abandoned, which is a continuation-in-part of application No. 07/248,521, filed on Sep. 23, 1988, now abandoned, which is a continuation-in-part of application No. 07/238,713, filed on Aug. 31, 1988, now abandoned, which is a continuation-in-part of application No. 07/199,915, filed on May 27, 1988, now abandoned.

(51) Int. Cl.[7] .............................................. C07H 21/04

(52) U.S. Cl. .................. 435/69.7; 435/69.1; 435/69.9; 435/320.1; 435/356; 435/358; 435/361; 435/252.3; 435/254.11; 435/254.2; 530/412; 536/23.1; 536/23.5

(58) Field of Search .............................. 536/23.1, 23.5; 435/69.1, 69.7, 69.9, 320.1, 356, 358, 361, 252.3, 254.11, 254.2, 325; 530/350, 395, 412

(56) References Cited

U.S. PATENT DOCUMENTS

| | | | |
|---|---|---|---|
| 4,935,343 A | | 6/1990 | Allison et al. |
| 4,956,381 A | | 9/1990 | Bollinger et al. |
| 4,968,607 A | | 11/1990 | Dower et al. |
| 5,041,554 A | | 8/1991 | Parker et al. |
| 5,075,222 A | * | 12/1991 | Hannum et al. ............ 435/69.1 |
| 5,453,490 A | * | 9/1995 | Hageman et al. ........... 530/350 |
| 5,455,330 A | | 10/1995 | Haskill et al. |
| 5,508,262 A | | 4/1996 | Norman, Jr. |
| 5,747,072 A | | 5/1998 | Davidson et al. |
| 5,747,444 A | | 5/1998 | Haskill et al. |
| 5,770,401 A | | 6/1998 | Mullarkey |

FOREIGN PATENT DOCUMENTS

| | | |
|---|---|---|
| EP | 0343684 | * 11/1989 |
| EP | 0 398 817 A1 | 11/1990 |
| WO | WO 88/10299 | 12/1988 |
| WO | WO 89/01946 | 3/1989 |
| WO | WO 89/11540 | 11/1989 |
| WO | WO 91/00742 | 1/1991 |
| WO | WO 91/08285 | 6/1991 |
| WO | WO 91/17184 | 11/1991 |
| WO | WO 91/17249 | 11/1991 |
| WO | WO 92/12724 | 8/1992 |
| WO | WO 92/16221 | 10/1992 |
| WO | WO 93/02692 | 2/1993 |
| WO | WO 93/07863 | 4/1993 |
| WO | WO 93/08304 | 4/1993 |
| WO | WO 93/08819 | 5/1993 |
| WO | WO 93/08820 | 5/1993 |
| WO | WO 93/18783 | 9/1993 |
| WO | WO 93/21946 | 11/1993 |
| WO | WO 93/24134 | 12/1993 |
| WO | WO 94/06457 | 3/1994 |
| WO | WO 94/20517 | 9/1994 |
| WO | WO 94/21235 | 9/1994 |
| WO | WO 94/21275 | 9/1994 |
| WO | WO 95/10298 | 4/1995 |
| WO | WO 95/16353 | 6/1995 |
| WO | WO 95/16706 | 6/1995 |
| WO | WO 96/09323 | 3/1996 |

OTHER PUBLICATIONS

Hannum et al., Interleukin–1 receptor antagonist activity of a human interleukin–1 inhibitor, Nature, 343:336–340, Jan. 1990.*

Eisenberg et al., Primary structure and functional expression from complementary DNA of a human interleukin–1 receptor antagonist, Nature, 343:341–346, Jan. 1990.*

Watson et al., Molecular Biology of the Gene, Fourth Ed., Benjamin/Cummings Publishing:Menlo Park, CA, p. 313, 1987.*

Liao et al., Characterization of a human interleukin 1 inhibitor, J. Immunol., 134(6): 3882–3886, Jun. 1985.*

Rosenstreich et al., A human urine–derived interleukin 1 inhibitor, J. Exp. Med., 168: 1767–1779, Nov. 1988.*

(List continued on next page.)

*Primary Examiner*—Lorraine Spector
(74) *Attorney, Agent, or Firm*—Finnegan, Henderson, Farabow, Garrett & Dunner, LLP

(57) ABSTRACT

Compounds are disclosed having the general formula $R_1-X-R_2$, wherein $R_1$ and $R_2$ are biologically active groups, at least one of which is polypeptidic. X is a non-peptidic polymeric group. $R_1$ and $R_2$ may be the same or different. Preferred $R_1$ and $R_2$ groups are interleukin-1 receptor antagonist, 30 kDa TNF inhibitor, interleukin-2 receptors and CR1 and muteins thereof. Also included are site selectively modified interleukin-1 receptor antagonist and 30 kDa TNF inhibitor.

105 Claims, 19 Drawing Sheets

OTHER PUBLICATIONS

Arend et al., "Effects of Immune Complexes on Production by Human Monocytes of Interleukin 1 or Interleukin 1 Inhibitor", J. Immunol., 134(6):3868–3875 (1985).

Arend et al., "An IL–1 Inhibitor from Human Monocytes", J. Immunol., 143(6):1851–1858 (1989).

Arend et al., "Biological Properties of Recombinant Human Monocyte–derived Interleukin 1 Receptor Antagonist", J. Clin. Invest., 85:1694–1697 (May 1990).

Balavoine et al., "Identification of Interleukin 1–like Activity and Inhibitor(s) in Urine from a Patient with Acute Monoblastic Leukemia", Lymphokine Res., 3(4):233A (Abstract) (1984).

Balavoine et al., "Prostaglandin E2 and Collagenase Production by Fibroblasts and Synovial Cells is Regulated by Urine–derived Human Interleukin 1 and Inhibitor(s)", J. Clin. Invest., 78:1120–1124 (1986).

Barak et al., "Interleukin 1 inhibitory activity secreted by a human myelomonocytic cell line (M20)", Eur. J. Immunol., 16:1449–1452 (1986).

Barak et al., "Interleukin 1 Inhibitor: Characterization of Mechanism of Activity", Lymphokine Res. 7:268 (Abstract No. 1.32) (1988).

Beck et al., "Production of Interleukin 1 and A C1q Induced Interleukin 1 Inhibitor by B–CLL Cells", RES 1987 Annual Meeting (Abstract No. 232).

Bienkowski et al., "Purification and Characterization of Interleukin 1 Receptor Level Antagonist Proteins from THP–1 Cells", J. Biol. Chem., 265(24):14505–14511 (1990).

Billingham et al., "Interleukin–1: Its Relevance to Rheumatoid Arthritis", British J. Rheum., 24 (suppl. 1):25–28 (1985).

Biotechnology Bulletin (1994) Jul. 31, 1994, 13(6):2 (100–199 words).

Bories et al., "Human α 1–Acid Glycoprotein–exposed Macrophages Release Interleukin 1 Inhibitory Activity", Biochem. and Biophys. Res. Comm., 147(2):710–715 (1987).

Bowie et al., "Deciphering the Message in Protein Sequences: Tolerance to Amino Acid Substitutions", Science, 247:1306–1310 (1990).

Brown et al., "Mechanism of Action of a Human Interleukin–1 Inhibitor", J. Leukocyte Biol., 37:688–689 (Abstract) (1985).

Bulletin International d'Informations (Droit et Pharmacie), Sep. 21, 1994, 8/9 p. 89(100–199 words).

Cannon et al., "Circulating Interleukin–1 and Tumor Necrosis Factor in Septic Shock and Experimental Endotoxin Fever", Journal of Infectious Diseases, 161:79–84 (1990).

Carter et al., "Purification, cloning, expression and biological characterization of an interleukin–1 receptor antagonist protein", Nature, 344:633–638 (1990).

Catalano, "Clinical Use of Human Recombinant IL–1 Receptor Antagonist", Keystone Symposium on Cytokines and Cytokine Receptors, Jan. 31–Feb. 7, 1993, p. 55 (Abstract No. E016).

Cominelli et al., "Interleukin–1 in the pathogenesis of and protection from inflammatory bowel disease", Biotherapy, 1(4):369–375 (1989).

Cominelli et al., "Regulation of Eicosanoid Production in Rabbit Colon by Interleukin–1", Gastroenterology, 97(6):1400–1405 (1989).

Cominelli et al., "Interleukin 1 (IL–1) Gene Expression, Synthesis, and Effect of Specific IL–1 Receptor Blockade in Rabbit Immune Complex Colitis", J. Clin. Invest., 86:972–980 (1990).

Conti et al.,"Human Recombinant Interleukin–1 Receptor Antagonist (hrIL–1ra) Enhances the Stimulatory Effect of Interleukin–2 on Natural Killer Cell Activity Against Molt–4 Target Cells", Int. J. Immunopharmac, 14(6):987–993 (1992).

Dinarello, "Interleukin–1 and Interleukin–1 Antagonism", Blood, 77(8):1627–1652 (1991).

Dinarello et al., "Interleukin–1", Digestive Dieseases & Sciences, 33(3):25S–35S (1988).

Dinarello et al., "Interleukins", Ann. Rev. Med., 37:173–178 (1986).

Durum et al., "Interleukin 1: An Immunological Perspective", Ann. Rev. Immunol., 3:263–287 (1985).

Eichacker et al., "The Effects of Human Recombinant Interleukin–1 (IL–1) on Canine Alveolar Neutrophil(N) Number and Lung Function", Critical Care Medicine, Apr. 1989, p. S58 (Abstract).

Ferrara, "The Role of Interleukin 1 (IL–1) and IL–1 Receptor Antagonist in Graft–Versus–Host Disease", Keystone Symposium on Cellular Immunity & the Immuno–therapy of Cancer, Mar. 17–24, 1993, p. 96 (Abstract No. NZ 019).

Furutani et al., "Cloning and characterization of the cDNAs for human and rabbit interleukin–1 precursor", Nucleic Acids Res., 13(16):5869–5882 (1985).

Girardin et al., "Tumor Necrosis Factor and Interleukin–1 in the Serum of Children with Severe Infectious Purpura", New England Journal of Medicine, 319(7):397–400 (1988).

Hall, "Isolation and partial purification of an inhiitor to interleukin 1", Chem. Abstr., 105(17):539, abstract No. 151238W (Diss. Abstr. Int. B, 46(12), pt. 1, 4191 (1986).

Hall, "Isolation and Partial Purification of an Inhibitor to Interleukin I," a dissertation submitted in partial fulfillment of the requirements for the degree of Doctor of Philosophy at Virginia Commonwealth University, VCU, Richmond, VA, pp. 1–218 (Dec. 1985).

Helfman et al., "Identification of clones that encode chicken tropomyosin by direct immunological screening of a cDNA expression library", Proc. Natl. Acad. Sci. USA, 80:31–35 (1983).

Hill et al., "Interleukin 1: A Regulatory Role in Glucocorticoid–Regulated Hepatic Metabolism", J. Immunol., 137(3):858–862 (1986).

Kemp et al., "Inhibition of Interleukin 1 Activity by a Factor in Submandibular Glands of Rats", J. Immunol. 137(7):2245–2251 (1986).

Kimball et al., "Interleukin 1 Activity in Normal Human Urine", J. Immunol., 133(1):256–260 (1984).

Korn et al., "Augmentation of IL 1–Induced Fibroblast PGE2 Production by a Urine–Derived IL 1 Inhibitor", J. Immunol., 138(10):3290–3294 (1987).

Kramer et al., "Comparisons of the Complete Sequences of Two Collagen Genes from *Caenorhabditis elegans*", Cell, 30:599–606 (1982).

Kupper et al., "Hydrocortisone Reduces Both Constitutive and UV–Elicited Release of Epidermal Thymocyte Activating Factor (ETAF) by Cultured Keratinocytes", J. Investigative Dermatology, 87:570–573 (1986).

Liao et al., "Identification of a Specific Interleukin 1 Inhibitor in the Urine of Febrile Patients", J. Exp. Med. 159:126–136 (1984).

Locksley et al., "Release of Interleukin 1 Inhibitory Activity (Contra–IL–1) by Human Monocyte–derived Macrophages Infected with Human Immunodeficiency Virus In Vitro and In Vivo", J. Clin. Invest., 82:2097–2105 (Dec. 1988).

Lomedico et al., "Cloning and expression of murine interleukin–1 cDNA in *Escherichia coli*", Nature, 312:458–462 (1984).

Lotz et al., "Characterization of Interleukin–1 Inhibitors in Rheumatoid Synovial Fluid", Arthritis Rheum., 29:S38 (Abstract No. 162) (1986).

Lotz et al., "Release of Lymphokines After Infection with Epstein Barr Virus In Vitro", J. Immunol., 136(10):3643–3648 (1986).

Maniatis, "Strategies for cDNA Cloning" and "Construction of Genomic Libraries in Bacteriophage λ Vectors" and "Hybridization of Southern Filters", Molecular Cloning, A Laboratory Manual, Cold Springs Harbor Laboratory, CSH, NY, pp. 224–228, 229–246, 270–307, and 387–389 (1982).

Matsudaira, "Sequence from Picomole Quantities of Proteins Electroblotted onto Polyvinylidene Difluoride Membranes", J. Biological Chem., 262(21):10035–10038 (1987).

Mazzei et al., "Purification and Characterization of a 26–kDa Competitive Inhibitor of Interleukin 1," Eur. J. Immunol., 20:683–689 (1990).

Miossec et al., "Production of Both Interleukin–1 (IL–1–Like Activity and IL–1 Inhibitory Factor by Endothelial Cells (EC)", Fed Proc., 44:1262 (Abstract No. 4978) (1985).

Moldawer, "Interleukin–1, TNFa and Their Naturally Occurring Antagonists in Sepsis", Blood Purif., 11:128–133 (1993).

Moonen et al. , "Bioassay for interleukin–1 inhibitors", Chem. Abstr., 107:587 (Abstract 234307K) (1987).

Nishihara et al., "Production of an Interleukin–1 Inhibitor by Cell Line P388D1 Murine Macrophages Stimulated with *Haemophilus actinomycetemcomitans* Lipopolysaccharide", Infection and Immunity, 56(11):2801–2807 (1988).

Ohlsson et al., "Interleukin–1 receptor antagonist reduces mortality from endotoxin shock", Nature:348:550–552 (1990).

Okusawa et al., "Interleukin 1 induces a Shock–like State in Rabbits", J. Clin. Invest., 81:1162–1172 (1988).

Piguet et al., "Interleukin 1 Receptor Antagonist (IL–1ra) Prevents or Cures Pulmonary Fibrosis Elicited in Mice by Bleomycin or Silica", Cytokine, 5(1):57–61 (1993).

Poli et al., "Interleukin 1 induces expression of the human immunodeficiency virus alone and in synergy with interleukin 6 in chronically infected U1 cells: Inhibition of inductive effects by the interleukin 1 receptor antagonist", Proc. Natl. Acad. Sci. USA, 91:108–112 (1994).

Pujol et al., "Interleukin–1 and Osteoarthritis", Life Sciences, 41:1187–1198 (1987).

Relton & Rothwell, "Interleukin–1 Receptor Antagonist Inhibits Ischaemic and Excitotoxic Neuronal Damage in the Rat", Brain Research Bulletin, 29:243–246 (1992).

Roberts et al., "Interleukin–1 and Inhibitor Production by Human Macrophages Exposed to Influenza Virus or Respiratory Syncytial Virus", The Physiologic, Metabolic, and Immunologic Actions of Interleukin–1, Proceeding of a Symposium Held in Ann Arbor, Michigan, Jun. 4–6, 1985, pp. 409–418, Alan R. Liss Inc. publisher (1985).

Roberts et al., "Interleukin 1 and Interleukin 1 Inhibitor Production by Human Macrophages Exposed to Influenza Virus or Respiratory Syncytial Virus", J. Exp. Med., 163:511–519 (1986).

Rodgers et al., "Monocyte–Derived Inhibitor of Interleukin 1 Induced by Human Cytomegalovirus", J. Virol., 55(3):527–532 (1985).

Rolfe et al., "Interleukin–1 Receptor Antagonist Expression in Sarcoidosis", Am. Rev. Respir. Dis., 148:1378–1384 (1993).

Rosenstriech et al., "Studies on a Urine Derived Human Interleukin–1 Inhibitor", The Physiologic, Metabolic, and Immunologic Actions of Interleukin–1, Proceeding of a Symposium Held in Ann Arbor, Michigan, Jun. 4–6, 1985, pp. 419–428.

Rosenstreich et al., "Human interleukin 1 inhibitors", Chem. Abstr., vol. 108, No. 17 (1988), p. 559, abstract No. 148372s; from Lymphokines, 14:63–89 (1987).

Rothwell & Relton, "Involvement of Cytokines in Acute Neurodegeneration in the CNS", Neurosci. Biobehav. Rev., 17:217–227 (1993).

Scala et al., "Accessory Cell Function of Human B Cells", J. Exp. Med., 159:1637–1652 (1984).

Scala et al., "Regulatory Counteraction to Interleukin 1 (IL1) Production and Activity by Inhibitory Cells and Factors", Lymphokine Res., 3:271 (Abstract) (1984).

Scala G., Matsushima K., Oppenheim J.J., "Inhibitory cells and factors that regulate the production and activities of interleukin 1 IL–1", Serono symposia publications from Raven Press, vol. 23, Immunopharmacology, editors, Peter A. Miescher, L. Bolis, M. Ghione. New York, pp. 41–50 (1985).

Schnyder et al., "Human Monocyte or Recombinant Interleukin 1's are Specific for the Secretion of a Metalloproteinase from Chondrocytes", J. Immunol., 138(2):496–503 (1987).

Schwarz et al., "UV–Irradiated Epidermal Cells Produce a Specific Inhibitor of Interleukin 1 Activity", J. Immunol., 138(5):1457–1463 (1987).

Seckinger et al., "Interleukin–1 Inhibitors", 18th Forum in Immunology, Ann. Inst. Pasteur Immunol., 138:486–488 (1987).

Seckinger et al., "A Urine Inhibitor of Interleukin 1 Activity Affects Both Interleukin 1α and 1β But Not Tumor Necrosis Factor α1", J. Immunol., 139(5):1541–1545 (1987).

Seckinger et al., "A Urine Inhibitor of Interleukin 1 Activity that Blocks Ligand Binding", J. Immunol., 139:1546–1549 (1987).

Seckinger et al., "Natural and Recombinant Human IL–1 Receptor Antagonists Block the Effects of IL–1 on Bone Resorption and Prostaglandin Production", J. Immunol., 145(12):4181–4184 (1990).

Shirahama et al., "Kupffer Cells May Autoregulate Interleukin 1 Production by Producing Interleukin 1 Inhibitor and Prostaglandin E2", Scand. J. Immunol., 28:719–725 (1988).

Sissons et al., "A Monocyte Derived Inhibitor of Interleukin 1 Induced by Human Cytomegalovirus", Clin. Res., 33(2):(Abstract No. 610A) (1985).

Sofer, "Chromatographic Removal of Pyrogens", Bio/Technology, Dec.:1035–1038 (1984).

Sofer et al., "Designing an Optimal Chromatographic Purification Scheme for Proteins", BioTechniques, Nov./Dec. 1983, pp. 198–203.

Stimpson et al., "Exacerbation of Arthritis by IL–1 in Rat Joints Previously Injured by Peptidoglycan–Polysaccharide", J. Immunol., 140:2964–2969 (1988).

Suggs et al., "Use of synthetic oligonucleotides as hybridization probes: Isolation of cloned cDNA sequences for human β2–microglubulin", Proc. Natl. Acad. Sci. USA, 78:6613–6617 (1981).

Sullivan et al., "Inhibition of the Inflammatory Action of Interleukin–1 and Tumor Necrosis Factor (Alpha) on Neutrophil Function by Pentoxifylline", Infection & Immunity, 56(7):1722–1729 (1988).

Takahashi et al., "Basal and Clinical Investigation of Urine IL–1 Inhibitor", Hiroshima Univ. Med. J., 35(4):813–842 Dialog Abstract, BIOSIS No. 85016332 (1987) (Japanese with English Abstract).

Tan et al., "Inhibition of Bone Resorption by a Diphosphonate: in vitro Interleukin 1 Studies and Phase 1 Trials in Rheumatoid Arthritis", Australian and New Zealand Rheum Assoc., Abstract on p. 113 (1986).

Thomas et al., "Evaluation of an interleukin–1 receptor antagonist in the rat acetic acid–induced colitis model", Agents & Action, 34:187–190 (1991).

Tiku et al., "Neutrophil Production of an Interleukin–1 Inhibitor", J. Leukocyte Biol., 37:747–748 (Abstract) (1985).

Tiku et al., "Synovial Fibroblast Cell Proliferation Can Be Inhibited by Polymorphonuclear Derived Inhibitor to Interleukin–1", Arthrit. Rheum., 29:S98 (Abstract E34) (1986).

Tiku et al., "Interleukin 1 Production by Human Polymorphonuclear Neutrophils", J. Immunol., 136(10):3677–3685 (1986).

Tiku et al., "Normal Human Neutrophils are a Source of a Specific Interleukin 1 Inhibitor", J. Immunol., 136(10):3686–3692 (1986).

Tracey et al., "Detection of an Inhibitor of Interleukin–1 Activity in Febrile Mouse Serum", J. Leukocyte Biol., 37:750 (top Abstract) (1985).

Tracey et al., "The Use of Murine T–Cell Lines to Evaluate the Effects of Several Pharmacological Agents on Interleukin–1 Activity", J. Leukocyte Biol., 37:750–751 (Abstract) (1985).

Ulich et al., "The Intratracheal Administration of Endotoxin and Cytokines. III. The Interleukin–1 (IL–1) Receptor Antagonist Inhibits Endotoxin– and IL–1–Induced Acute Inflammation", Am. J. Pathology, 138(3):521–524 (1991).

van Hilten et al., "A Report on the International Conference on Inflammation Held in Rome, Oct. 6–11, 1991", DN&P, 5(1):59–62 (1992).

Wakabayashi et al., "A specific receptor antagonist for interleukin 1 prevents *Escherichia coli*–induced shock in rabbits", FASEB J., 5(3):338–343 (1991).

Westley et al., "Newcastle Disease Virus–Infected Splenoytes Express the Proopiomelanocortin Gene", J. Exp. Med., 163:1589–1594 (1986).

Wooley et al., "The Effect of an Interleukin–1 Receptor Antagonist Protein on Type II Collagen–induced Arthritis and Antigen–induced Arthritis in Mice", Arthritis & Rheumatism, 36(9):1305–1314 (1993).

Yost et al., "Inhibition of In Vitro Human Lymphocyte Activation by an Interleukin–1 Inhibitor", J. Allergy Clin. Immunol., 77:230 (Abstract No. 439) (1986).

Ziegler et al., "Treatment of Gram–Negative Bacteremia and Shock with Human Antiserum to a Mutant *Escherichia coli*", New England Journal of Medicine, 307:1225–1230 (1982).

Notice of Opposition to a European Patent (European Patent No. 341273 B1) and Facts And Arguments Supporting The Opposition Against European Patent No. 341273 B1, filed by Amgen Inc., dated Oct. 8, 1997.

Official Communication, and Letter From The Proprietor (Biogen) including Observation Under Article 101(2) EPC (Observations to the Opposition filed by Amgen Inc.), dated Aug. 4, 1998.

Summons To Attend Oral Proceedings Pursuant To Rule 71(1) EPC, including Prelminary Opinion, dated Jul. 11, 2000.

Response To The Official Communication dated Aug. 4, 1998; and the Preliminary Opinion dated Jul. 11, 2000, filed by Amgen, dated Jan. 8, 2001.

Letter to European Patent Office from Amgen, dated Feb. 6, 2001.

Letter to European Patent Office from Biogen, including Observations Of The Patent Proprietor In Response To The Opponent's Letter Dated Jan. 8, 2001, dated Feb. 6, 2001.

Letter to European Patent Office from Amgen, dated Feb. 22, 2001.

Letter to European Patent Office from Biogen, dated Feb. 27, 2001.

Minutes of Oral Proceeding dated Mar. 19, 2001.

Decision Revoking the European Patent (Art. 102(1), (3) EPC), dated May 25, 2001.

Notice that the Patent Proprietor filed an appeal, dated Jul. 25, 2001.

Notice of Appeal pursuant to Article 108 EPC, dated Jul. 12, 2001.

Communication from European Patent Office enclosing a copy of the statement setting out the grounds of appeal, dated Oct. 12, 2001.

Letter to European Patent Office from Biogen, dated Oct. 3, 2001.

Statement Of Grounds Of Appeal, dated Oct. 3, 2001.

Balavoine et al., "Collagense– and $PGE_2$–Stimulating Activity (Interleukin–1–Like) and Inhibitor in Urine from a Patient with Monocytic Leukemia", The Physiologic, Metabolic, and Immunologic Actions of Interleukin–1, pp. 429–436 (1985).

Dayer et al., "Collagenase–and PGE2– Stimulating Activity (Interleukin–1–Like) and Inhibitors(s) in Human Urine", J. Leukocyte Biology, 37, p. 693 (Jun. 1985).

Gearing et al., "A simple sensitive bioassay for interleukin–1 which is unresponsive to $10^3$ U/ml of interleukin–1", J. Immunol. Methods, 99:7–11 (1987).

Urdal et al., "Affinity purification and chemical analysis of the interleukin–1 receptor", J. Biol. Chem., 263:2870–2877 (1988).

* cited by examiner

```
                                        10                          20
Asp Ser Val Cys Pro Gln Gly Lys Tyr Ile His Pro Gln Asn Asn Ser Ile Cys Cys Thr
                                        30                          40
Lys Cys His Lys Gly Thr Tyr Leu Tyr Asn Asp Cys Pro Gly Pro Gly Gln Asp Thr Asp
                                        50                          60
Cys Arg Glu Cys Glu Ser Gly Ser Phe Thr Ala Ser Glu Asn His Leu Arg His Cys Leu
                                        70                          80
Ser Cys Ser Lys Cys Arg Lys Glu Met Gly Gln Val Glu Ile Ser Ser Cys Thr Val Asp
                                        90                         100
Arg Asp Thr Val Cys Gly Cys Arg Lys Asn Gln Tyr Arg His Tyr Trp Ser Glu Asn Leu
                                       110                         120
Phe Gln Cys Phe Asn Cys Ser Leu Cys Leu Asn Gly Thr Val His Leu Ser Cys Gln Glu
                                       130                         140
Lys Gln Asn Thr Val Cys Thr Cys His Ala Gly Phe Phe Leu Arg Glu Asn Glu Cys Val
                                       150                         160
Ser Cys Ser Asn Cys Lys Lys Ser Leu Glu Cys Thr Lys Leu Cys Leu Pro Gln Ile Glu

161
Asn
```

FIG.2

NUCLEIC ACIDS ENCODING INTERLEUKIN-1 INHIBITORS AND PROCESSES FOR PREPARING INTERLEUKIN-1 INHIBITORS

CROSS REFERENCE TO RELATED APPLICATIONS

This application is a divisional of U.S. Application No. 08/319,506, filed Oct. 6, 1994, now abandoned, which is a continuation of U.S. Application No. 07/850,675, filed Mar. 13, 1992, now abandoned, which is a continuation-in-part of (1) U.S. patent application Ser. No. 07/822,296, filed Jan. 17, 1992, now abandoned, entitled Method for Treating Tumor Necrosis Factor Mediated Diseases; (2) U.S. patent application Ser. No. 07/669,862, filed Mar. 15, 1991 entitled Site Specific Pegylation of Polypeptides, which is a continuation-in-part of U.S. patent application Ser. No. 07/506,522, filed Apr. 6, 1990 now U.S. Pat. No. 5,075,222 entitled Interleukin-1 Inhibitors, which is a continuation of U.S. patent application Ser. No. 07/266,531, filed Nov. 3, 1988, now abandoned which is a continuation-in-part of U.S. patent application Ser. No. 07/248,521, filed Sep. 23, 1988, now abandoned which is a continuation-in-part of U.S. patent application Ser. No. 07/238,713, filed Aug. 31, 1988, now abandoned which is a continuation-in-part of U.S. patent application Ser. No. 07/199,915, filed May 27, 1988; now abandoned and (3) U.S. patent application Ser. No. 07/555,274 filed Jul. 19, 1990 entitled Tumor Necrosis Factor (TNF) Inhibitor and Method for Obtaining Same.

FIELD OF THE INVENTION

This invention relates to polypeptides that have been covalently bonded to long chain polymers such as methoxy polyethylene glycol. This invention also describes methods and reagents for the reaction of activated polymer molecules with various biologically-important polypeptides.

BACKGROUND OF THE INVENTION

Many proteins that have been identified and isolated from human and animal sources have been found to show promising medicinal or therapeutic potential. Great strides have been made in the methods for identifying and characterizing such proteins, in addition to methods for producing such proteins in relatively pure forms and relatively large quantities. As the development process advances in relation to the utilization of such potentially valuable materials many obstacles have arisen in formulating these compounds for use in clinical models.

For example, many such proteins have been found to have an extremely short half life in the blood serum. For the most part, proteins are cleared from the serum through the kidneys. The systematic introduction of relatively large quantities of proteins, particularly those foreign to the human system, can give rise to immunogenic reactions that, among other problems, may lead to rapid removal of the protein from the body through formation of immune complexes. For other proteins, solubility and aggregation problems have also hindered the optimal formulation of the protein.

One of the most promising techniques for addressing these problems has been covalently bonding one or more inert polymer chains to the polypeptide of interest. The most commonly used polymer is polyethylene glycol (PEG), or monomethoxyl polyethylene glycol (mPEG). See, for example, Davis et al., *Biomedical Polymers: Polymeric Materials and Pharmaceuticals for Biomedical Use*, pp. 441–451 (1980). PEG is ideal for these purposes due to its proven non-toxic properties. Other researchers have utilized polyoxyethylated glycerol (POG) for similar purposes. Knauf et al., *J. of Biolog. Chem.* vol. 263, pg. 15064 (1988).

Numerous results have been described whereby the covalent modification of proteins with polyethylene glycols ("pegylation") have resulted in the addition of desirable characteristics to the protein. For example, the pegylation of IL-2 has been shown to decrease the clearance of IL-2 while not significantly affecting the activity of the cytokine. The decreased clearance leads to an increased efficiency over the non-pegylated material. Katre et al., *Proc. Natl. Acad. Sci. U.S.A.* vol. 84, pg. 1487 (1987).

Increasing the half-life of Superoxide Dismutase (SOD) in blood serum has been a critical barrier for the use of SOD for the treatment of various symptoms. A number of studies have shown that the pegylation of SOD will give rise to a decreased clearance rate. See, for example, Conforti et al., *Pharm. Research Commun.* vol. 19, pg. 287 (1987).

Aggregation of Immunoglobulin G (IgG) has been postulated as a factor that leads to serious side effects to patients that are intravenously administered IgG. It has been shown that the pegylation of IgG reduces the aggregation of the proteins to prevent this problem. Suzuki et al., *Biochem, Biopys. Acta* vol. 788, pg. 248 (1984).

The ability of pegylation techniques to affect protein immunogenicity has also been shown. Abuchouski and coworkers have studied the immunogenicity and circulating life of pegylated Bovine Liver Catalase. Abuchowski et al., *J. Biol. Chem.* vol. 252, pg. 3582 (1977).

The addition of PEG groups to these various proteins decreases clearance due to the increase in molecular size of the pegylated protein. Up to a certain size, the rate of glomerular filtration of proteins is inversely proportional to the size of the protein. The ability of pegylation to decrease clearance, therefore, is generally not a function of how many PEG groups are attached to the protein, but the overall molecular weight of the altered protien. This has been borne out by clearance studies that varied both the size of the PEG side chains and the number of PEG units bonded to IL-2. Katre, supra.

The various studies of pegylated proteins in relation to clearance, immunogenicity, aggregation and physical properties all suggest that the PEG forms a flexible, hydrophilic shell around the protein. The PEG chains become highly hydrated and give the pegylated proteins a higher apparent molecular weight than would be predicted, and act to shield charges on the protein.

Because of the many promising results that have been seen in this field, a catalogue of procedures for the attachment of PEG units to polypeptides has been developed. The key element in these procedures is the "activation" of the terminal—OH group of the polyethylene glycol. Such activation is necessary in order to create a bond between the PEG group and the polypeptide. The vast majority of coupling procedures activate the PEG moiety in order to react with free primary amino groups of the polypeptides. Most of these free amines are found in the lysine amino acid residues.

In general practice, multiple PEG moieties are attached to the proteins. For example, in U.S. Pat. No. 4,179,337 of Davis et al., it was found that to suppress immunogenicity it is desireable to use between 15 and 50 moles of polymer per mole of polypeptide.

Because multiple PEG chains are generally bonded to each polypeptide, and because there are typically a large number of lysine residues in each protein, there has been little effort to pegylate proteins to yield homogenous reaction products. See, Goodson et al. *Biotechnology*, vol. 8, pg. 343 (1990); U.S. Pat. No. 4,904,584 of Shaw. This lack of reaction specifity gives rise to a number of complications. Among these, are that pegylation often results in a significant loss of activity of the protein. Presumably, attachment to a critical lysine residue could alter the active site of the protein rendering it inactive.

It has been shown in at least one system, that pegylation can lead to sterically hindered active sites. In other words, relatively small substrates may approach the protein, while the activity of proteins that react with larger substrates can be dramatically effected by random pegylation. Davis et al. supra. The site selective pegylation of such proteins could lead to modified materials that gain the desireable attributes of pegylation without the loss of activity. In addition, if the pegylated protein is intended for therapeutic use, the multiple species mixture that results from the use of non-specific pegylation leads to difficulties in the preparation of a product with reproducible and characterizable properties. This makes it extremely difficult to evaluate therapeutics and to establish efficacy and dosing information.

In certain cases, it has been found that the administration of multimeric complexes that contain more than one biologically active polypeptide or drug can lead to synergistic benefits. For example, a complex containing two identical binding polypeptides may have substantially increased affinity to the ligand or active site that it binds relative to the monomeric polypeptide. For this reason, multimeric complexes of proteins can be desirable in order to increase affinity of the protein to its ligand in addition to increasing the molecular weight of the complex.

Proteins frequently achieve their biological effects through interaction with other proteins. Where a simple complex of two proteins is sufficient to achieve the biological effect it has proved possible to mimic the physiological effects of endogenous proteins by administering exogenous proteins. However, where the biological effect requires the assembly of a complex containing more than two proteins it is more difficult to mimic the function of the endogenous proteins with recombinantly produced exogenous equivalents because the higher order complexes are frequently unstable. In such cases it may be advantageous to use crosslinked species containing two of the components of the complex to simulate the biologically-active complex.

Subsequent to the invention described herein, at least three research groups have described the production of crosslinked proteins, where the extracellular portions of one of the TNF receptors is attached to the heavy chain of human or mouse IgG, which are then crosslinked through disulfide bonds. Peppel et al., *J. Exp. Med.* vol. 174, pg. 1483 (1991); Ashkenazi et al., *Proc. Natl. Acad. Sci. USA* vol. 88, pg. 10535 (1991); and Loetscher et al., *J. Biol, Chem.* vol. 266, pg. 18324 (1991). In each case, the proteins were expressed in animal cell expression systems, and were found to be substantially more effective at inhibiting TNF than the monomeric soluble receptor alone. Similar procedures have also been used for producing similar crosslinked proteins of the CD4 protein, (Byrn at al., *Nature (London)* vol. 344, pg. 667 (1990)) the CR1 protein, (Kalli et al., *J. Exp. Med.* vol. 174, pg. 1451 (1991); Hebell et al., WO 91/16437 (1991)) and the CR2 protein. (Hebell et al., *Science*, vol. 254, pg. 102 (1991)).

These crosslinked proteins—constructed of two polypeptide units and a portion of the IgG antibody—have been shown to have promise as therapeutic agents. The crosslinked proteins have an increased molecular weight, which acts to decrease the rate of clearance of the complex from the body, in addition to the apparent enhancement of the affinity of the proteins to their ligand. However, the proteins crosslinked in this manner have so far only been prepared by expression in animal cell expression systems by the expression of fused genes. This has been required in order to have the IgG portion of the protein properly folded after expression. In addition, the fixed heavy chain portion of the IgG antibody that serves as the spacer or linker between the polypeptide units does not allow for the ability to vary the length, size or geometry of the spacer. Given the apparent synergistic effect achieved by the dimeric proteins, it is likely that by varying the spatial orientation of the polypeptides the synergistic benefit may be optimized. And finally, the crosslinked proteins may be antigenic and/or have decreased solubility. The heavy chain of antibodies is not biologically inert.

Other dimeric or "bivalent" complexes have been described. One such group of dimeric compounds has been labeled hirulogs. These compounds are comprised of very short polypeptide units that are linked by a short polyglycine spacer or linker. One of the polypeptide units is a thrombin inhibitor—a 5 amino acid sequence taken from the 65 amino acid protein Hirudin—and the other is an anion-binding exocite (ABE) recognition inhibitor. See, Maragonore et al., *Biochemistry*, vol. 29, pg. 7085 (1990); Bourdon et al., *FEBS* vol. 294, pg. 163 (1991).

C-reactive protein (CRP) is an acute phase serum protein composed of five identical 23 kDa subunits. CRP can induce reactions of precipitation and agglutination and can also react with Clg to activate the classical complement pathway. Cross linked oligomers of CRP have been formed using bis (sulphosuccinimidyl) suberate or 3,3'-dithio (sulphosuccinimidylpropionate) as cross-linking agents. Jiang et al., *Immunology* vol. 74, pg. 725 (1991).

The formation of dimeric or bivalent ligands for targeting opoid receptors has also been investigated. Non-peptidic β-naltrexamine or oxymorphamine pharmacophores have been connected by short ethylene oxide or glycine spacers. Erez et al., *J. Med. Chem.* vol. 25, pg. 847 (1982); Portoghese et al., *J. Med. Chem.* vol. 29, pg. 1855 (1986). Tetrapeptide enkephalins linked by short methylene bridges have also been designed to target opoid receptors, and have been shown to have a greater selectivity and affinity for the delta receptor than the original delta ligand. Shimohigashi et al., *Nature* vol. 197, pg. 333 (1982).

The cell surface glycoprotein CD4 has also been produced in multimeric forms through a sugar-based cross-linking strategy. The cross-linking agent utilized was bismaleimidohexane (BMH). Chen et al., *J. Biol. Chem.* vol 266, pg. 18237 (1991).

Lymphocyte function-associated antigen-3 (LFA-3) is a widely distributed cell surface glycoprotein that is a ligand for the T lymphocyte CD2. LFA-3 with its associated lipids forms protein micelles of eight monomers which increased their ability to interact with cells with CD2 on their surface. Dustin et al., *J. Exp. Med.*, vol. 169, pg. 503 (1989).

In a somewhat related technology, one group has studied the inhibitory effect of a synthetic polypeptide that is comprised of a repeating pentapeptidyl unit. The polymer was synthesized by the polymerization procedure with diphenyl phosphoryl azide to a size of about 10,000 daltons. The polymerized pentapeptide is one of the essential structures in several biological responses. Morata et al., Inst. *J. Biol. Macromol.* vol. 11, pg. 97 (1989).

A further obstacle in developing effective exogenous proteins to augment or compete with endogenous substances is that exogenous proteins must be administered systemically rather than being localized in the appropriate place. This can lead to lower efficacy and to increased side effects. Several groups have reported targeting bioactive proteins to the appropriate sites by linking them to other proteins that naturally home on those sites. Often such linkages are made through gene fusions between the active and the targeting proteins.

Polyethylene glycol spacer or linker units have been used to create antibody targeted superantigens after the date of the instant invention. A monoclonal antibody reactive to colon carcinoma cells was attached to the bacterial superantigen staphylococcal enterotoxin. Rather than being designed to exploit the benefits associated with the other bivalent complexes (e.g., higher molecular weight; synergistic effects of bivalency) these complexes are designed to target superantigens to specific locations. The pegylation process described to form these targeted superantigens creates a complex containing a large mixture of materials. The coupling of the antibody and the superantigen was accomplished by the use of N-succin-imidyl 3-(2-pyridyldithio) proprionate and a 24-atom-long PEG-based hydrophilic space. According to this procedure 7 to 18 spacers were attached to each antibody unit and one or two lysines on each of the super antigens were reacted. Dohlsten et al., *Proc. Natl. Acad. Sci. USA* vol. 88, pg. 9287 (October, 1991). Using this procedure it would be impossible to isolate a single species in order to optimize the product or process.

Two groups of proteinaceous materials having significant applications for the treatment of a wide variety of medical indications are Tumor Necrosis Factor (TNF) inhibitors and Interleukin-1 receptor antagonists (Il-1ra). These materials have been shown to have beneficial effects in the treatment of TNF and IL-1 mediated diseases respectively. Among the indications that have been identified as being either TNF mediated or IL-1 mediated, are Adult Respiratory Distress Syndrome, Pulmonary Fibrosis, Rheumatoid Arthritis, Inflammatory Bowel Disease and Septic Shock.

Copending U.S. patent application Ser. No. 07/555,274, filed Jul. 19, 1990, specifically incorporated herein by reference, describes a class of naturally occurring proteinaceous TNF inhibitors and a method for manufacturing a substantial quantity of the same with a high degree of purity. In particular, the aforementioned application describes in detail two subsets of TNF inhibitors referred to as 30 kDa TNF inhibitor and 40 kDa TNF inhibitor. In addition to the full-length 40 kDa TNF inhibitor protein, two truncated, yet biologically-active, forms of the 40 kDa TNF inhibitor have also been produced. These proteins, in which 51 and 53 carboxyl termini amino acids have been removed from the full-length protein, are referred to respectively as 40 kDa TNF inhibitor $\Delta$51 and 40 kDa TNF inhibitor $\Delta$53.

Copending U.S. patent application Ser. No. 07/506,522, filed Apr. 6, 1990, specifically incorporated herein by reference, describes a preferred class of naturally occurring, proteinaceous Il-1 inhibitors and a method for manufacturing a substantial quantity of the same with a high degree of purity. In particular, the application describes in detail three such interleukin-1 inhibitors which are interleukin-1 receptor antagonists (IL-1ra's), namely, IL-1ra$\alpha$, IL-1ra$\beta$, and Il-1rax.

Two additional classes of materials that are potentially useful for the treatment of a variety of medical indications are interleukin-2 inhibitors and complement inhibitors. Potential inhibitors of interleukin-2 include interleukin-2 receptors, the extracellular portion of interleukin-2 receptors, interleukin-2 receptor antagonists, antibodies that recognize interleukin-2, and fragments of any of such species that contain the IL-2 binding function. Potential inhibitors of the complement system include the receptor CR1, the extracellular portion of CR1, and the fragment of CR1 that contains the complement binding function.

Interleukin-2 receptor has been described and methods for its isolation have been disclosed in U.S. Pat. No. 4,578,335 of Urdal et al. and U.S. Pat. No. 4,816,565 of Honjo et al. The gene encoding Interleukin-2 receptor and methods for its recombinant production have also been disclosed. European Patent Application No. 89104023.0 of Taniguchi et al.; European Patent Application No. 90104246.6 of Taniguchi et al. See also, Honjo et al., *Nature* vol. 311, pg. 631 (1984); Taniguchi et al., *Science* vol. 244, pg. 551 (1989).

It could be assumed that to some extent the soluble extracellular domain of either interleukin-2 receptor will act as an inhibitor to the action of the cytokine interleukin-2. Interleukin-2 is one of the best characterized cytokines, known to play a pivotal role in the antigen-specific clonal proliferation of T lymphocytes. Interleukin-2 has also been shown to act on a variety of other cells in the immune system.

There are three discrete forms of the interleukin-2 receptor, comprised of two distinct receptor molecules designated either as IL-2r$\alpha$ and IL2r$\beta$.

The highest affinity IL-2 receptor is composed of two distinct IL-2 receptors. Both of these receptors have been cloned and characterized. The low affinity IL-2 receptor (IL-2r$\alpha$) was cloned in 1984 and has been well characterized. Nikaido et al., *Nature* vol. 311, pg. 631 (1984). The extracellular domain of the molecule has a molecular weight of 24,825 and has two N-linked glycosylation sites. The molecule contains 11 cysteines, 10 of which are involved in intramolecular disulfide bonds. The putative IL-2 binding domains on the molecule have been mapped both by mutagenesis and epitope mapping.

The intermediate affinity IL-2 receptor (Il-2r$\beta$) was cloned in 1989 and has not been as completely characterized as IL-2r$\alpha$. Hatakayama et al., *Science* vol. 244, pg. 551 (1989). The extracellular domain of IL-2r$\beta$ has a molecular weight of 24,693. The molecule contains 8 cysteines and 4 N-linked glycosylation sites. The disulfide bonding in the molecule is unknown. IL-2r$\beta$ has a cytoplasmic domain of 286 amino acids.

The disassociation constants (Kd's) for the IL-2 receptors have been determined. They are $10^{-8}$M for IL-2r$\alpha$, $10^{-9}$M for IL-2r$\beta$ and $10^{-11}$M for the high affinity receptor which consists of a complex of IL-2r$\alpha$, IL-2r$\beta$ and IL-2. Current models indicate that the formation of the high affinity complex is formed first by IL-2 binding to IL-2r$\alpha$ and then to IL-2r$\beta$. Ogura et al., *Mol. Biol. Med*, vol. 5, pg. 123 (1988).

An inhibitor of IL-2 may be valuable in the prevention of transplant rejection as well as autoimmune disorders. Currently, a monoclonal antibody against IL-2r$\alpha$ that prevents IL-2 binding is being tested in human renal transplantation. Hiesse et al., *La Presse Mediocle* vol. 20, pg. 2036 (1991). In a study of 15 patients, the antibody, in combination with immunosuppressants, has been shown to be as effective in preventing allograft rejection as a control group getting higher doses of immunosuppressants. High levels of circulating soluble IL-2r$\alpha$ have been detected in a number of diseases, some infections, as well as transplantation and rejection. This suggests involvement of IL-2 in these diseases.

CR1 is a protein also referred to as the C3b/C4b receptor. CR1 is present on erythrocytes and a variety of other cell types, and specifically binds C3b, C4b, and iC3b. CR1 can also inhibit the classical and alternate pathway C3/ C5 convertases and act as a cofactor for the cleavage of C3b and C4b by factor 1. Fearon et al., *Proc. Natl. Acad. Sci. USA* vol. 75, pg. 5867 (1979). CR1 is a glycoprotein composed of a single polypeptide chain, and there are four allotypic forms. It is known that CR1 contains repetitive coding sequences, and this fact is used to explain the existence of multiple allotypes. Krickstein et al. *Complement* vol. 2, pg. 44 (Abst.) (1995).

The diminished expression of CR1 on erythocytes has been associated with systemic lupus erythematosus and CR1 number has also been found to correlate inversely with serum level of immune complexes. The CR1 protein, the CR1 gene and methods for the production of CR1 are described in WO 91/05047 and WO 89/09220 of Fearon et al. As described above, dimeric species containing CR1 and portions of an antibody have also been disclosed. WO 91/16437 of Hebell et al.

SUMMARY OF THE INVENTION

This invention relates to a method for modifying polypeptides and the resulting modified polypeptides.

This invention includes substantially purified compounds comprised of the formula $R_1—X—R_2$ wherein $R_1$ and $R_2$ are biologically active groups and X is a non-peptidic polymeric spacer. $R_1$ and $R_2$ may be the same or different groups, and at least one of the $R_1$ and $R_2$ is polypeptidic. In the preferred embodiments, $R_1$ and $R_2$ are selected from the group consisting of interleukin-1 receptor antagonist; 30 kDa tumor necrosis factor inhibitor; interleukin-2 receptor and CR1, and X is selected from the group consisting of polyethylene glycol, polyoxyethylated glycerol, dextran, colonic acids, poly β-amino acids and carbohydrate polymers. Also included are pharmaceutical compositions comprised of such substantially purified compounds in a pharmaceutically acceptable carrier. Further included are methods of treating patients in need thereof with such pharmaceutical compositions. The compounds of the formula $R_1—X—R_2$, as depicted in FIG. 19, are referred to as "dumbbells".

This invention also includes a method for the preparation of substantially purified therapeutically valuable compounds comprised of the formula $R_1—X—R_2$ comprising reacting a non-peptidic polymeric group having at least two reactive groups capable of forming covalent bonds with the biologically active group R; and isolating said compound.

In an alternate embodiment, this invention includes a method for the preparation of substantially purified therapeutically valuable compounds, comprised of the formula $R_1—X—R_2$, wherein $R_1$ and $R_2$ are different, comprised of: reacting a non-peptidic polymeric group capable of forming covalent bonds when reacted with the biologically active group $R_1$ to form a complex $R_1—X$; reacting complex $R_1—X$ with the biologically active group $R_2$ to form said compound; and isolating and purifying said compound.

In one embodiment, this invention relates to the site-specific pegylation of TNF inhibitor and IL-1 inhibitor proteins.

In order to maintain site-specifity of pegylation, pegylating reagents are selected that will react almost exclusively with the free —SH groups of cysteine residues of the polypeptides. An example of a pegylation reagent that covalently binds almost exclusively to the —SH groups of cysteine is 0-(2-maleimido ethyl)-0' methlypolyethylene glycol.

Site specific pegylation may be done at either naturally occurring "free" cysteine residues of a given polypeptide, or at free cysteines contained on muteins of the naturally-occurring polypeptides. Cysteines may either be added to or inserted into the amino acid sequence of the naturally occurring polypeptide, or substituted for other amino acid residues at selected locations.

In one embodiment of this invention, the polypeptides that are to be pegylated are produced via recombinant DNA technology from a bacterial host cell. In most cases the bacterially expressed polypeptide must be refolded to obtain biological activity prior to the pegylation step. In certain applications of this invention, the native polypeptide does not contain any free cysteine residues, but an altered polypeptide is produced to contain at least one free cysteine in the biologically active polypeptide. According to this method, the refolding of the bacterially expressed polypeptide is facilitated by the addition, in turn, of a sulfhydryl containing compound such as cysteine and a disulfide containing compound such as cystine. After refolding and purification, the polypeptide is treated with a limited amount of a mild reducing agent such as dithiothreitol ("DTT") to regenerate the sulfhydryl group of the novel cysteine residue of the altered polypeptide. Following dialysis under conditions designed to prevent oxidation, the polypeptide may be reacted with a cysteine specific pegylation agent to site specifically form a covalently modified polypeptide.

Preferred pegylated polypeptides of the present invention are site-specifically pegylated TNF-inhibitors and IL-1 inhibitors. More specifically, this invention describes pegylated 30 kDa TNF inhibitor and pegylated IL-1 receptor antagonist. Most preferred pegylated TNF inhibitors include 30 kDa TNF inhibitor wherein the asparagine amino acid residue at position 105 of the native human protein is changed to cysteine using in vitro mutagenesis and pegylation has occurred at the free cysteine at position 105. Other pegylated derivatives of mutated 30 kDa TNF inhibitors include mutations where cysteine has been added at positions 1, 14, 111 and 161. In addition to the singly pegylated muteins, any and all combinations of the various mutations may be included within a single mutein to create altered 30 kDa TNF with more than one free cysteine residue capable of being pegylated.

The most preferred pegylated IL-1ra includes native or naturally occurring IL-1ra, which includes four free cysteines. Mono pegylation of the native XL-1ra yields site-specific pegylation at cysteine position 116. Other pegylated derivatives of mutated IL-1ra include muteins having cysteine added at the amino terminus of the polypeptide, cysteine added at positions 6, 8, 9, 84, or 141, and the replacement of the cysteine at position 116 with serine. In addition to the singly pegylated muteins, any and all combinations of the various mutations may be included to create altered IL-1ra with more than one free cysteine capable of being pegylated.

Other aspects and advantages of the present invention will be apparent upon consideration of the following detailed description of the invention, including illustrative examples of the practice of the invention.

BRIEF DESCRIPTION OF THE DRAWINGS

FIG. 1 depicts the amino acid sequence of native IL-1ra.

FIG. 2 depicts the amino acid sequence of native 30 kDa TNF inhibitor.

IL-1ra. Lanes 2, 3, 5 and 6 contain pegylation reaction mixes. Lanes 1 and 4 are the unmodified proteins:.

Lane 1-IL-1ra

Lane 2-mPEG*$_{5000}$ IL-1ra

Lane 3-mPEG*$_{8500}$ IL-1ra

Lane 4-c84s116 IL-1ra

Lane 5-mPEG*$_{5000}$ c84s116 IL-1ra

Lane 6-mPEG*$_{8500}$ c84s116 IL-1ra

Figure 4B:
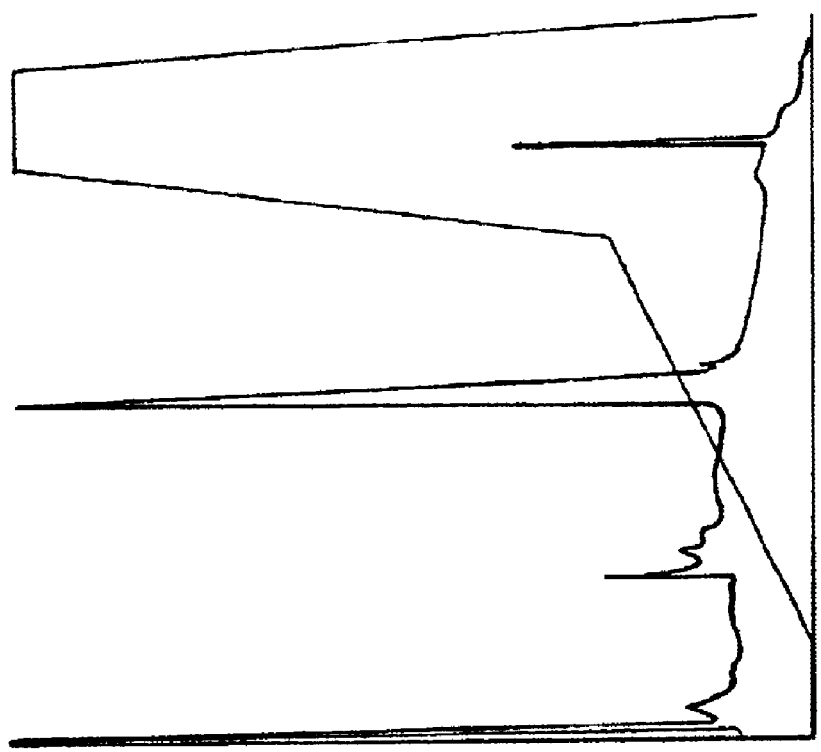
Figure 4A:
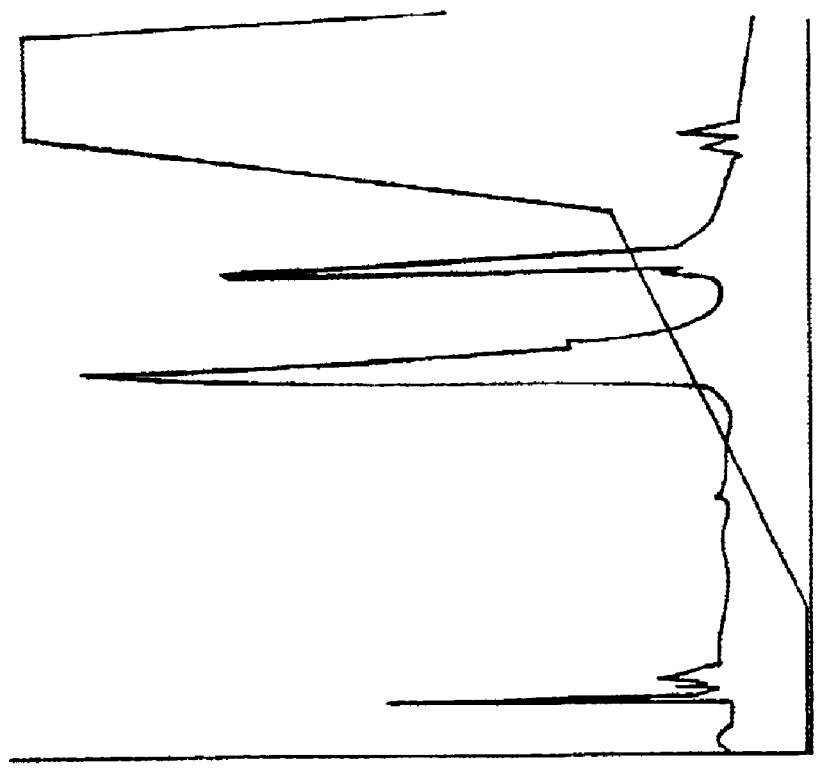

FIG. 4 depicts the mono S ion exchange chromatography of: FIG. 4A; Chromatogram A, the pegylation reaction mixture of mPEG$_{5000}$ IL-1ra, peak 1 is the modified and peak 2 is the unmodified IL-1ra; and FIG. 14B; Chromatogram B, shows the purified mPEG$_{5000}$ IL 1-ra.

Figure 5:
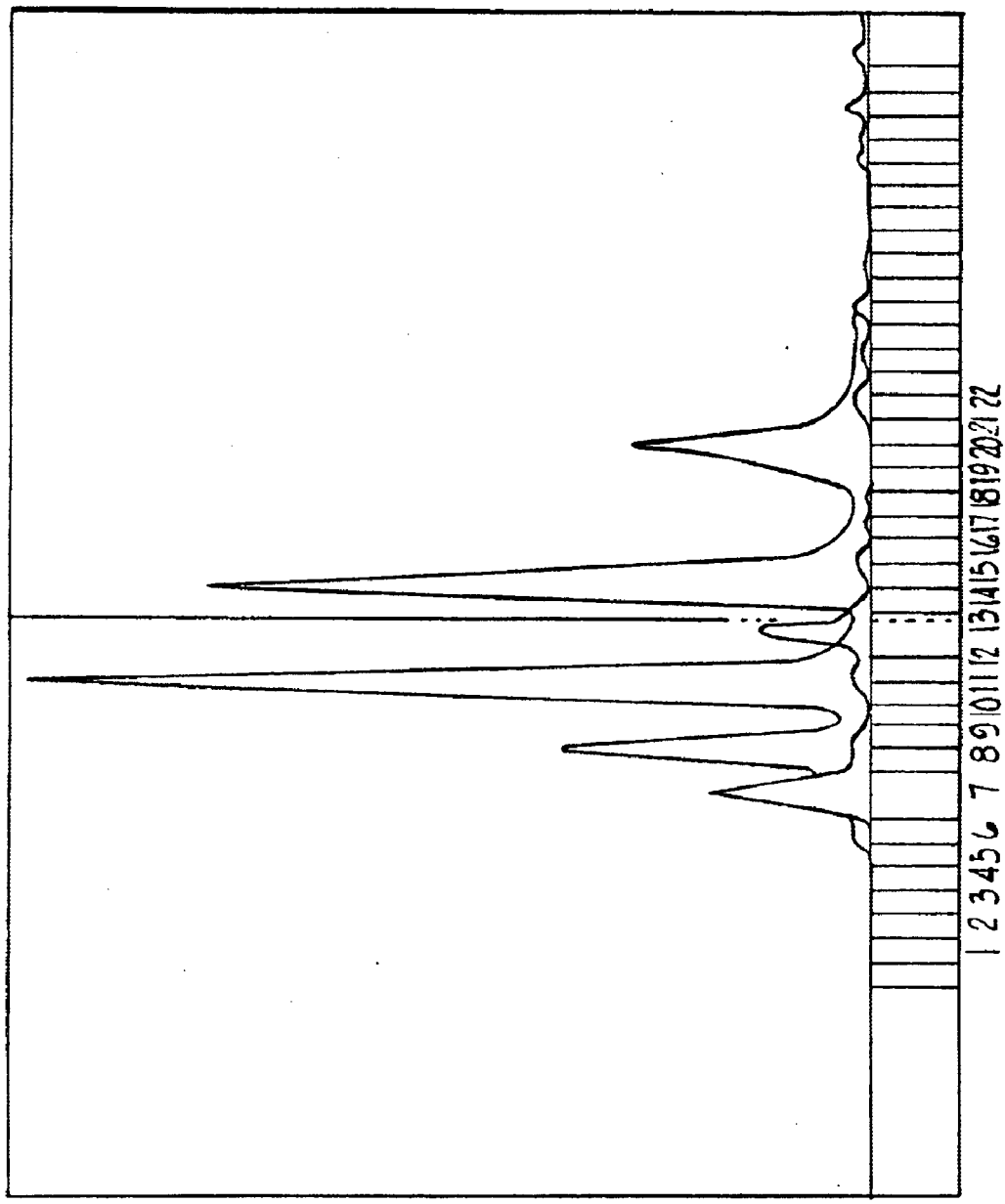

FIG. 5 depicts a size exclusion chromatogram showing the elution profile of several size standards, and mPEG$_{8500}$*IL-1ra (fraction 7) and Il-1ra (fraction 13).

Figure 6:
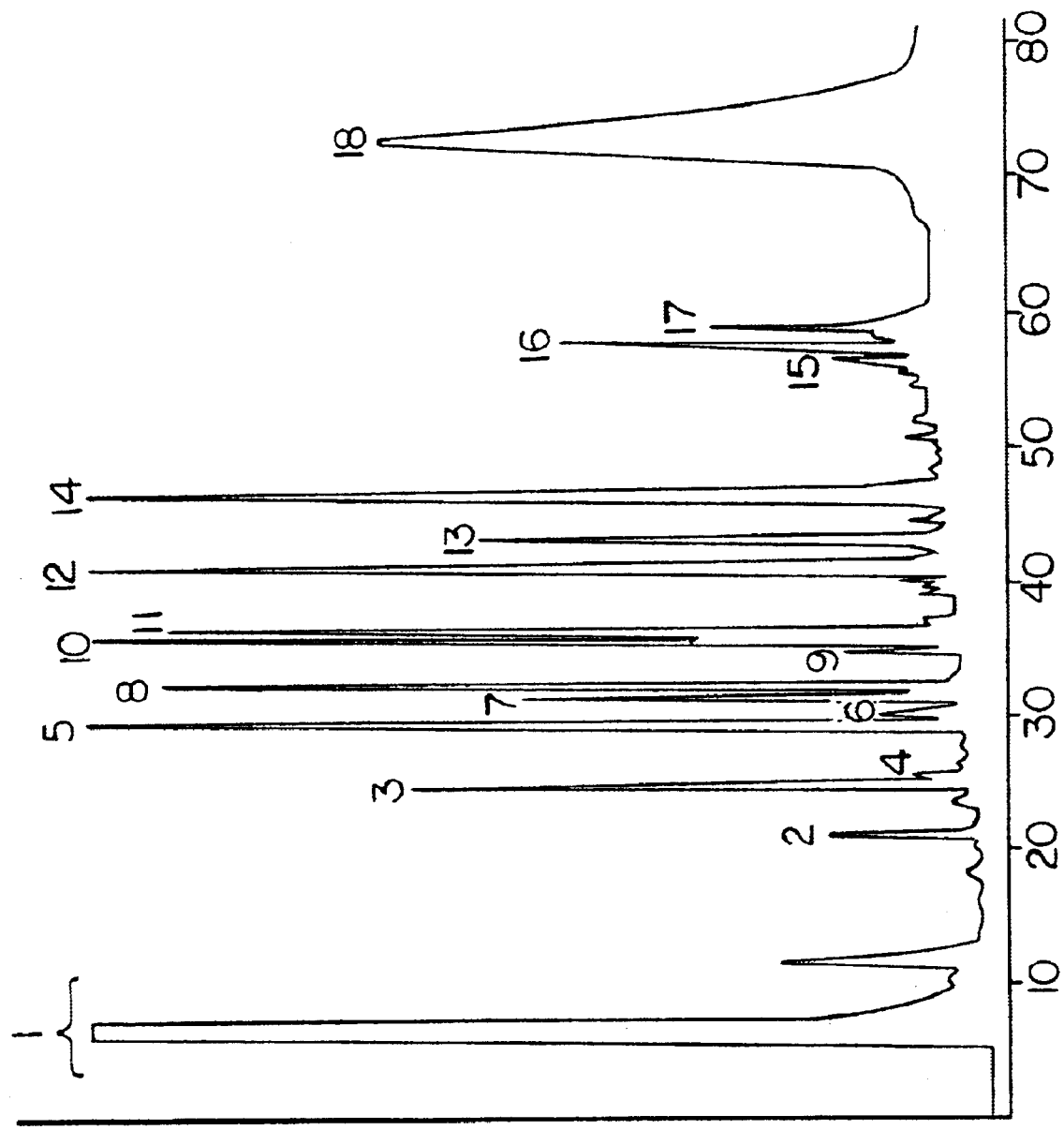

FIG. 6 depicts the reverse phase HPLC fractionation of tryptic digest of alkylated mPEG$_{5000}$*IL-1ra reacted with tritiated iodoacetic acid to label free cysteines. Separation was performed on a Brownlee C8 (2.1×220 mm) column at ambient temperature and a flow rate of 1000 µl/min with a linear gradient. Solvent A was 0.1% TFA in water and solvent B was 0.085% TFA in 80% acetonitrile and 20% H$_2$O. FIG. 6 shows peaks 1 through 18.

Figure 7:
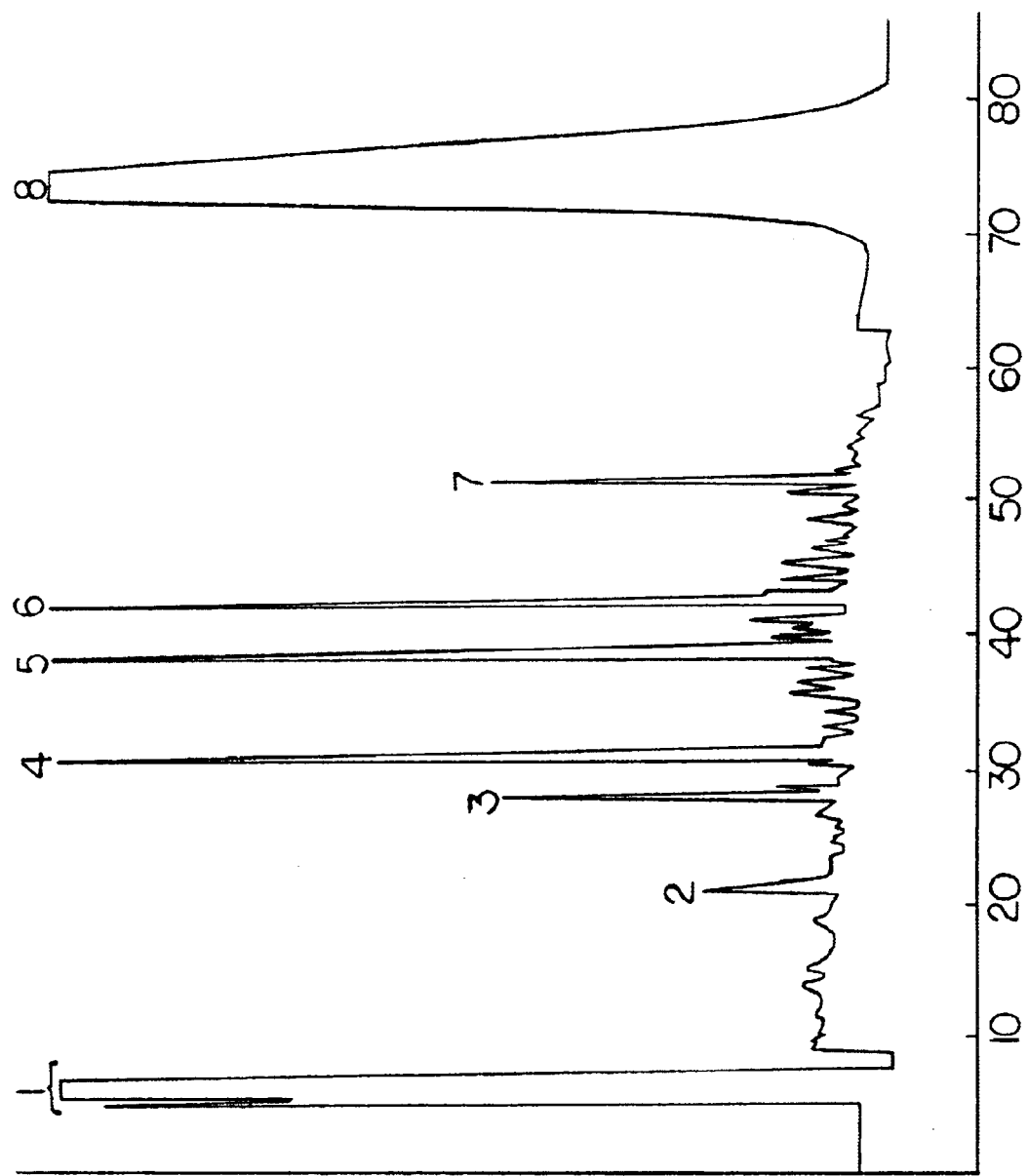

FIG. 7 depicts the reverse phase HPLC fractionation of chymotryptic digest of peptide 18 in FIG. 6. Conditions were identical to those in FIG. 6. Peptides 5 and 8 contained tritium counts and peptide 5 had the amino acid sequence LCTAMEADQPVSL. The cysteine was identified as the carboxymethylcysteine derivative. This cycle was the only one containing counts above background. The amino acid sequence of peptide 8 began with serine 103 of IL-1ra. Redigestion of this peptide with chymotrypsin permitted fractionation of all tritium counts from the peptide. FIG. 7 shows peaks 1 through 7.

Figure 8:
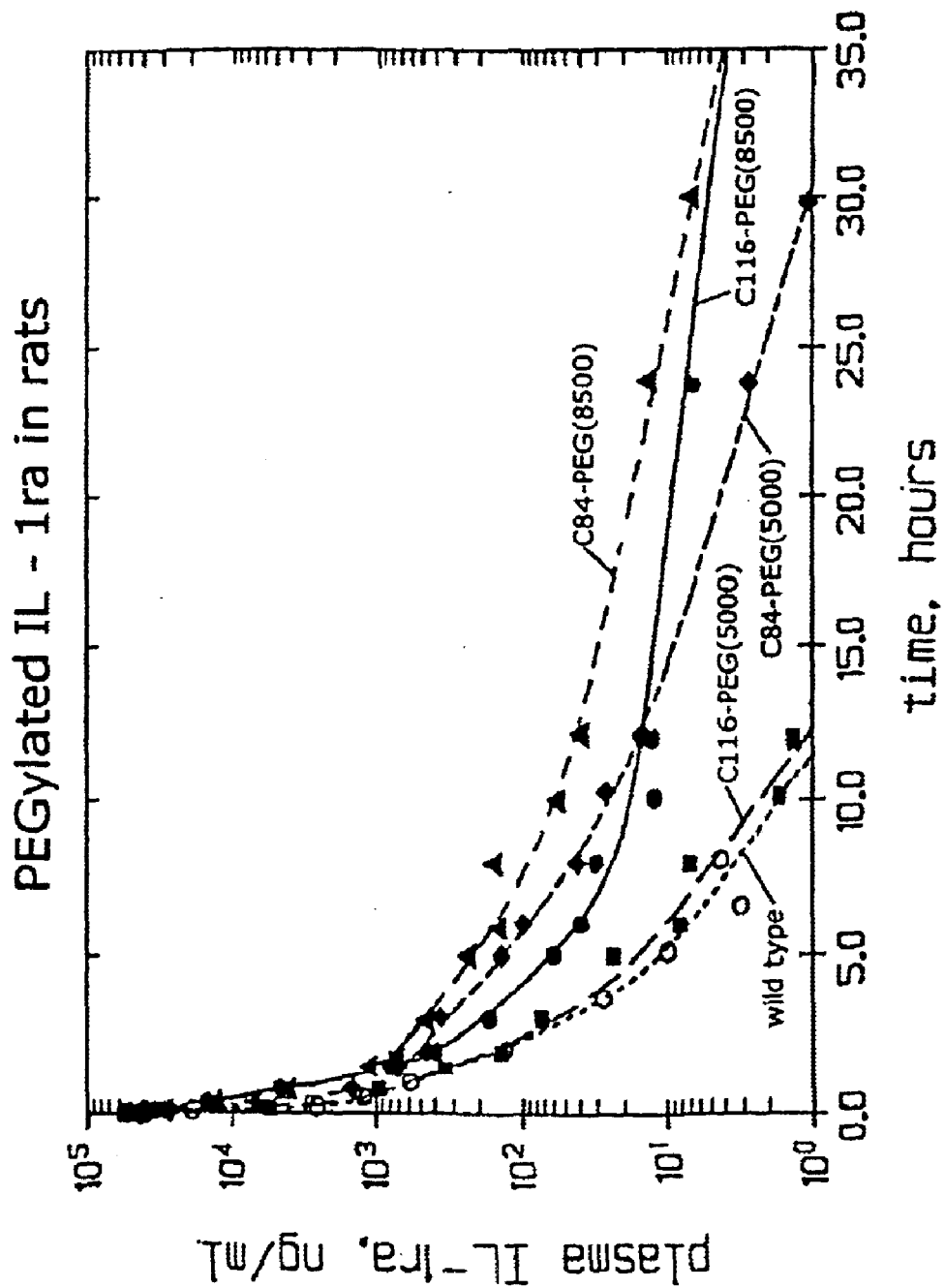

FIG. 8 depicts the plasma IL-1ra concentration versus time profiles of mature IL-1ra, pegylated IL-1ra, and several pegylated muteins of IL-1ra.

Figure 9:

FIG. 9 shows the SDS-PAGE gel showing c105 30 kDa TNF inhibitor and mPEG, and the separation of unreacted 30 kDa TNF inhibitor from mPEG c105 30 kDa TNF inhibitor by size exclusion chromatography.

Figure 10:
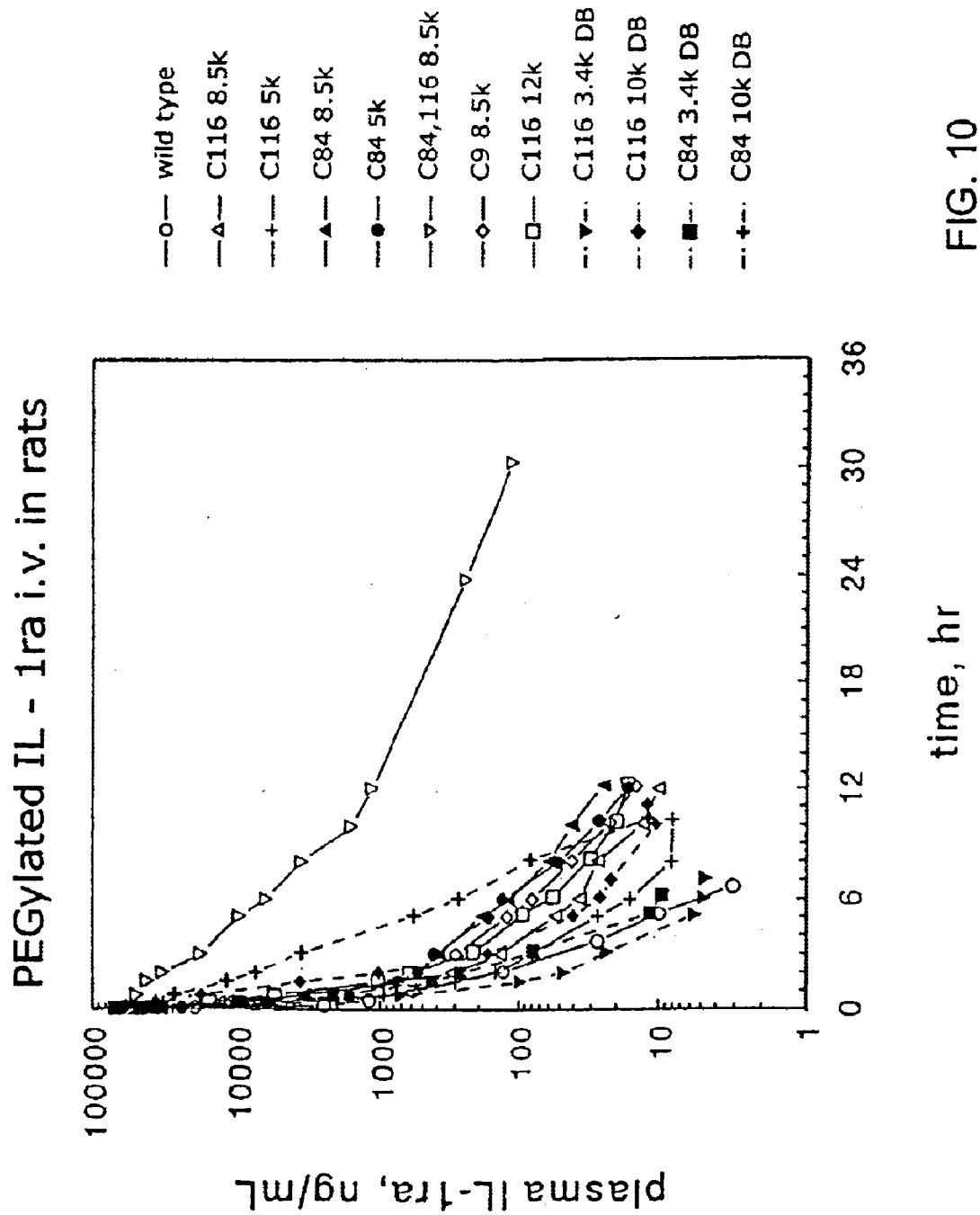

FIG. 10 shows a plot containing intravenous plasma IL-1ra concentration versus time curves for a large number of singly PEGylated IL-1ra species, doubly PEGylated IL-1ra species, and IL-1ra PEG dumbbell species.

Figure 11:
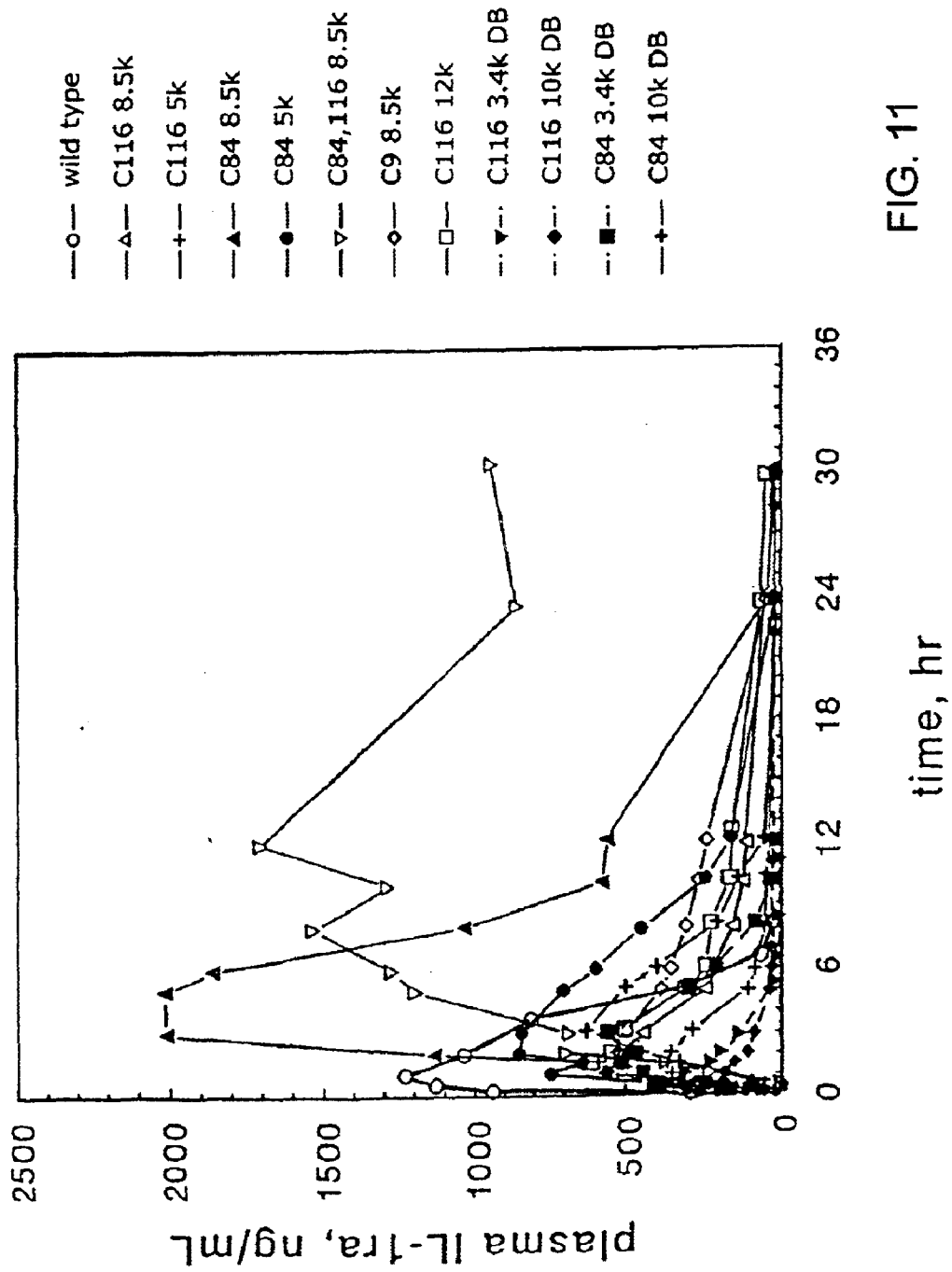

FIG. 11 shows a plot containing subcutaneous plasma IL-1ra concentration versus time curves for a number of IL-1ra species as in FIG. 10.

Figure 12:
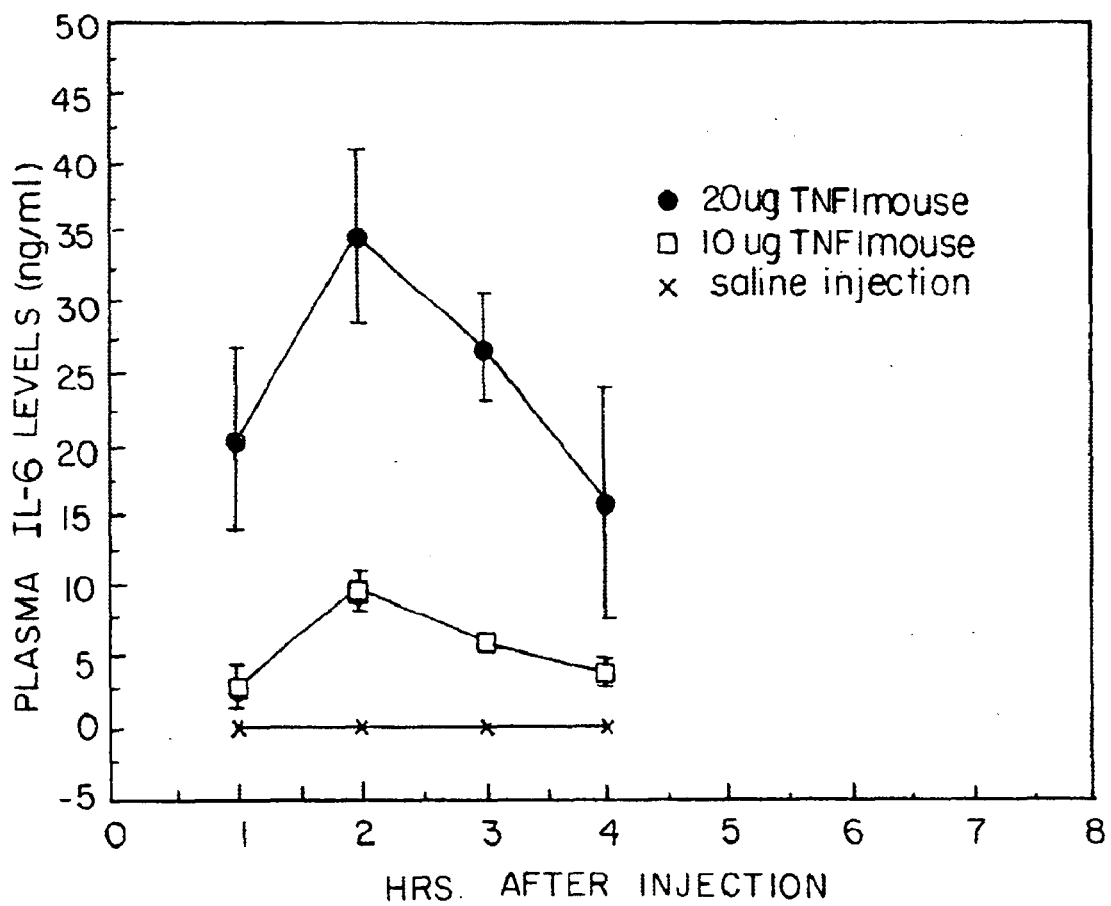

FIG. 12 shows a plot of plasma IL-6 levels versus time after the injection of mice with hrTNF.

Figure 13:
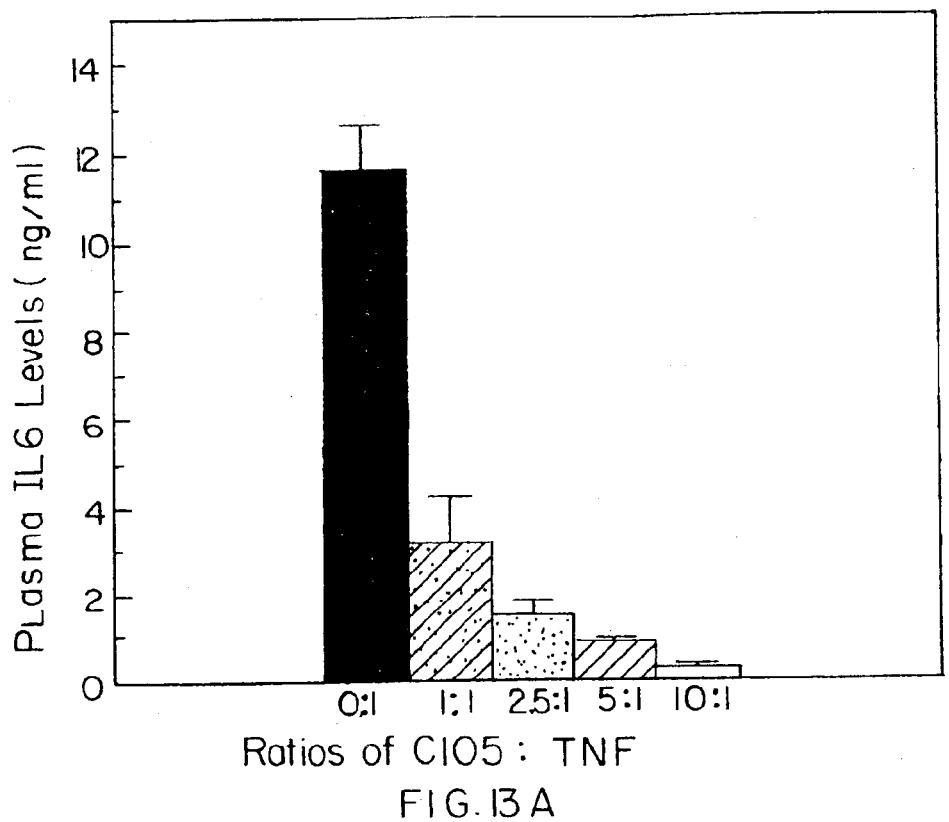
Figure 13:
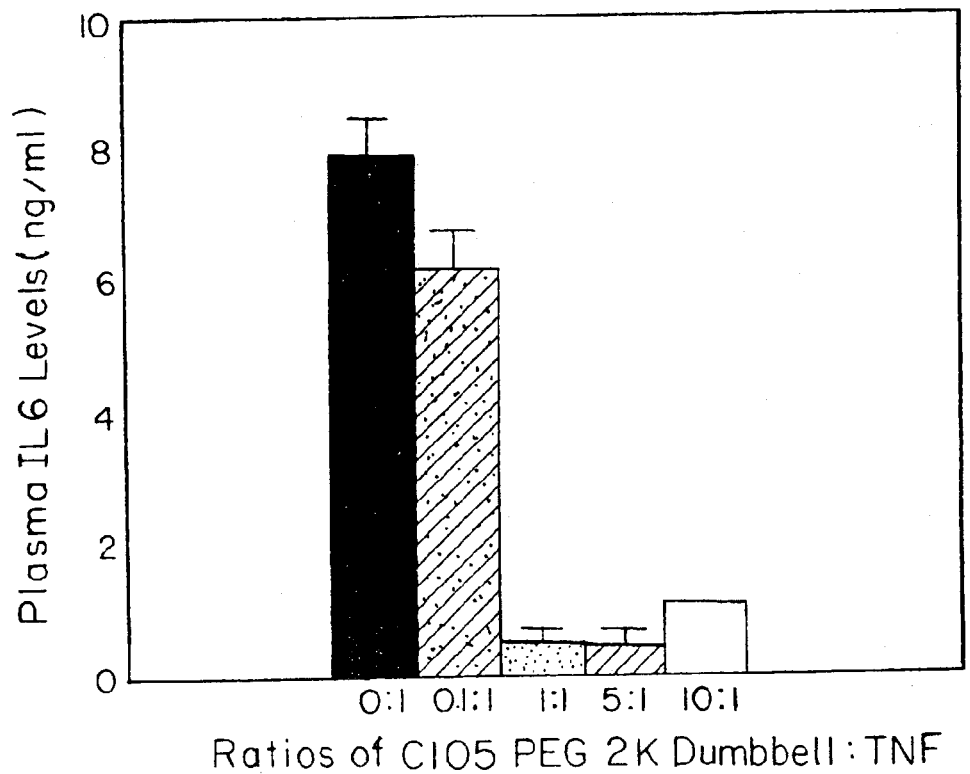

FIG. 13 compares IL-6 levels induced in mice by five ratios of c105 30 kDa TNF inhibitor to TNF (FIG. 13A) and five ratios of c105 30 kDa TNF inhibitor to PEG$_{2000}$db to TNF (FIG. 13B).

Figure 14:
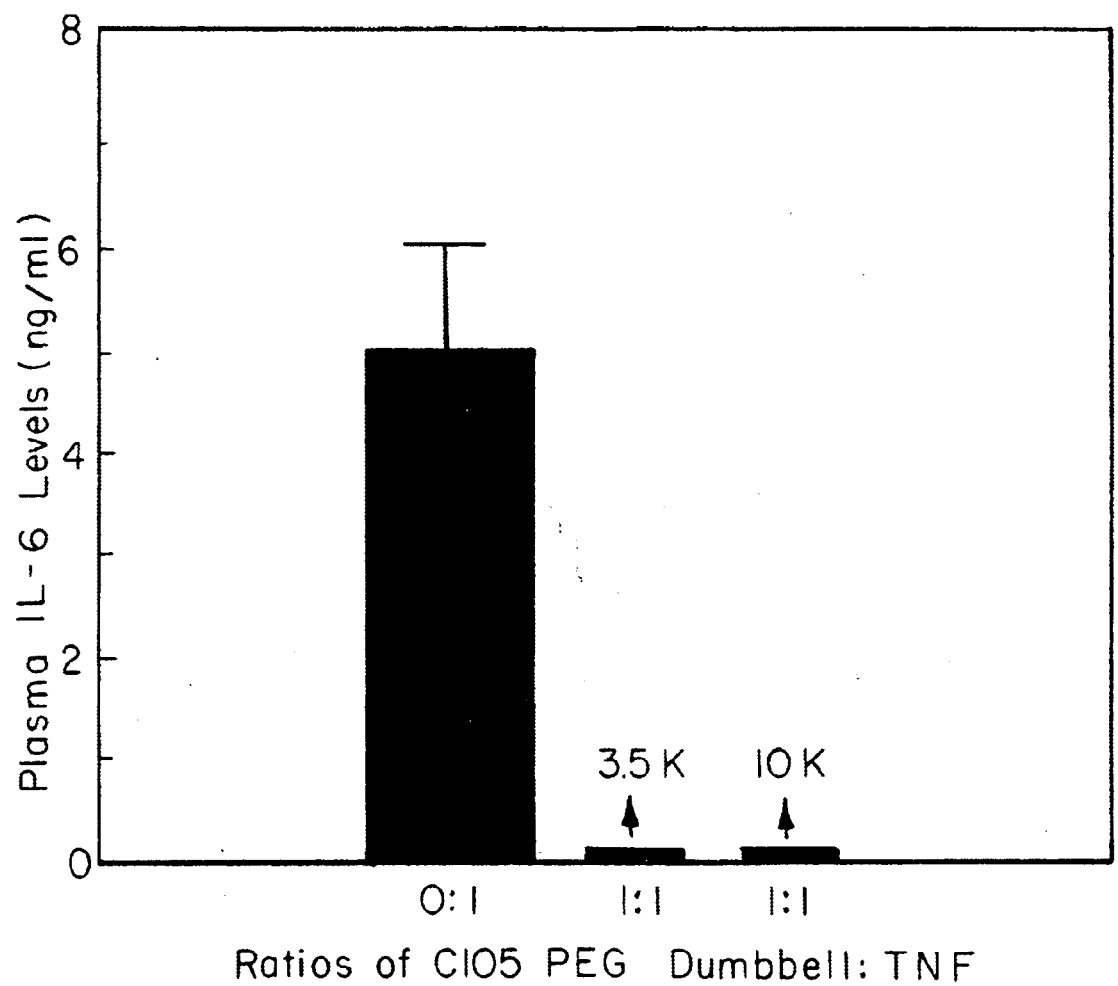

FIG. 14 depicts plasma IL-6 levels induced in mice by TNF alone and one to one ratios of TNF to c105 30 kDa TNF inhibitor PEG$_{3500}$ and PEG$_{10,000}$ dumbbells.

Figure 15B:
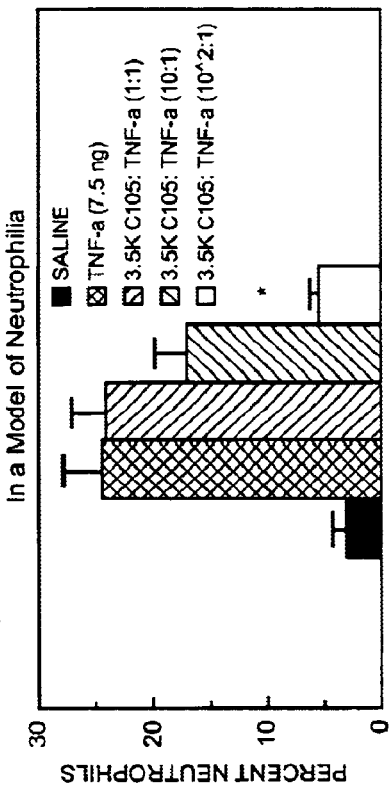
Figure 15D:
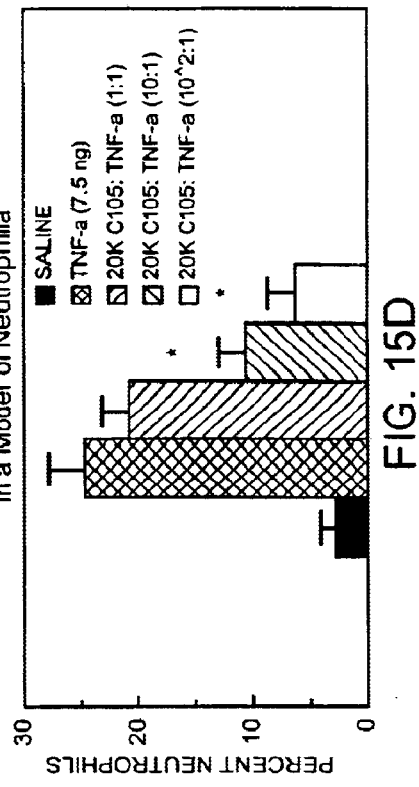
Figure 15A:
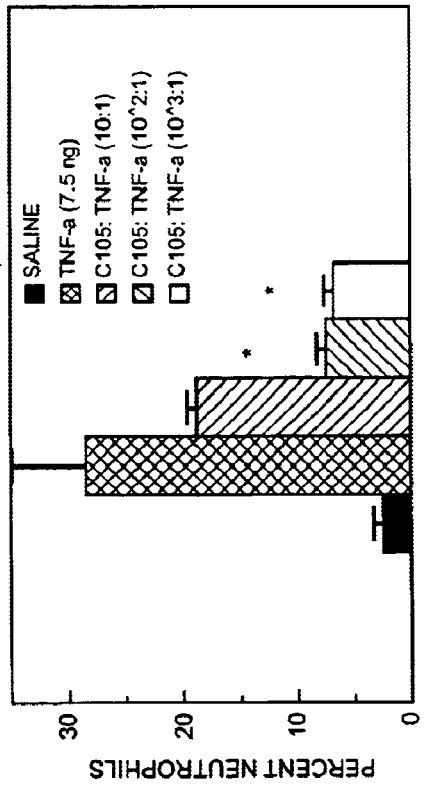
Figure 15C:
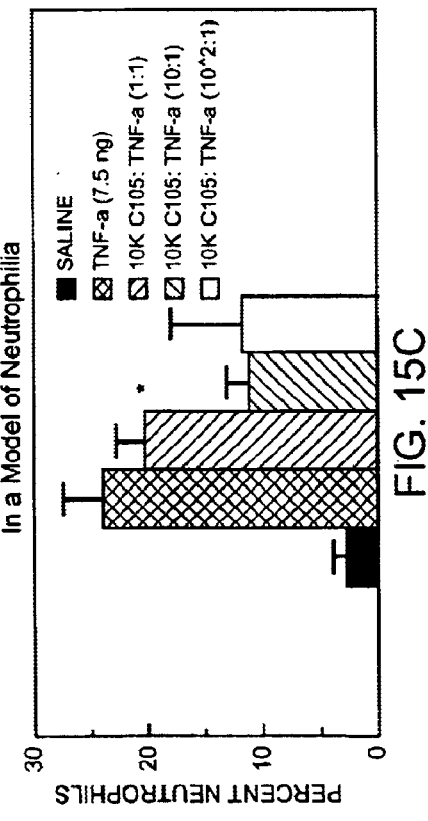

FIG. 15 depicts percent neutrophils induced by varying ratios of TNF to c105 30 kDa TNF inhibitor (FIG. 15A), c105 30 kDa TNF inhibitor PEG$_{3500}$db (FIG. 15B); c105 30 kDa TNF inhibitor PEG$_{10,000}$db (FIG. 13C); and c105 30 kDa TNF inhibitor PEG$_{20,000}$db (FIG. 15D).

Figure 16:
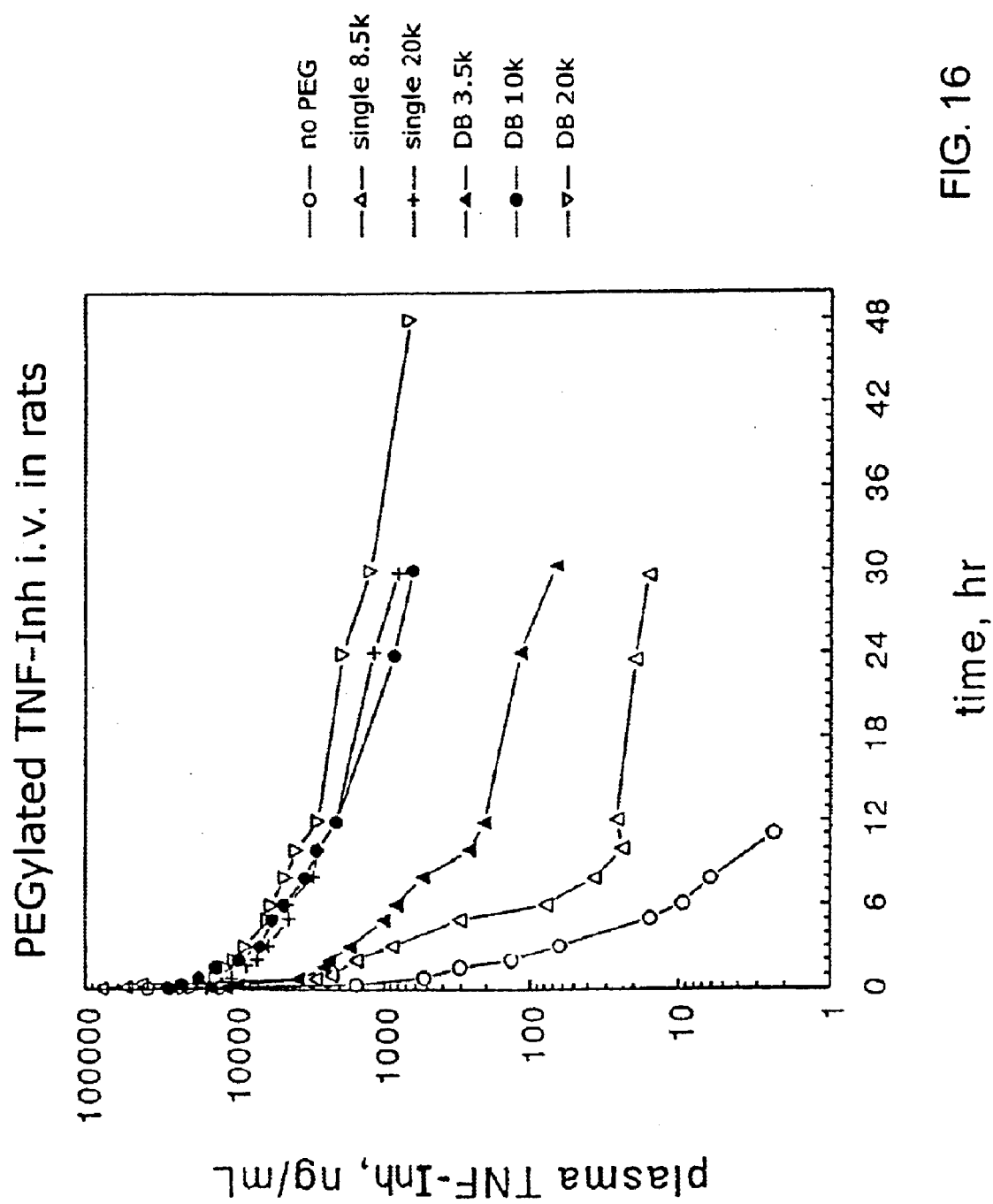

FIG. 16 shows a plot containing intravenous plasma 30 kDa TNF inhibitor concentration versus time curves for native 30 kDa TNF inhibitor, c105 30 kDa TNF inhibitor PEG$_{8500}$, and PEG$_{10,000}$ and 30 kDa TNF inhibitor PEG$_{3500}$, PEG$_{10,000}$ and PEG$_{20,000}$ dumbbells.

Figure 17:
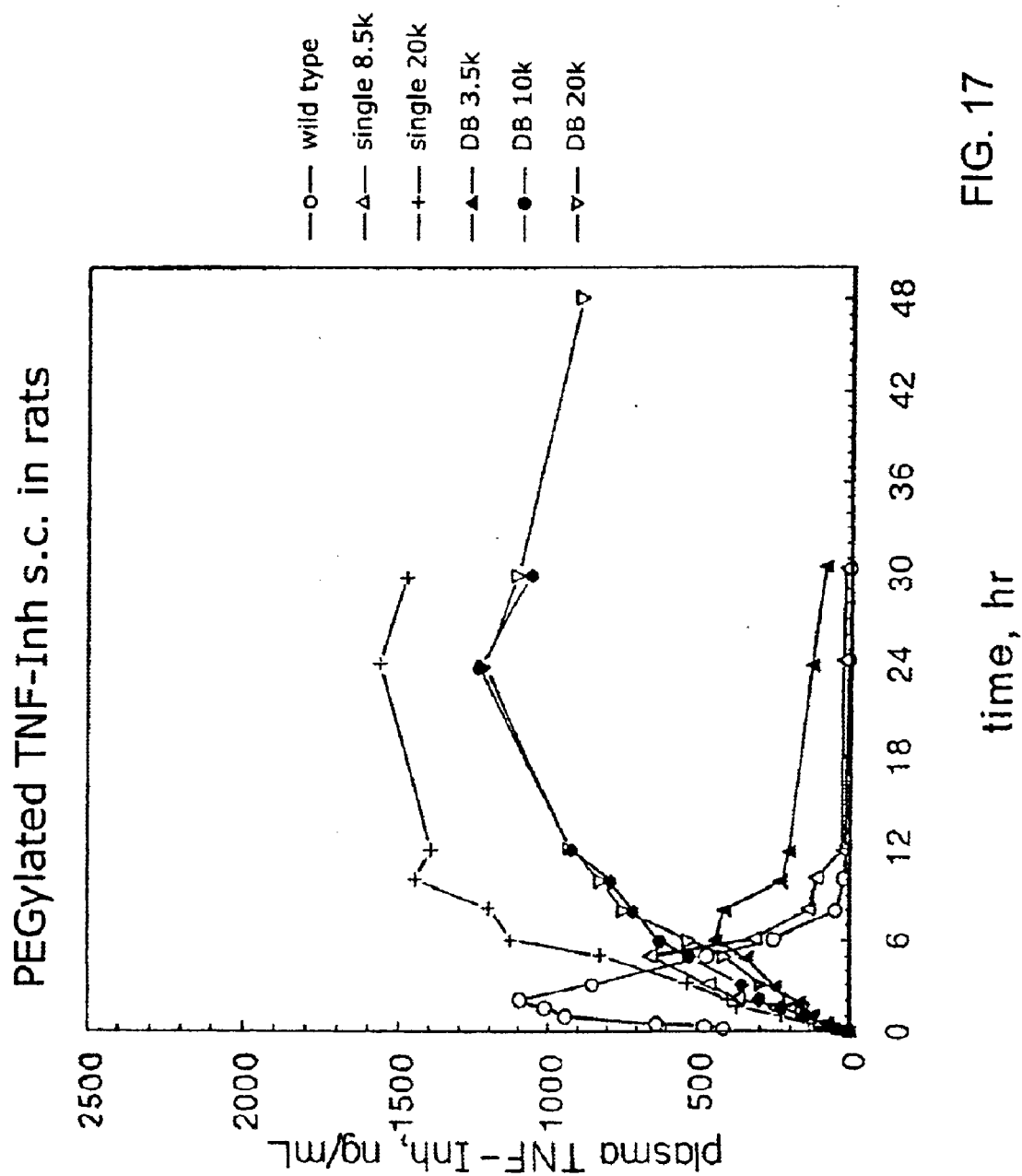

FIG. 17 shows a plot containing subcutaneous plasma 30 kDa TNF inhibitor concentration versus time curves for a number of 30 kDa TNF inhibitor species as in FIG. 16.

Figure 18:
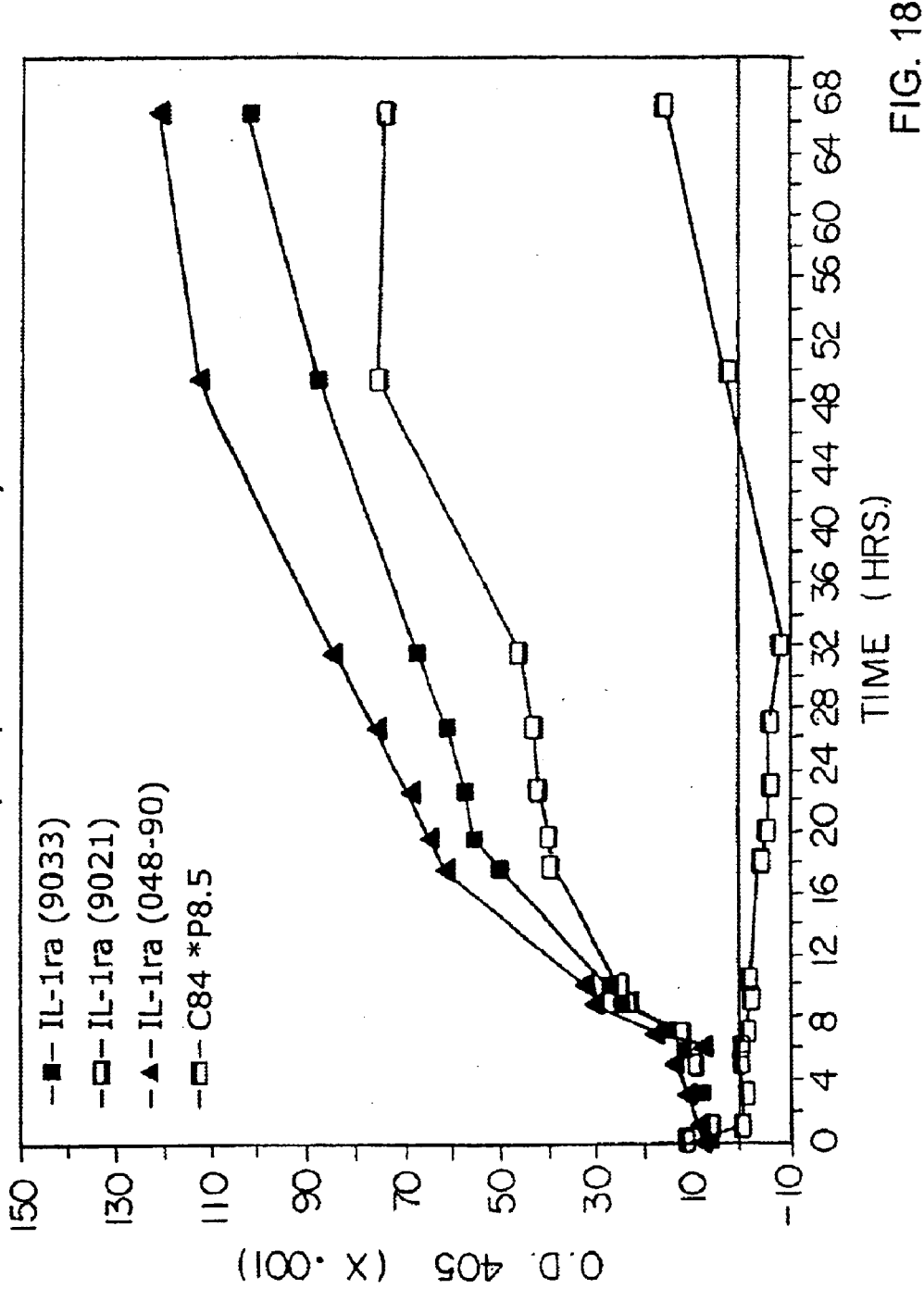

FIG. 18 depicts the solubility of 3 solutions of native IL-1ra and c84 IL-1ra PEG$_{8500}$ by plotting O.D. 405 versus time.

Figure 19:
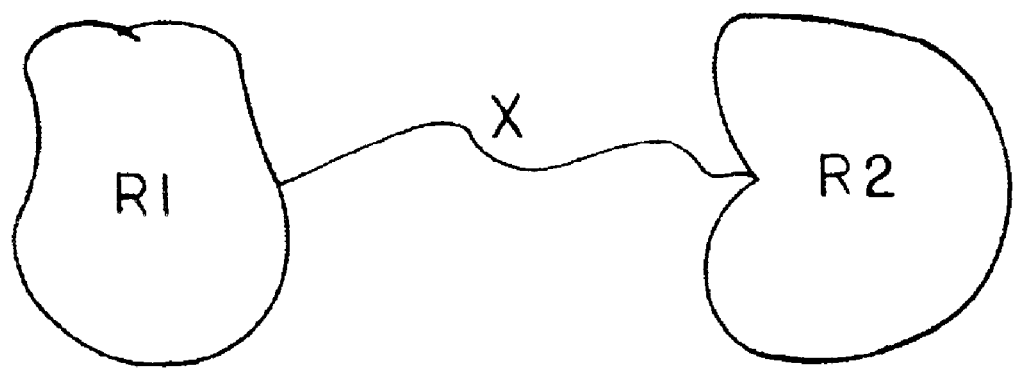

FIG. 19 depicts the basic structure of compounds of this invention having the general formula R$_1$—X—R$_2$ that are referred to as dumbbell compounds.

DETAILED DESCRIPTION OF THE INVENTION

This invention involves the selective modification of pharmaceutically useful polypeptides, in particular, Tumor Necrosis Factor ("TNF") inhibitors and interleukin-1 ("IL-1") inhibitors. More specifically this invention describes the selective modification of 30 kDa TNF inhibitor and IL-1 receptor antagonist ("IL-1ra"). The selective modifications serve to both enhance the pharmacokinetic properties of the polypeptides as well as to provide homogenous compositions for human therapeutic use.

Additional polypeptides that may be selectively modified according to the procedures of this invention include interleukin-2 receptors ("IL-2r") and CR1. All references to interleukin-2 receptor shall be construed to include both α and β chains of IL-2r unless stated otherwise.

In the preferred embodiments of the invention the modified polypeptides and DNA sequences are human. However, to the extent that there is sufficient homology between animal DNA and peptide sequences to the human forms, they would be included within the scope of this invention.

In one embodiment, the method of modification of the present invention includes covalently bonding long chain polymers to the polypeptides of interest in a site specific manner. The selected polypeptides may be the native or naturally occurring polypeptides of interest, or they may be biologically active muteins of the polypeptides that have been produced to enhance the modification process described herein. The method of the invention includes the selection, production and screening of desired muteins that will meet the objectives of this invention. In other embodiments of this invention the method for modifying polypeptides requires merely that the modification be made so that the resulting product be available in substantially purified form as that term is defined herein.

In certain embodiments, the modified polypeptides of the present invention will be bonded to long chain polymers at specific positions of the amino acid sequence. The modified polypeptides of the present invention will retain a substantial portion of their biological activity. In the preferred embodiments, the modified polypeptides will retain at least one tenth of the biological activity of the native polypeptide in a receptor binding assay. In a more preferred embodiment, the modified polypeptide will retain at least one fifth of the biological activity of the native polypeptide, and in the most preferred embodiment at least one fourth of the activity will be retained. In addition, the modified polypeptide will serve to improve the pharmacokinetic performance of the native polypeptide in at least one of the following areas:

1) increasing the apparent molecular weight of the native polypeptide and, hence, reducing the clearance rate following subcutaneous or systemic administration;

2) increasing the solubility of the native polypeptide in aqueous solutions; or 3) reducing the antigenicity of the native polypeptide.

In many embodiments of the invention, each of these objectives will be accomplished. In the preferred embodiments of the invention, the long chain polymer will be polyethylene glycol or monomethoxy polyethylene glycol. A polyethylene glycol unit will be referred to herein as PEG and a monomethoxy polyethylene glycol unit will be referred to as mPEG. The approximate molecular weight of the polymeric unit will be given in subscripts. For example, a monomethoxy polyethylene glycol unit of approximate molecular weight of 5,000 will be depicted as $mPEG_{5000}$ or $PEG_{5000}$. Other long chain polymers included within the scope of this invention are polypropylene glycol ("PPG"), polyoxyethylated glycerol ("POG"), dextran, colonic acids or other carbohydrate-based polymers and polymers of β-amino acids and biotin derivatives.

In an alternate embodiment of the present invention, the long chain polymer unit is dihydroxy polyethylene glycol, or HO—$(CH_2CH_2O)_n$—H. When activated to bind covalently with polypeptides or other biologically active compounds as described below, the dihydroxy material will contain two reactive sites.

In the preferred embodiments of the present invention the long chain polymer units are bonded to the polypeptide via covalent attachment to the sulfhydryl group (—SH) of a cysteine residue. To obtain selectivity of reaction and homologous reaction mixtures, it is useful to utilize functionalized polymer units that will react specifically with sulfhydryl groups. The functional or reactive group attached to the long chain polymer is referred to herein as the activating group. Activating groups include the maleimide group, sulfhydryl group, thiol, triflate, tresylate, aziridine, oxirane and 5-pyridyl. The preferred activating groups are maleimides.

Activated dihydroxy polyethylene glycols, because of the physical separation between the ends of the polymeric chain, are nearly equally reactive at each end of the molecule. By appropriate selection of reaction conditions and polypeptides, the activated dihydroxy polyethylene glycols—or any other multi-activated long chain polymer unit—will react with polypeptides to form "dumbbell" shaped complexes where two polypeptides are joined by a long chain polymeric unit.

By utilizing the different rates of reaction that would be found between the activated polymeric linked group and different cysteine-containing polypeptides and by the kinetics of the reactions, it is easily within the skill of those in the art to also produce dumbbell complexes where substantially purified compounds can be formed comprising two different polypeptide groups, or comprising a single polypeptide group and a different biologically active group. Examples of such heterodumbbell compounds are given below.

The extent and availability for reaction of cysteines varies dramatically from polypeptide to polypeptide. Therefore, in the biologically-active form many polypeptides do not have "free" cysteines, or cysteines not bound to another cysteine. In addition, the existence of "free" cysteines does not mean that cysteines are accessible for binding to reactive reagents. Since the modification usually occurs on the active or three dimensionally folded polypeptide, little or no reaction will occur when a free cysteine is found within the "interior" of the folded structure. A further constraint when modifying polypeptides is the potential effect the modification may have on the active site of the polypeptide. The modification of a cysteine having a certain proximal relationship to the active site may effectively deactivate the polypeptide. Even when a great deal is known about the selected polypeptide, it is difficult, if not impossible, to accurately predict which cysteine residues may be effectively modified.

The same factors also exist when mutated polypeptides are produced that contain additional cysteine residues. When the polypeptide is recombinantly produced via bacterial expression, the non-native cysteines may interfere with the proper refolding of the polypeptide. In addition, the cysteine must be accessible to the pegylating reagent, and the pegylated cysteine must not significantly interfere with the active site of the polypeptide.

The selection of potential sites within a given polypeptide for the introduction of a non-native cysteine can be influenced based on various sources of information. For example, glycosylation sites may be a good site for a mutation to include a free cysteine. To the extent that information is known about the binding or active site of the polypeptide, that information can also be used to select potential muteins. The addition or substitution of a cysteine residue at the amino terminus or carboxyl terminus of the polypeptide is also a likely prospect because of its location. And finally, the mutation of lysine residues to cysteine may be considered based on the assumption that lysines will generally be found on the surface of the biologically active polypeptide.

Although a variety of potential muteins can be selected for a given polypeptide that may meet the desired characteristics, it is only through the synthesis, pegylation and testing of such altered muteins that it will be known which will meet the objectives of the present invention. In light of this invention and the general skill and knowledge of those skilled in the art, such synthesis, pegylation and testing can be performed without undue experimentation. It should be noted, that even if the pegylation of a polypeptide acts to reduce the biological activity of a polypeptide to a certain extent, the improvement in the pharmacokinetic performance of the polypeptide may greatly increase the value of the native polypeptide in various therapeutic applications.

Upon selection of target muteins, the preferred method for the production of the muteins is by recombinantly expressing the gene coding for the mutein. Assuming that the gene coding for the native polypeptide is known, the altered gene may be created either by standard site specific mutagenesis procedures on the native gene, or by the construction of the altered gene by standard gene synthesis procedures. These techniques are well known to those of ordinary skill in the art.

The gene coding for the target mutein may be expressed in a variety of expression systems, including animal, insect and bacterial systems. To the extent that expression systems have been perfected for the expression of the native polypeptides, the same systems may be used for the target muteins. In the preferred embodiment of the present invention, the genes coding for the target muteins are produced by site specific mutagenesis of the native gene, and the gene encoding the mutein is expressed from a bacterial expression system. The gene encoding native IL-1ra and a method for expressing said gene in *E. Coli* is described in detail in U.S. Pat. No. 5,075,222 of Hannum et al., issued Dec. 24, 1991. The gene encoding native 30 kDa TNF Inhibitor and a method for expressing said gene in *E. Coli* is described in detail in U.S. patent application Ser. No. 07/555,274 filed Jul. 19, 1990. Each of these applications is incorporated herein by this reference.

The muteins and pegylated materials of the present invention include allelic variations in the protein sequence (sequence variations due to natural variability from individual to individual) and substantially equivalent proteins. "Substantially equivalent," as used throughout the specification and claims is defined to mean possessing a very high degree of amino acid residue homology (See generally, M. Dayhoff, *Atlas of Protein Sequence and Structure*, vol. 5, p. 124 (1972), National Biochemical Research Foundation, Washington, D.C. specifically incorporated herein by references) as well as possessing comparable biological activity. Preferably, the degree of homology is in excess of 70 percent, more perferably in excess of 80 percent and even more perferably in excess of 90 percent. A particularly preferred group of inhibitors are in excess of 95 percent homologous with the native inhibitor. The percentage homology as described is calculated as the percentage of amino acid residues found in the smaller of the two sequences that align with identical amino acid residues in the sequence being compared when four gaps in a length of 100 amino acids may be introduced to assist in that alignment as set forth by Dayhoff, M. D. in Atlas of Protein Sequence and Structure, Vol. 5, p.124 (1972), National Biochemical Research Foundation, Washington, D.C. Also included within the scope of this invention are muteins and pegylated polypeptides that are partially truncated versions of the native polypeptide.

In one preferred embodiment of the method of the present invention when the target mutein is produced via recombinant DNA technology in a bacterial expression system, the following steps are performed:

1) The gene coding for the target mutein is created by site directed mutagenesis of the gene coding for the native polypeptide;
2) The gene coding for the target mutein is expressed in a bacterial expression system;
3) The target mutein is isolated from the bacteria and purified;
4) The target mutain is refolded in the presence of cysteine or another sulphydryl containing compound;
5) The refolded target mutein is isolated and purified;
6) The purified and refolded target mutein is treated with a mild reducing agent;
7) The reaction mixture is dialyzed in the absence of oxygen; and
8) The dialyzed reaction mixture is treated with a long chain polymer containing an activating group.

In the preferred embodiment for the production of pegylated muteins of 30 kDa TNF inhibitor, the mild reducing agent is dithiothreitol ("DTT"). In an alternate embodiment, the modification may occur prior to the refolding of the expressed protein or mutein.

In the preferred embodiment of the present invention, the pegylated muteins and pegylated native polypeptides may be purified and formulated into pharmaceutical compositions by conventional methods. In an alternate embodiment, the purified muteins may also be formulated into pharmaceutical compositions.

The pegylated polypeptides of the present invention formed by the reaction of a deactivated long chain polymer unit have additional beneficial properties. These "dumbbell" shaped molecules can contain two of the polypeptides of interest attached by a single polymer unit. This structure imposes a certain amount of linearity to the polymeric molecule and reduces some of the steric hinderance inherent in the use of large hydrophilic polymers such as polyethylene glycol. The goal of obtaining molecules with increased apparent molecular weight is achieved while retaining high biological activity. Included specifically within the scope of this invention are bidentate molecules where two IL-1ra molecules or two TNF inhibitor molecules are covalently attached to a single polymeric chain, or where two different polypeptides are attached to a single polymeric chain, i.e., a single bidentate molecule containing both a TNF inhibitor and a IL-1ra moiety.

Figure 1:
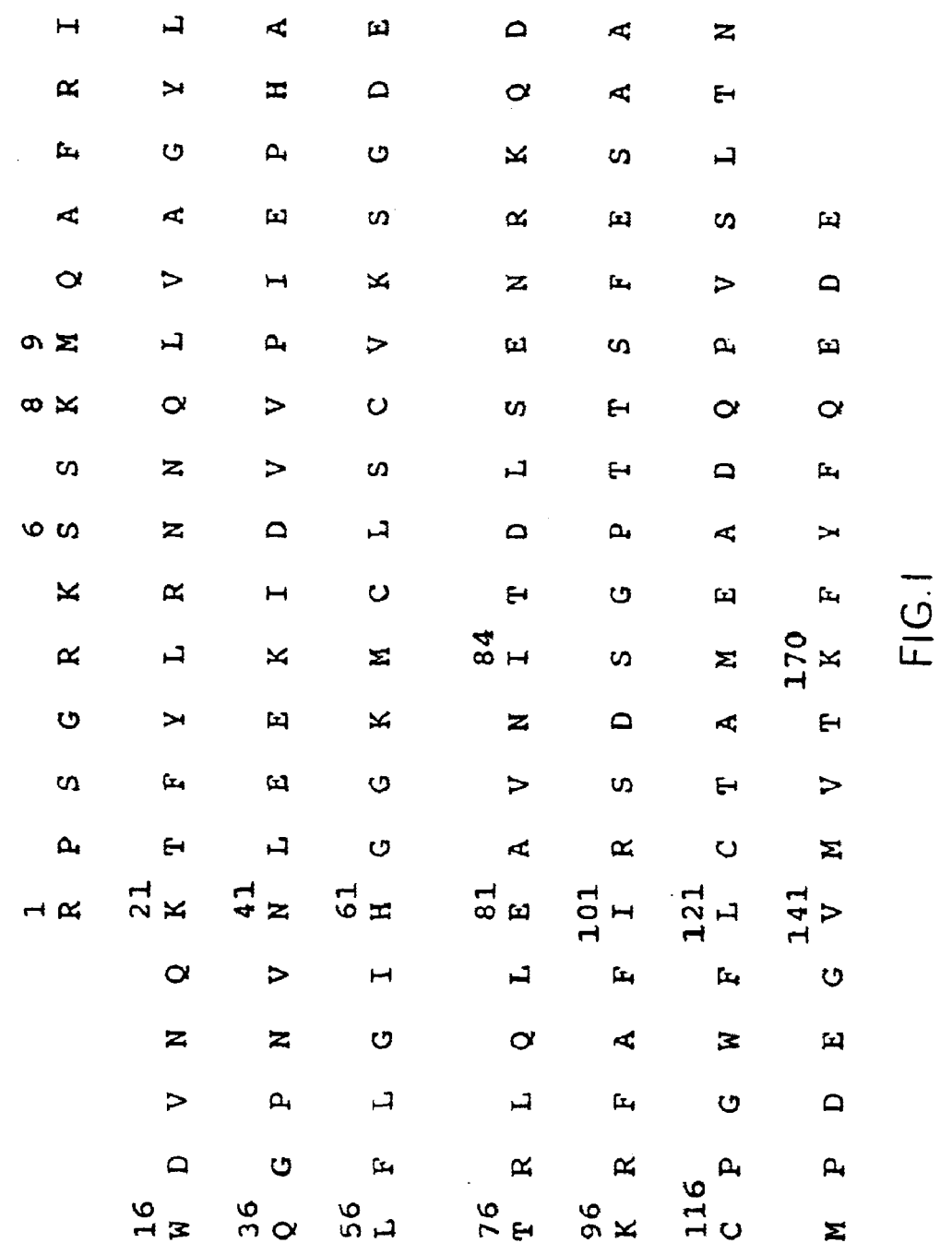

Native IL-1ra (FIG. 1) and various muteins of IL-1ra have been pegylated according to the present invention. Pegylation of wild type IL-1ra at free sulphydryl groups, by the methods described in the examples below, results in the addition of mPEG at the cysteine residue at position 116 of IL-1ra (c116). The other three cysteines are not accessible for pegylation in the fully native molecule. To attach mPEG molecules at different sites of IL-1ra and to make mPEG conjugates having more than one mPEG, IL-1ra in which native amino acids in IL-1ra were replaced with a cysteine, or additional cysteines are added at the amino-terminus of the protein. To prepare conjugates in which residue 116 is not pegylated c116 has been changed to a serine in a number of the muteins. Below is a list of the muteins that have been generated for reaction with mPEG (the residue numbering is based on the sequence given in FIG. 1; c referring to cysteine and s referring to serine):

c0s116 c0c116
c84s116 C84c116
c6s116 c6c116
c8s116 c8c116
c9s116 c9c116
c141s116 c141c116

Native 30 kDa TNF inhibitor (FIG. 2) does not contain any free cysteine residues. The following muteins of 30 kDa TNF inhibitor have been prepared (the residue numbering is based on the sequence given in FIG. 2; c referring to cysteine):

c105 30 kDa TNF inhibitor
c1 30 kDa TNF inhibitor
c14 30 kDa TNF inhibitor
c111 30 kDa TNF inhibitor
c161 30 kDa TNF inhibitor Included within the scope of this invention is an entire class of compounds, as depicted in FIG. 19, that can be represented by the formula $R_1$—X—$R_2$ wherein $R_1$ and $R_2$ are biologically active groups and at least one of $R_1$ and $R_2$ is polypeptidic, and X is a non-peptidic polymeric spacer or linker group. $R_1$ and $R_2$ may be the same group or different. Where $R_1$ and $R_2$ are different groups, both $R_1$ and $R_2$ may be polypeptidic, or $R_1$ may be polypeptidic and $R_2$ may be any biologically active group. The compounds having this structure, which have been referred to as "dumbbell" compounds, are characterized by being substantially purified. "Substantially purified" in this context is defined as being a homogenous composition.

A homogenous composition consists of one molecule of the linker X and one molecule of $R_1$ and one molecule of $R_2$. A homogenous composition includes, but does hot require, that the biologically active groups $R_1$ and $R_2$ be attached to the linker at the exact same location on the groups in each molecule of the compound. In certain is embodiments of the invention, the biologically active groups are attached site specifically to the linker. For example, in the compound c105 30 kDa TNF inhibitor $PEG_{3000}$db, two c105 30 kDa TNF inhibitor groups are attached at the 105 cysteine residue to the $PEG_{3000}$ linker.

When referring to a "homogenous composition" it is to be understood that on a molecule-by-molecule basis, the dumbbell compound is also not necessarily homogenous with respect to the exact length of the spacer group. It is understood by those skilled in the art that any production process that utilizes a given weight range of PEG or other higher molecular weight polymer begins with a solution that contains an "average" molecular weight. Therefore, when a bis-reactive PEG unit is reacted with a polypeptidic group, the PEG unit is by definition polydisperse, and the resultant dumbbell compound is heterogenous to the extent that the length of the linker is subject to the variation known to exist by those skilled in the art. In summary, "substantially purified" in this context refers to materials that are substantially free from compounds: 1) that deviate in the composition of $R_1$ or $R_2$; or 2) that are linked together by more than one linker X.

$R_1$ and $R_2$ are defined as being biologically active groups. Biologically active groups include any compound that can induce a biological effect on interact with a natural biological molecule. Biologically active groups include proteins, polypeptides, steroids, carbohydrates, organic species such as heparin, metal containing agents, vitamins, or any other biologically active species. At least one of the groups $R_1$ and $R_2$ is polypeptidic. In the preferred embodiment, both $R_1$ and $R_2$ are polypeptidic.

Polypeptidic is defined as any compound that is substantially proteinaceous in nature. However, a polypeptidic group may contain some non-peptidic elements. For example, glycosylated polypeptides or synthetically modified proteins are included within the definition.

The biologically active groups $R_1$ and $R_2$ include binding groups and targeting groups. Binding groups are defined by their affinity for a given biological ligand. Targeting groups are defined by their ability to direct the location of a complex within a biological system. $R_1$ and $R_2$ may have affinity for the same ligand, in which case the dumbbell may have enhanced affinity to that ligand. $R_1$ and $R_2$ may have an affinity for different ligands, wherein $R_1$ serves to target the complex into a location where the ligand for $R_2$ predominates.

Preferred polypeptidic groups are receptors, the extracellular portions of receptors, cell surface molecules, and extracellular matrix molecules, binding proteins, and receptor antagonists. Included among the polypeptidic groups that may be used as $R_1$ or $R_2$ are the following polypeptides and any fragment thereof: IL-1 receptor antagonist, 30 kDa TNF inhibitor, 40 kDa TNF inhibitor, Il-2 receptor, CR1 (all references to CR1 include any single or combination of consensus repeat sequences of CR1), PDGF receptor, IL-2, MCSF receptor, EGF receptor, IL-5 receptor, IL-3 receptor, GMCSF receptor, T-cell receptor, HLA-I, HLA-II, NGF receptor, IgG ($V_H$, $V_l$), CD40, CD27, IL-6 receptor, Integrins CR3, $VLA_4$, ICAM, and VCAM, CR2, GMP140 Lec domain, Laminin binding protein, Laminin fragments, Mannose binding protein, exon 6 peptide of PDGF, and proteases (with 2 catalytic domains or a target domain and a catalytic domain). All references to receptors includes all forms of the receptor whenever more than a single form exists. In the preferred embodiments, the groups $R_1$ and $R_2$ are selected from the group consisting of IL-1 receptor antagonist, 30 kDa TNF inhibitor, CR1, and IL-2 receptor (both the α and β chains).

In a preferred embodiment, the non-peptidic polymeric spacer X may be further defined as follows: $X=-Y_1-(Z)_n-Y_2-$, wherein $Y_1$ and $Y_2$ represent the residue of activating groups that react with $R_1$ and $R_2$ to link the spacer to the groups $R_1$ and $R_2$, and $(Z)_n$ represents the base polymeric group. According to the present invention n is greater than 6 and preferably is greater than 10.

Non-peptidic is defined as a polymeric group that is substantially not peptidic in nature. The inclusion of less than 50% by weight of α-amino acid residue as part of $Y_1$, $Y_2$ and Z would be considered substantially non-peptidic in nature and would be considered non-peptidic. In the preferred embodiment, the non-peptidic spacer X is non-immunogenic, and biologically inert and hydrophilic. In addition, the preferred linkers are capable of conveying desirable properties to the biologically active polypeptidic groups—such as reduced immunogencity, increased solubility, or reduced clearance rate from the body—without significantly reducing the affinity of a given $R_1$ or $R_2$ group to its ligand. In the most preferred embodiments, the compound $R_1-X-R_2$ (wherein $R_1=R_2$ and $R_1$ and $R_2$ are binding groups) has an affinity for its ligand that exceeds the affinity that the non-derivitized binding group has to the ligand. For example, substantially purified c105 30 kDa TNF inhibitor $PEG_{3400}$db has an inhibitor activity for TNF that is greater than 20 times the inhibitor activity that c105 30 kDa TNF inhibitor has for TNF.

The activating groups $Y_1$ and $Y_2$ that are part of the polymeric spacer X may be comprised of any of the activating groups as discussed above, including the maleimide group, sulfhydryl group, thiol, triflate, tresylate, aziridine, oxirane, and 5-pyridyl. The preferred activating groups are maleimides.

The polymeric group $(Z)_n$ is preferably selected from the group consisting of polyethylene glycol, polypropylene glycol, polyoxyethylated glycerol, dextran, poly β-amino acids, colonic acids or other carbohydrate polymers and polymers of biotin derivatives. In the preferred embodiments, the polymeric group is polyethylene glycol. Any non-peptidic polymeric group that would serve the functions as described herein would also be included within the scope of this invention.

One of the advantages of the present invention is the ability to vary the distance between the groups $R_1$ and $R_2$ by varying the length of the polymeric group linking the two binding groups. Although not limited by theory, it is proposed that the increase in biological activity seen for the multimeric compounds of this invention may be attributed to the multimeric nature of the cell receptors and ligands in vivo. For this reason, the optimal distance between the units $R_1$ and $R_2$ (which would be generally directly proportional to the length of the polymeric unit $(Z)_n$) may be easily determined by one skilled in the art by varying the size of the spacer X.

In one embodiment of the present invention, the groups $R_1$ and $R_2$ are the same. However, in an alternate embodiment $R_1$ and $R_2$ are different species. Such compounds can be designed to create a heterodimer wherein both $R_1$ and $R_2$ act within the same general biological systems. For example, both IL-1 receptor antagonist and TNF inhibitors are believed to disrupt the inflammation cascade. The difunctional complexes may also be designed where $R_1$ or $R_2$ is a "targeting" species that "directs" the complex to a specific location by its binding affinity to a certain substrate, and the opposing binding, roup has a desired activity at the localized site.

An example of a heterodimer that has great potential for being a successful IL-2 inhibitor is one where $R_1$ is IL-2rα and $R_2$ is IL-2rβ. Such a heterodimer mimics the receptor complex that has the highest affinity for IL-2. See Example XVII. An additional heterodimer that can act as a complement inhibitor is the heterodimer where $R_1$ is the C3b binding domain from CR1 and $R_2$ is the C4b binding domain from CR1. See Example XVIII. In an additional heterodimer $R_1$ is the exon 6 peptide of PDGF and $R_2$ is IL-1ra. See Example XIX.

In the preferred embodiment of the invention, the procedures for producing the bifunctional $R_1$—X—$R_2$ complexes are essentially the same as those used for the site-selective reaction of polypeptides as described above. The synthesis of c105 30 kDa TNF inhibitor $PEG_{3400}$db is described below in Example 13. A bis-reactive polymeric group is reacted with a cysteine-containing polypeptide, wherein the activating group on the bis-reactive polymeric group forms a thio-ether bond with the selected free cysteine residue. As described above, the cysteine may be a free cysteine naturally-occurring on the polypeptidic group, or a non-native cysteine that has been added or substituted into the natural sequence.

The preferred bis-reactive polymeric compound of the present invention is α-(2-maleimido)ω-maleimido poly (oxyethylene) or bis-maleimido PEG. The synthesis of bis-maleimido PEG is described in Example 12. According to the preferred method, the bis-maleimido compound is prepared from bis-hydroxyl PEG via the bis-amino intermediate.

Several methods for the conversion of the terminal hydroxyls of PEG to the corresponding amino group have been reviewed by Harris et al., *J. Polymer Sci.* vol. 22, pg. 341 (1984); Harris, *Rev. Macromol, Chem.* vol. c25(3), pg. 325 (1985). This is accomplished by generating a reactive intermediate via either sulfonation, halogenation, or oxidation of the hydroxyl followed by displacement of the activated termini by a nucleophile.

Other practical alternatives to the synthesis of the bis-maleimide PEG given in Example 12 also exist. The reactive intermediate in the conversion of the hydroxyl to the amine may be the halogenated derivative (e.g. the α-(bromoethyl) -ω-bromopoly(oxyethylene) intermediate (Johannson, *Biochim. et Biophy.* vol. 222, pg. 381 (1970)) followed by direct substitution with ammonia, (Buckmann et al., *Makromol. Chem.* vol. 182, pg. 1379 (1981)) or the aldehyde intermediate (Harris, supra.) The bis-maleimide PEG is not the only sulfhydryl-specific reagent that may be used. Glass and coworkers have developed another method for the attachment of PEG to sulfhydryls. Glass et al., *J. Biopolymers* vol. 18, pg. 383 (1979). However, the reaction is reversible with thiols. Another method for attachment of PEG to cysteinyl sulfhydryls is the bis-4-vinylpyridine PEG derivative.

Harris (supra) also reviews the synthesis of a variety of electrophilic derivatives of PEG that can be used as reagents to modify proteins. The reagents include chlorocarbonates, isocyanate, epoxide, succinimidyl succinate, cyanuric chloride, mixed anhydride, carbodiimides and sulfonates. The latter group includes tresylate, tosylate, and mesylates. Some of the reagents react selectively with amines (e.g., cyanuric chloride and carbodiimides) while others react with both sulhydryls and amines (e.g., epoxide and tresylates). Some of these reagents have been used to modify proteins and may result in varying degrees in loss of activity.

The preferred preparation of $R_1$—X—$R_2$ complexes where $R_1$ and $R_2$ are different requires a two step process where the bis-reactive polymeric group is reacted in series with $R_1$ and then $R_2$. The preparation of such heterodimers may be accomplished by those of ordinary skill in the art without undue experimentation. In some cases the intermediate $R_1$—X must first be isolated and purified prior to reaction with $R_2$, and in other circumstances an intermediate purification may not be necessary.

The extracellular domains of both IL-2rα and IL-2rβ may be cloned using PCR and cloned into a vector capable of directing expression in *E. coli*. The proteins may be refolded and purified from *E. coli* and their ability to inhibit IL-2 activity measured in bioassays. In vitro mutagenesis can be used to substitute native residues in the molecules with cysteine to allow for site directed attachment of PEG. Muteins of both IL-2rα and IL-2rβ may then be identified that allow for efficient attachment of PEG which do not lose activity when PEGylated. A PEG-linked heterodimer may be formed by first PEGylating IL-2rα in the presence of an excess of bis-maleimido PEG. The singly PEGylated IL-2rα may be purified and IL-2rβ added to react with the active maleimide group and form the heterodimer. This molecule may be purified and its activity assessed. This molecule should mimic the high affinity IL-2 receptor found on cell surfaces.

A dumbbell complex where $R_1$ is IL-2 and $R_2$ is IL-2rβ should also be useful as a receptor antagonist of IL-2.

EXAMPLE I

Snythesis of Polyethylene Glycolating Agents

Three reagents are described to indicate the diverse means that may be used to derivatize polypeptides. See, Appendix to Example 1, for structures of Intermediates and reagents described below. All references provided below are specifically incorporated herein by this reference.

A. Synthesis of Reagent 1: $mPEG_x$-Ester-Maleimide

The succinate ester derivative of the $mPEG_x$ (intermediate 1) was prepared as described by Wie et al. *Int. Archs. Allergy App. Immun.*, vol. 64, pp. 84–99 (1981). The resulting product was weighed out and dissolved in a minimum of dry dioxane at 60° C. After the solution had cooled to ambient temperature, equimolar amounts of both tri-n-butylamine and isobutyl chloroformate were added. The reaction proceeded thirty minutes with stirring. During this time, a borate buffer, pH 8.8, was made by titrating a solution of 0.5 M boric acid with 1,6-hexanediamine. The solution containing the mixed anhydride was added dropwise to an aliquot of the borate buffer containing a 10-fold molar excess of 1,6-hexanediamine over the mixed anhydride. The reaction mixture was exhaustively dialyzed versus deionized water at 4° C. and lyophilized. This polymer intermediate (intermediate 2) was reacted with a 2.5:1 molar excess of sulfosuccinimidyl 4-(N-maleimiodethyl) cyclohexane-1-carboxylate (sulfo-SMCC, Pierce Chemical Co., Rockford Ill.) in 50 mM sodium phosphate or HEPES buffer, pH 7.0, for two hours at room temperature. The resulting polymer was purified by size exclusion chromatography of the reaction mixture on Sephadex G-25 using 50 mM sodium phosphate (or HEPES) pH 7.0 for elution at 4° C. The maleimido-polymer (reagent 1) eluted at the void volume of the column and was detected by monitoring its absorbance at 260 nanometers. The reagent was used to alkylate polypeptides within one hour of its purification. Since the mPEG from this reaction can be removed by base hydrolysis, this reagent is useful for identifying the site of mPEG attachment to the protein.

B. Synthesis of Reagent 2: $mPEG_x$-Amide Maleimide

The $mPEG_x$-tosylate (intermediate 3) was prepared as described by Pillai et al. *J. Org. Chem.* vol. 45, pp. 5364–5370 (1980). The amount of sulfonated intermediate was estimated spectrophotometrically as described by Nilson and Mosbach, in *Methods of Enzymology*, vol. 104, pp. 56–69, Academic Pres. Inc., N.Y., N.Y. (1984). This intermediate was converted to the phthalimide derivative (intermediate 4) and subsequently reduced with hydrazine hydrate to the $mPEG_x$—$NH_2$ intermediate (intermediate 5) by the procedure of Pillai et al., supra. The amino group capacity in equivalents per gram of product was quantified by microtitration with hydrochloric acid. The $mPEG_x$—$NH_2$ was reacted with sulfo-SMCC in HEPES or phosphate buffer pH 7.2 at room temperature for two hours. The amount of the $mPEG_x$-amine to sulfo-SMCC was tested at molar ratios of 5:1 to 1:5.

To determine the optimal conditions the final reagent (reagent 2) was used in pegylation reactions and the quantity and quality of $mPEG_x$*IL-1ra (we will use this designation for the pegylated product of IL-1ra reacted with reagent 2 and $mPEG_x$IL-1ra for pegylated IL-1ra from a reaction with reagent 3 described below) obtained from these reactions was assessed by SDS-polyacrylamide gel electrophoresis (PAGE). The optimal result was seen with a 1:1 ratio of SMCC to $mPEG_x$—$NH_2$. Higher proportions of sulfo-SMCC generated multiple higher molecular weight derivatives of IL-1ra on SDS-PAGE and multiple peaks on analytical ion exchange chromatography and lower proportions resulted in a reduced yield of pegylated protein. Reagent 2 was purified by size exclusion chromatography using G25 sephadex resin.

C. Synthesis of Reagent 3: $mPEG_x$-Maleimide

The $mPEG_x$—$NH_2$ (intermediate 5) can be modified further to yield a different maleimido-derivative (reagent 3). The latter was accomplished by reacting the $mPEG_x$—$NH_2$ with maleic anhydride via an adaptation of the procedure of Butler and Hartley, in *Methods of Enzymology*, vol. XXV pp. 191–199, Academic Press. Inc., N.Y., N.Y. (1972) and cyclizing this intermediate (intermediate 6) to the corresponding O-(2-maleimido ethyl)-O'-methylpolyethylene glycol using the method described by Wunsch et al., *Biol. Chem. Hoppe-Seyler*, vol. 366, pp. 53–61 (1985).

APPENDIX TO EXAMPLE I

Synthesis of Reagent 1

Structures of starting material, intermediates and reagent from synthesis 1.

Starting material:

Generalized formula for monomethoxypolyethylene glycol (mPEGx):

where x denotes the average molecular weight of the polymer in kilodaltons and n is the average number of repeating oxythylene groups.

Intermediate 1:

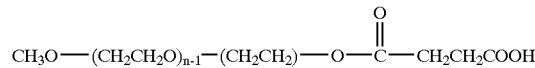

Intermediate 2:

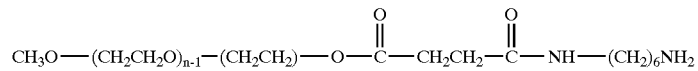

Reagent 1:

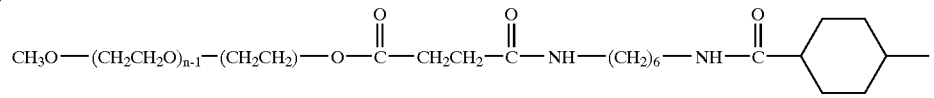

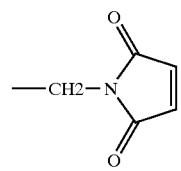

Synthesis of Reagent 2

Structures of Starting Material, Intermediates and Reagent from Synthesis 2

Starting material:
Generalized formula for monomethoxypolyethylene glycol (mPEGx):

$$CH_3O-(CH_2CH_2O)_n-H$$

where x denotes the average molecular weight of the polymer in kilodaltons and n is the average number of repeating oxyethylene groups.

Intermediate 3:

$$CH_3O(CH_2CH_2O)_{n-1}-(CH_2CH_2)-O-\overset{\overset{O}{\|}}{\underset{\underset{O}{\|}}{S}}-\text{C}_6\text{H}_4-CH_3$$

Intermediate 4:

$$CH_3O(CH_2CH_2O)_{n-1}-(CH_2CH_2)-N(\text{phthalimide})$$

Intermediate 5 (mPEGx-NH$_2$):

$$CH_3O-(CH_2CH_2O)_{n-1}-(CH_2CH_2)-NH_2$$

Reagent 2:

$$CH_3O-(CH_2CH_2O)_{n-1}-(CH_2CH_2)-NH-\overset{O}{\overset{\|}{C}}-\text{cyclohexyl}-CH_2-N(\text{maleimide})$$

Synthesis of Reagent 3

Structures of Starting Material, Intermediates and Reagent from Synthesis 3

Starting material:
Intermediate 5 (mPEG$_x$—NH2):

$$CH_3O-(CH_2CH_2O)_{n-1}-(CH_2CH_2)-NH_2$$

Intermediate 6:

$$CH_3O-(CH_2CH_2O)_{n-1}-(CH_2CH_2)-NH-\overset{O}{\overset{\|}{C}}-CH=CH-COOH$$

Reagent 3:
O-(2-maleimidoethyl)-O'-methyl polyethylene glycol $$CH_3O-(CH_2CH_2O)_{n-1}-(CH_2CH_2)-N(\text{maleimide})$$

EXAMPLE II

Preparation of Pegylated Native IL-1ra

Various parameters were tested in optimizing the pegylation reaction of native IL-1ra with successful pegylation assayed by visual inspection for a single tight band at 29 kilodaltons on Coomassie stained SDS-PAGE and a single sharp peak by analytical ion exchange chromatography. Unless otherwise stated, pegylation reactions were done at 1 mg/ml of native IL-1ra at room temperature in HEPES buffer pH 7.2 with a mPEG reagent to IL-1ra ratio of 2:1. The reagent used in these studies was mPEG-amido-maleimide (Reagent 2) and the product is referred to as mPEG$_x$*IL-1ra but the results are applicable to all three reagents.

A. Time

Pegylation reactions at room temperature were analyzed from 0.5 to 24 hours. Conversion of the IL-1ra to the pegylated form is complete (80%–90%) in two to four hours and the total amount of mPEG*IL-1ra does not increase or decrease after longer periods of incubation. The quality of the mPEG*IL-1ra assayed by SDS-PAGE decreases at longer times due to the appearance of additional bands and smears at higher molecular weights on the stained gel.

B. Temperature

Pegylation reactions were incubated at temperatures of 4°, 25°, 37°, and 50° C. and then analyzed at time points of 0.5, 1, 2, 4 and 17 hours. The reactions at 25° and 37° generated a large amount (about 50%–80%) of pegylated protein within one to two hours but those at 4° C. and 50° C. resulted in a much lower yield (10%–20%) even at the later time points. The quality of the mPEG*IL-1ra does not seem to change significantly with temperature.

C. Protein Concentration

Pegylation reactions have been done with protein concentrations (native IL-1ra) between 50 ug/ml and 10 mg/ml. All of the concentrations tested worked well and there was no difference in the quality of the mPEG*IL-1ra.

D. pH

Native IL-1ra was pegylated under the reaction conditions stated above between pH 5.5 and 7.5. The quality of the mPEG*IL-1ra is slightly better by SDS-PAGE and ion exchange at a lower pH (5.5) but the percent conversion is the same.

E. mPEG-Amido-Maleimide to Native IL-1ra Ratio

We tested ratios of between 0.5:1 to 20:1 of the mPEG-amido-maleimide to native IL-1ra. Ratios higher than about 2:1 result in efficient conversion to the pegylated form of IL-1ra (50%–90%). Ratios greater than 5:1, however, generate lower quality mPEG*IL-1ra by increasing the amount of extra high molecular weight bands on reduced SDS-PAGE and multiple peaks on ion exchange chromatography.

Figure 3:
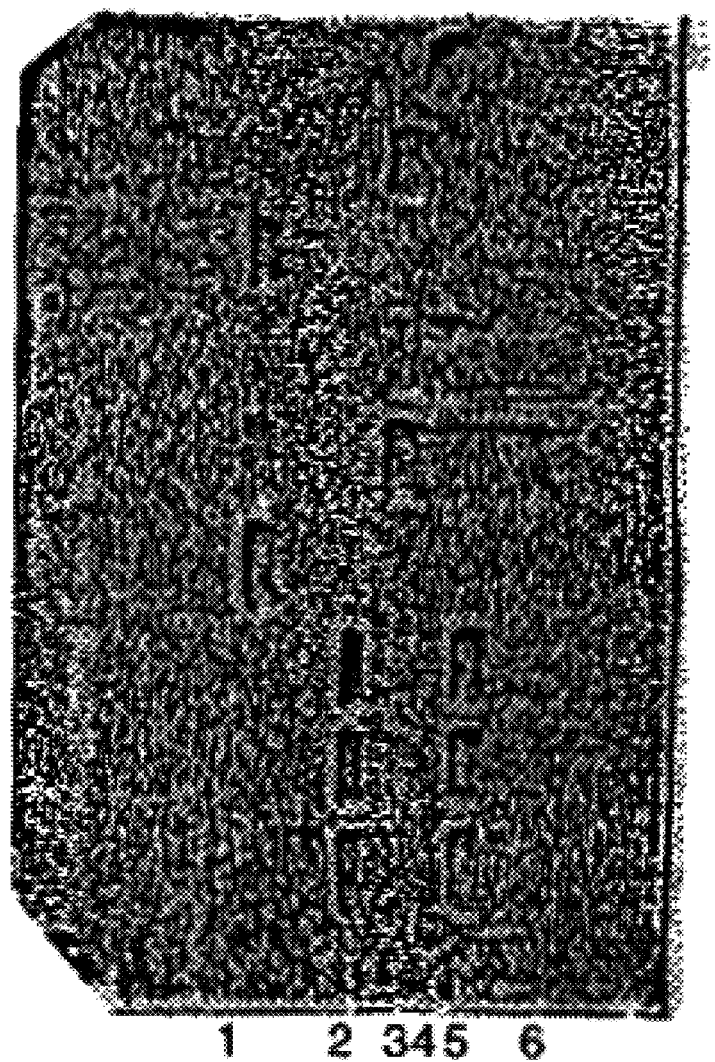
FIG. 3 shows the Coomassie SDS-PAGE of unpegylated and pegylated forms of IL-1ra and the mutein c84s116

The optimal reaction conditions for both quantity of mPEG*IL-1ra obtained and quality of the material, within the parameters used, is a 2:1 mPEG-amido-maleimide/IL-1ra at 25° C. for 2–4 hours using mPEG-amido-maleimide generated with a 1:1 ratio of Sulfo-SMCC to mPEG-amine. With these conditions 80–90% of the IL-1ra is converted to the pegylated form using reagent synthesized with either mPEG$_{5000}$ or mPEG$_{8500}$ as the starting material (FIG. 3).

F. Preparation of IL-1ra Peg Dumbbells

PEG dumbbell complexes containing IL-1ra are made according to the same procedures as other PEGylated IL-1ra species. A 2–4 molar excess of bis-maleimido PEG to IL-1ra in HEPES buffer at 7.0 is used. With IL-1ra, the species used may be the wild type molecule, which has a free and available cysteine residue, or a mutein prepared as described herein. The IL-1ra is at a concentration of 2–5 mg/ml. The reaction is incubated at ambient temperatures for 4 to 6 hours. The IL-1ra PEG dumbbell compounds are purified from the unPEGylated and singly PEGylated species by MonoS cation exchange at pH5.5 in 20–50 mM MES buffer using a gradient from 0 to 1000 mM NaCl. Further purification may be achieved by size exclusion chromatography using a BioRad TSK 250 or Superdex 75 column, as described below.

EXAMPLE III

Purification of Pegylated Native IL-1ra

Purification of mPEG$_x$*IL-1ra can be achieved by cation exchange or size exclusion chromatography. These procedures are applicable to pegylated IL-1ra derived from all three reagents described above.

Cation Exchange Chromatography

The mPEG$_x$*IL-1ra can be purified using a MonoS (Pharmacia) column with 20 mM MES buffer at pH 5.5. The proteins were eluted from the column using a salt gradient from 0 to 500 mM NaCl in the same buffer. For example, unmodified IL-1ra elutes at 220 mM NaCl, while the purity is assessed by various techniques including analytical ion exchange chromatography and SDS-PAGE. mPEG$_{5000}$ IL-ra elutes at 160 mM (FIGS. 4A and 4B).

B. Size Exclusion Chromatography

The mPEG$_{5000}$*IL-1ra, which runs as about 52 kd, and mPEG$_{8500}$*IL-1ra, which runs as about 68 kd (based on column calibration with known size standards), can easily be separated from unmodified IL-1ra (17 kd) by size exclusion chromatography on a Superdex 75 (Pharmacia) column with standard chromatographic techniques (FIG. 5).

EXAMPLE IV

Characterization of the mPEG$_x$*IL-1ra

Purified mPEG$_x$*IL-1ra gave a single symmetrical peak upon rechromatography on MonoS and appeared pure by both SDS-PAGE and size exclusion chromatography (FIG. 3 and FIG. 4B). A comparison of the tryptic maps of IL-1ra and mPEG$_{5000}$*IL-1ra showed one peak, corresponding to the peptide containing c116 and c122, absent from the conjugate map with the appearance of a new broad peak in this map. Subdigestion of this new peak with chymotrypsin and subsequent amino acid sequence analysis indicated that c116 had been pegylated under the conditions employed (FIG. 6).

EXAMPLE V

Preparation of IL-1ra Muteins

Mutagenesis was performed on single stranded DNA from the IL-1ra gene cloned into the bacteriophage M13. Bio-Rad's Mutagene kit was used which uses the procedure described by Kunkel et al. *Methods in Enzymology* vol. 154, pp. 367–382 (1987). Briefly, single stranded DNA template was generated using an *E. coli* strain that contains the dut and ung mutations, resulting in template that contains uracil instead of thymidine. Mutagenic oligonucleotides between 20 and 30 base pairs in length were annealed to the template and the second strand was resynthesized using DNA polymerase and DNA ligase. The reaction mixtures were used to transform a wild type *E. coli* strain in which the uracil containing strand is degraded by the DNA repair mechanisms and the mutant strand is allowed to replicate. The mutant phage were screened and sequenced by standard techniques. The fragment containing the mutant gene was then subcloned into the expression vector pT5T (Eisenberg et al. *Nature* vol. 343, pp. 341–346, (1989)) and transformed into the T7 expression system strain (*E. coli* B121DE3). Other *E. coli* expression systems may also be used.

Expression clones were grown in Luria Broth supplemented with 15 ug/ml tetracycline at 37° C. When the cultures reached an optical density of 0.8 at 600 nm they were moved to 30° and IPTG was added to a final concentration of 1 mM to induce expression of the IL-1ra gene. Total accumulation of the IL-1ra protein was maximal after 4–6 hours and did not change significantly for up to 12 hours post induction.

EXAMPLE VI

Purification of the IL-1ra Muteins

Cell cultures induced as described above were harvested by centrifugation at 10000 g for 10 min. The cells were resuspended in 30 mM sodium acetate buffer pH 5.2 in 20–50 mls. Lysis was achieved by two passes through the French Pressure cell at 18000 psi. The cell lysate was centrifuged at 10000 g for 10 minutes. The soluble portion was loaded onto a S-Sepharose column and washed with the same buffer containing 75mM NaCl. The IL-1ra mutein eluted with buffer containing 200 mM NaCl. The single pass over the ion exchange resin resulted in a product of sufficient purity (>95%) for pegylation studies. Further purification can be achieved using other ion exchange resins such as Q-Sepharose or MonoQ. This procedure was used for several of the IL-1ra muteins with equal success. In some cases it was necessary to vary the pH and/or NaCl concentrations slightly to purify muteins which have a small change in protein charge due the change in amino acid sequence. With these slight variations that would be easily manipulated by one of ordinary skill in the art, this procedure is generally applicable to all of the muteins studied.

EXAMPLE VII

IL-1ra Mutein Pegylation

In addition to the native IL-1ra, muteins c84s116, c84c116, c0s116 and c9s116 were pegylated. Employing the same conditions used for the native IL-1ra, the pegylated forms of c84s116 and c84c116 were produced and purified. Since c84c116 contains two reactive cysteines, pegylation results in a higher molecular weight protein at about 40 kd on SDS-PAGE. This protein can be purified by cation exchange or size exclusion chromatography and runs at the expected molecular weight of about 68 kd on the latter when using PEG$_{5000}$.

EXAMPLE VIII

Efficacy of the mPEG*IL-1ra

The efficacy of the pegylated native IL-1ra molecules was tested by a standard competitive receptor binding assay using $S^{35}$-IL-1ra as the ligand. Mouse cells (EL4) containing the mouse type 1 IL-1 receptor or hamster cells (CHO) expressing from a cloned gene the human type 1 receptor were used at 1×10 cells per well and 1×10$^5$ cells per well, respectively, in 96 well microliter dishes. $S^{35}$-IL-1ra with a specific activity of 4000 Ci/mmol was added to a final concentration of 150 pM. Cold ligand was added in serial dilutions from 28 mM to 13 pM and allowed to incubate for 4 hours at 4° C. The cells were then filtered through a Milliliter filter plate (Millipore, 0.5 micron pore size Durapore filter), washed to remove nonspecifically bound counts, the filter removed and counted on an Ambis Radio-analytical Imaging System. Equilibrium dissociation constants (kDs) were calculated and used to compare the pegylated and unmodified forms of IL-1ra. Unmodified wild type IL-1ra and c84s116 have equal kD's for the type 1 mouse receptor of 150–300 pM in our assay. The kD for the IL-1ra pegylated form is about 400–800 pM and for pegylated c84s116, 500–1000 pM which is 2.5 and 3.5 fold higher than that of the unmodified protein respectively. The kDs for all but one (c6s116) of the unpegylated muteins are within 65–150% of the native protein, within the standard error of the assay. See Table 1.

TABLE 1

ANALYSIS OF PEGYLATED IL-1ra MOLECULES

| | SIZE (kd) | RECEPTOR ASSAY |
|---|---|---|
| MUTEIN | | |
| WILD TYPE | 17.5 | 100 |
| C84S116 | 17.5 | 98 |
| C9S116 | 17.5 | 67 |
| C6S116 | 17.5 | 37 |
| C0S116 | 17.5 | 63 |
| C84C116 | 17.5 | 95 |
| PEG*IL-1ra | | |
| SINGLE | | |
| PEG$_{5000}$c116 | 50–60 | 34 |
| PEG$_{5000}$c84s116 | 50–60 | 28 |
| PEG$_{8500}$c116 | 70–80 | 30 |
| PEG$_{8500}$c84s116 | 70–80 | 30 |
| PEG$_{8500}$c0s116 | ND | 22 |
| PEG$_{8500}$c9s116 | ND | 12 |
| PEG$_{12000}$c116 | 78 | 20 |
| DOUBLE | | |
| PEG$_{5000}$c84c116 | 70–80 | 11 |
| PEG$_{8500}$c84C116 | 150–200 | 4 |
| PEG$_{12000}$c84c116 | 175 | 5 |
| DUMBBELLS | | |
| PEG$_{3500}$c116 | 55–65 | 49 |
| PEG$_{3500}$c84 | 60 | 49 |
| PEG$_{10,000}$c116 | 175–200 | 49 |
| PEG$_{10,000}$c84 | 200 | 60 |
| PEG$_{20,000}$c84 | >200 | 24 |

Data are presented as a percent of the activity exhibited by unmodified I1-1ra. Standard deviations are within 10%.

EXAMPLE IX

Pharmacokinetics of Pegylated Native Mutein IL-1ra

The pharmacokinetic character of several pegylated native and mutein IL-1ra molecules was tested following intravenous injection of the molecules to rats. Native or pegylated IL-1ra was injected as an intravenous bolus dose (3 mg/kg). Serial blood samples were drawn from the tail vein and assayed for native or pegylated IL-1ra by enzyme-linked immunosorbent assay (ELISA). The resulting plasma IL-1ra concentration vs. time profiles (FIG. 8) illustrate that pegylation has a pronounced influence on the disappearance of IL-1ra from the plasma after intravenous injection. The declines in plasma IL-1ra and pegylated derivatives of IL-1ra are best described by three exponential components. The data indicate that pegylation prolongs the half-lives of these exponential components up to six-fold in the rat (Table 2). The half-lives of these exponential components increase as the size of the PEG molecule increases (Table 2). Additionally, there is evidence that the prolongation of the half-lives may be pegylation site-specific. Standard compartmental analysis was used to interpret the data of FIG. 8. The prolongation of half-lives may be explained based on accepted pharmacokinetic theory which states that the plasma half-life for a drug is inversely related to the plasma clearance for the drug and directly related to the apparent volume of distribution for the drug. Pharmacokinetic analysis of the disappearance of pegylated IL-1ras from the plasma indicate that the prolongation in half-life is inversely related to a decreased plasma clearance for the pegylated molecules, compared to native IL-1ra (Table 2). The decrease in plasma clearance is consistent with an anticipated size-related decrease in glomerular filtration of the pegylated molecules by the kidneys. Also, the prolongation of the half-lives by pegylation is directly related to an increase of the distribution (Vd steady-state, Table 2) of the pegylated molecule. The increase in distribution volume indicates greater penetration of the pegylated molecules into the extravascular pool. Through this mechanism pegylation improves therapy with IL-1ra by increasing the extent to which the active molecules move from the systemic circulation into the extravascular compartment, a compartment in which IL-1 receptors are expected to be located. Because of the similarity between rats and humans in both clearance and distribution mechanisms for IL-1ra, it is apparent that pegylation will similarly improve the pharmacokinetic properties of IL-1ra in humans.

1. Additional Intravenous Pharmacokinetics for Pegylated IL-1ra

The intravenous pharmacokinetics for eight additional pegylated IL-1ra muteins have been characterized using methods previously described. A plot containing intravenous plasma IL-1ra concentration vs. time curves for each of the molecules is attached (FIG. 10). Review of all of the intravenous pharmacokinetic data (Table 3) indicates that as the size of the PEG (single or double) is increased, the plasma clearance decreases and hence the intravenous mean residence time and plasma IL-1ra disappearance half-lives increase. The site of pegylation is important in determining the extent to which the pegylation decreases the plasma clearance and prolongs the means residence time. The addition of two PEGs to IL-1ra prolongs the intravenous mean residence time fourteen-fold compared to wild type IL-1ra.

2. Subcutaneous Pharmacokinetics for Pegylated IL-1ra

Absorption pharmacokinetics of pegylated IL-1ra muteins have been characterized following subcutaneous injection of the molecules to rats. Serial blood samples were drawn from the tail vein and assayed for native or pegylated IL-1ra by enzyme-linked immunosorbent assay (ELISA). The resulting subcutaneous plasma IL-1ra concentration vs. time curves are plotted in FIG. 11. The subcutaneous pharmacokinetic data (Table 3) reveal variable systemic availability for the pegylated muteins, related to the site and size of the PEG, and related to subcutaneous injection in non-optimized formulations. Table 3 also reveals a remarkable positive influence of pegylation on the mean residence time for subcutaneously injected IL-1ra. As the size of the PEG is increased, the mean residence time is generally increased. This increase is probably the result of molecule-size-related slower absorption through the lymphatic circulation (longer mean absorption times) as well as to delayed clearance after the pegylated molecule reaches the systemic circulation (plasma). This prolongation is profound and will improve the pharmacokinetic character of subcutaneous IL-1ra in humans.

TABLE 2

|  | wild type | PEG(8500) | C116 PEG(5000) | C84 PEG(8500) S116 | C84 PEG(5000) S116 |
|---|---|---|---|---|---|
| n | 4 | 1 | 1 | 1 | 1 |
| Vd initial, ml/kg | 24 | 59 | 38 | 58 | 66 |
| Vd steady state, ml/kg | 110 | 160 | 150 | 240 | 290 |
| plasma clearance, ml/min/kg | 7.4 | 3.1 | 7.7 | 3.0 | 5.0 |
| t½ initial phase, min | 1.7 | 12 | 2.5 | 10 | 6.5 |
| t½ intermediate phase, min | 30 | 60 | 29 | 87 | 82 |
| t½ terminal phase, hr | 2.0 | 12 | 1.9 | 7.2 | 5.0 |
| mean residence time, hr | 0.25 | 0.86 | 0.32 | 1.4 | 0.96 |

EXAMPLE X

Preparation of 30 kDa TNF Inhibitor Muteins

Cysteine has been substituted for the native residue at both the amino terminus and carboxyl terminus of the protein as well as all three glycosylation sites (residues 1, 14, 105, 111 and 161 as seen in FIG. 2). Mutagenesis was performed on single stranded DNA from the 30 kDa TNF inhibitor gene cloned into the bacteriophage M13. This gene is described in detail in U.S. patent application Ser. No. 07/555,274 filed Jul. 19, 1990. Mutagenesis was done as described by Kunkel et al. (1987) (see Example V). The mutagenized gene was isolated and subcloned into the expression vector pT5T (Eisenberg et al., *Nature* vol. 343, pg. 341 (1989)) and transformed into the T7 expression system strain *E. coli* BL21DE3. The 30 kDa TNF inhibitor nuteins were purified and refolded as described for native 30 kDa TNF-inhibitor. See, the U.S. patent application Ser. No. 07/555,274 filed Jul. 19, 1990. Refolding includes the addition of cysteine to the solution containing the purified protein. The cysteine aids in the refolding and "bonds to" the free cysteine in the mutein.

EXAMPLE XI

Pegylation of 30 kDa TNF Inhibitor Muteins

The c105 30 kDa TNF Inhibitor mutein was exposed to a 6-fold molar excess of DTT in 50 mM HEPES Ph 7.0 for 30 minutes at ambient temperature in order to remove an extra cysteine attached during the refolding process. The protein was then dialyzed against de-gassed 50 mM HEPES pH 7.0 for 2 hours to remove the DTT. The c105 30 kDa TNF inhibitor was then reacted with a 5 fold molar excess of pegylating reagent 1 (See Example 1A) for 2 hours at ambient temperature in 50 mM HEPES pH 7.0. Approximately 60% of the mutein was converted to the pegylated form.

The c105 pegylation reaction mixture was loaded onto a superdex-75 FPLC column (Pharmacia) run at 0.25 ml/min in 50 mM Tris pH 7.0, 100 mM NaCl. Fractions containing c105-PEG 30 kDa TNF-inhibitor were pooled and loaded on a TSK-2000SW HPLC column (Bio-Rad) run at 0.2 ml/min in the same buffer. The fractions containing essentially pure c105-PEG 30 kDa TNF-inhibitor, as determined by silver stained SDS-PAGE, were pooled and the protein concentration determined by Bio-Rad protein assay. See FIG. 9.

The activity was determined using the murine L929 cell TNF cytoxicity assay as described in U.S. patent application Ser. No. 07/555,274 filed Jul. 19, 1990.

EXAMPLE XII

The Preparation of Bis-Maleimido Peg

The synthesis of the α-(2-aminoethyl) ω-aminopoly (oxyethylene) derivative of the PEG (hereinafter bisamino PEG) consisted of three steps: 1) sulfonation of the hydroxyl group using tresyl chloride as described by Nilson and Mosback (Nilson et al., *Methods in Enzyymology* vol. 104, pg. 56, Academic Press, Inc., N.Y., N.Y. (1984)), 2) substitution of the tresylated intermediate by phthalimide (Pillai et al., *J. Org. Chem.* vol. 45, pg. 5364 (1980)), and 3) reduction of the phthalimide intermediate to amine by hydrazine hydrate (Pillai, supra.). Structures of the starting material, intermediates, and products are shown in Appendix 1 to this Example. Optimum conditions permitted a conversion of approximately 80% of the hydroxyl to amine as determined by 2,4,6-trinitrobenzene sulfonic acid (TNBSA) assay. The bisamino PEG can be purified from the reaction mixture by ion-exchange chromatography. This is a key step for removing reactive byproducts which can interfere with dimer formation.

The bisamino PEG was acylated using maleic anhydride (Butler et al., *Methods in Enzymology* vol. 25, pg. 191, Academic Press, Inc., N.Y., N.Y. (1972)) and the resulting intermediate was cyclized to produce α-(2-maleimidoethyl-ω-maleimidopoly(oxyethylene) (Winsch et al., *Biol. Chem. Hoppe-Seyler* vol. 336, pg. 53 (1985)). This derivative reacts with sulfhydryls via a Michael addition to form a stable thioether.

APPENDIX TO EXAMPLE XII

Starting Material

Generalized formula for polyethylene glycol $PEG_x$

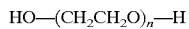

where x denotes the average molecular weight of the polymer in kilodaltons and n is the average number of repeating oxyethylene groups.

Intermediate 1

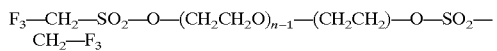

Intermediate 2

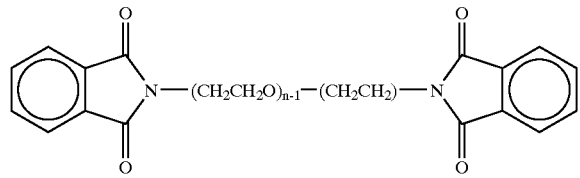

Intermediate 3

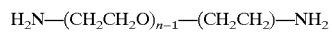

Intermediate 4

$$HOOC-CH=CH-\overset{O}{\underset{\|}{C}}-NH-(CH_2CH_2O)_{n-1}-(CH_2CH_2)-NH-\overset{O}{\underset{\|}{C}}-CH=CH-COOH$$

O-(2-maleimidoethyl)-O$^1$-methyl-polyethylene glycol

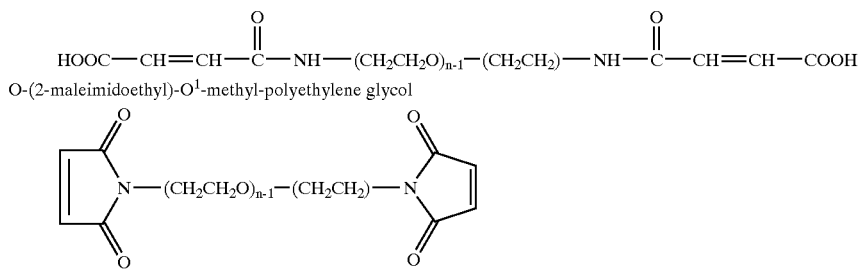

EXAMPLE XIII

In Vivo Results for c105 30 kDa TNF Inhibitor Peg Complexes

The inhibitory effects of four species of pegylated c105 30 kDa TNF inhibitor species were tested in vivo on two different TNF-stimulated physiological actions. One endpoint was the appearance of IL-6 in the plasma of nice that were injected intravenously with human recombinant TNF. The second endpoint was an increase in the migration of neutrophils into the peritoneal cavity after the intraperitoneal administration of human recombinant TNF.

Experiment One. The intravenous administration of c105 30 kDa TNF inhibitor (PEG$_{2,000}$, PEG$_{3,500}$, PEG$_{10,000}$) simultaneously with human recombinant TNF inhibits the induction of IL-6 in the plasma of mice.

BALB/c female mice weighing 20 to 23 g were used to measure the induction of plasma IL-6 levels by human recombinant TNF. In a preliminary experiment, the time course was plotted for the appearance IL-6 in the plasma after the intravenous administration via the tail vein of two doses of human recombinant TNF (FIG. 12). Peak IL-6 levels occurred at two hours after stimulation with either 10 or 20 ug of human recombinant TNF per mouse. The lower dose was used in subsequent experiments.

The potency of c105 30 kDa TNF inhibitor PEG$_{2000}$ dumbbell with that of the unpegylated c105 30 kDa TNF inhibitor was compared. Human recombinant TNF was injected intravenously at a dose of 10 ug per mouse either alone or simultaneously with the TNF inhibitors. Four different reactions of inhibitors to TNF were tested (FIGS. 13A and 13B). The ratios were calculated based on protein content. Three mice were tested at each dose. Blood was collected at two hours after the intravenous injections. IL-6 levels were measure by ELISA.

Both the c105 30 kDa TNF inhibitor and c105 30 kDa TNF inhibitor PEG$_{2000}$ dumbbell caused nearly complete inhibition of IL-6 levels when administered at 10:1 and 5:1 ratios of inhibitor to TNF. At ratios of 1:1, the c105 30 kDa TNF inhibitor PEG$_{2000}$ dumbbell caused 95% reduction of IL-6 levels stimulated by TNF alone, whereas the unpegylated c105 30 kDa TNF inhibitor reduced IL-6 by only about 70%. The results of this experiment indicate that in the ratios tested, both the c105 30 kDa TNF inhibitor and c105 30 kDa TNF inhibitor PEG$_{2000}$ dumbbell were good inhibitors of this TNF-stimulated physiological parameter. At a ratio of 1:1, the c105 30 kDa TNF inhibitor PEG$_{2000}$ dumbbell caused a greater percentage inhibition than the unpegylated inhibitor.

Two other species of pegylated c105 30 kDa TNF inhibitor were tested. The inhibitory effects of c105 30 kDa TNF inhibitor PEG$_{3,500}$ dumbbell and c105 30 kDa TNF inhibitor PEG$_{10,000}$ dumbbell were tested on plasma IL-6 induction. The inhibitors were administered by intravenous injection simultaneously with human recombinant TNF at ratios of 1:1 (c105 30 kDa TNF inhibitor dumbbell: TNF) (FIG. 14). Three mice were tested in each of the two inhibitor-treated groups. Ten mice were injected with TNF alone. When administered in ratios or 1:1, no detectable IL-6 was measured in plasma of mice injected with either c105 30 kDa TNF inhibitor PEG$_{3,500}$ dumbbell or c105 30 kDa TNF inhibitor PEG$_{10,000}$ dumbbell, whereas a significant IL-6 response was elicited in the mice injected with human recombinant TNF alone.

The results of the two experiments show that c105 30 kDa TNF inhibitor PEG$_{2,000}$, PEG$_{3,500}$, and PEG$_{10,000}$ dumbbells are good inhibitors of the induction of plasma IL-6 by human recombinant TNF when administered in a low ratio (1:1) relative to the stimulus.

Experiment Two. The subcutaneous administration of c105 30kDa TNF inhibitor (PEG$_{3,500}$, PEG$_{10,000}$ and PEG$_{20,000}$) simultaneously with the intraperitoneal injection of human recombinant TNF inhibits the migration of neutrophils into the peritoneal cavity.

BALB/c female mice weighing 20 to 23 g were used to measure the migration of neutrophils into the peritoneal cavity after stimulation with human recombinant TNF. The technique used is that of Kim McIntyre et al. (*J. Exp. Med.* vol. 173, pg. 931 (1991)) and is described in brief herein. Mice are injected with TNF in a volume of 0.1 ml directly into the peritoneal cavity. Four hours later the mice are killed and an immediate post mortem lavage of the peritoneal cavity is performed. Four ml of Hank's Balanced Salt Solution (HBS) (calcium and magnesium free) is injected into the peritoneal cavity. The abdomen is gently massaged. The peritoneal fluid is recovered by aspiration with needle and syringe. The total number of peritoneal cells is counted on a Coulter counter. An aliquot of the cellular suspension is dried on a slide and stained with Diff-Kwik stain. A differential count of the cells is made by direct microscopic examination. One hundred cells are examined and classified as either neutrophils, lymphocytes, or macrophages.

In a preliminary experiment, the compared cellular makeup of the lavage fluid after intraperitoneal administration of either pyrogen-free saline or 7.5 ng human recombinant TNF was compared. TNF caused an increase in the percentage of neutrophils and in the absolute number of neutrophils present in the peritoneal lavage fluid. In saline-treated mice, $9.4 \times 10^4$ neutrophils were recovered in the lavage fluid and made up only 2.3% of the total peritoneal cells. In TNF (7.5 ng)-treated mice, the total number of neutrophils was increased to $12.9 \times 10^5$ and the percentage of neutrophils was increased to 19.7%.

The potency of unpegylated c105 30 kDa TNF inhibitor with three pegylated species of c105 30 kDA TNF inhibitor ($PEG_{3,500}$, $PEG_{10,000}$ and $PEG_{20,000}$ dumbbells) was also compared. Keeping the TNF stimulus constant at 7.5 ng per mouse, the inhibitors were tested at ratios of 100:1, 10:1, and 1:1 (c105 30 kDa TNF inhibitor species: TNF). The ratios were calculated based on protein content. The mice were injected subcutaneously with the c105 30 kDa TNF inhibitor simultaneous to the intraperitoneal administration of TNF. Six mice were tested in each dose group. Four hours later the peritoneal lavage fluid was collected and analyzed. Values shown in FIGS. 15A, 15B, 15C, and 15D are the percentage neutrophils in the peritoneal lavage fluid. The lowest ratio at which the unpegylated c105 30 kDa TNF inhibitor and c105 30 kDa TNF inhibitor $PEG_{3,500}$ dumbbell significantly inhibited neutrophil migration is 100:1. The c105 30 kDa TNF inhibitor $PEG_{10,000}$ and $PEG_{20,000}$ dumbbells significantly inhibited neutrophil migration at a ratio 10:1.

The results of this experiment show that c105 30 kDa TNF inhibitor $PEG_{3,500}$, $PEG_{10,000}$ and $PEG_{20,000}$ dumbbells are good inhibitors of the TNF-stimulated neutrophilic migration into the peritoneal cavity. The c105 30 kDa TNF inhibitors $PEG_{10,000}$ and $PEG_{20,000}$ dumbbells were more potent than the unpegylated c105 30 kDa TNF inhibitor and the c105 30 kDa TNF inhibitor $PEG_{3,500}$.

EXAMPLE XIV

PREPARATION AND BIOACTIVITY OF c105 30 kDa TNF INHIBITOR PEG DB

Synthesis

Recombinant c105 30 kDa TNF inhibitor 2–3 mg/ml is treated with a 4-fold molar excess of DTT for 2 hrs at ambient temperature. The TNF inhibitor is then dialyzed against de-gassed 50 mM HEPES, pH 7.0, for 3 hrs at 4° C. To create the PEG-linked dumbbell, the TNF inhibitor is reacted with different molar ratios of the bis-maleimido PEG in 50 mM HEPES pH 7.0. TNF inhibitor is reacted with an equimolar ratio of bis-maleimido PEG. The reactions are incubated for 3–12 hrs at ambient temperature. After incubation, the PEG-linked TNF inhibitor dumbbell is purified from un-PEGylated and singly-PEGylated TNF inhibitor using MONO-S FPLC in 50 mM HOAc, pH 4.0, using a 260 mM, 310 mM and 350 mM NaCl step-gradient. The PEG-linked TNF inhibitor dumbbell elutes at the 310 mM NaCl step. Any remaining unPEGylated TNF inhibitor is removed by chromatography on Superdex75.

Stepwise Reagent Addition:

After DTT treatment and dialysis into 50 mM HEPES pH 7.0, an equimolar amount of bis-maleimido PEG is added, after 1.5 hrs incubation another equimolar amount of bis-maleimide PEG is added. This is incubated for 1.5 hours. This leads to an optimized level of PEG-linked dumbbell formation. Then a 2-fold excess of PEG reagent is added, giving a final PEG-TNF inhibitor ratio of 4:1. This is incubated for 2 hrs and the mixture is dialyzed into 50 mM acetate pH 4.0 for Mono-S chromatography. This yields a mixture which is primarily PEG-linked dimer and singly PEGylated TNF inhibitor. This allow for more efficient purification of PEG-linked dumbbell as there is a greater separation between singly PEGylated TNF inhibitor and dumbbell than dumbbell and unPEGylated TNF inhibitor.

This procedure optimized dumbbell formation, and allowed for more efficient purification.

Step Reaction:

After DTT treatment and dialysis into 50 mM HEPES pH 7.0 an 8-fold molar excess of bis-maleimido PEG is added. This is incubated for 2 hrs at ambient temperature. This converts essentially all the TNF inhibitor to singly-PEGylated form. The singly-PEGylated TNF inhibitor is separated from PEG reagent and any remaining unreacted TNF inhibitor using MONO-S HPLC in 50 mM acetate pH 4.0 with a NaCl gradient. The singly-PEGylated material is diafiltered into 50 mM REPES, pH 7.0, and concentrated to 2–4 mg/ml. DTT treated TNF inhibitor is then added to allow formation of PEG-linked dumbbell. After 2 hrs, the PEG-linked dumbbell is purified using Mono-S HPLC. This method may be used to form a PEG-linked heterodumbbell by adding a second, distinct protein compound.

This procedure optimizes dumbbell formation and can be used for the formation of heterodumbbell compounds. However, this procedure is somewhat labor and time intensive.

Bioactivity of PEG-linked TNF Inhibitor Dumbbells

The ability of c105 30 kDa TNF inhibitor dumbbells to inhibit the cytotoxicity of TNFα in the murine L929 cell cytotoxicity assay was measured. This has allowed for the determination of an $ED_{50}$ for these molecules. They are as follows:

| | |
|---|---|
| Wild Type rTNF inhibitor | 220 ng/ml |
| BMH-linked dumbbells | 220 ng/ml |
| 1900 MW PEG-dumbbells | 4.1 ng/ml |
| 3500 MW PEG-dumbbells | 4.8 ng/ml |
| 10,000 MW PEG-dumbbells | 4.6 ng/ml |
| 20,000 MW PEG-dumbbells | 4.2 ng/ml |

The TNF inhibitor dumbbells also have greatly increased activity in inhibiting the cytotoxicity of TNFβ in the L929 bio-assay. The $ED_{50}$ values against TNFβ are as follows:

| | |
|---|---|
| Wild Type rTNF inhibitor | 70 µg/ml |
| 3400 MW PEG-dumbbells | 80 ng/ml |
| 20,000 MW PEG-dumbbells | 22 ng/ml |

EXAMPLE XV

PHARMACOKINETICS OF PEGYLATED 30 kDa TNF INHIBITOR

1. Intravenous Pharmacokinetics for Peavlated 30 kDa TNF Inhibitor

The pharmacokinetic character of several pegylated 30 kDa TNF inhibitor molecules was determined following intravenous administration of the molecules to rats. Native or pegylated TNF inhibitor was injected as an intravenous bolus dose. Serial blood samples were drawn from the tail vein and assayed for non-pegylated or pegylated TNF inhibitor by enzyme-linked immunosorbent assay (ELISA). The resulting intravenous plasma TNF inhibitor concentration vs. time profiles (FIG. 16) illustrate that pegylation has a pronounced influence on the disappearance of TNF inhibitor from the plasma after intravenous injection. Statistical moment theory (area under the curve [AUC] and area under the first moment curve [AUMC]) was used to interpret the data of FIG. 16. The data indicate that pegylation prolongs the intravenous mean residence time of TNF inhibitor up to fifty-fold in the rat (Table 4). The intravenous mean residence time increases as the size of the attached PEG molecule increases (Table 4). Although not limited by theory, the prolongation of mean residence times may be explained based on conventional pharmacokinetic theory which states that the intravenous mean residence time for a drug is inversely related to the plasma clearance for the drug and directly related to the apparent volume of distribution for the drug. Pharmacokinetic analysis of the disappearance of pegylated TNF inhibitor's from the plasma indicates that the prolongation of half-lives is inversely related to a decreased plasma clearance for the pegylated molecules, compared to non-pegylated TNF inhibitor (Table 4). The decrease in plasma clearance is consistent with an anticipated size-related decrease in glomerular filtration of the pegylated molecules by the kidneys. Because of the probable qualitative similarity between rats and humans in plasma clearance mechanisms for TNF inhibitor, it is apparent that pegylation will similarly improve the pharmacokinetic properties of TNF inhibitor in humans.

2. Subcutaneous Pharmacokinetics for Pegylated 30 kDa TNF Inhibitor

Absorption pharmacokinetics of pegylated TNF inhibitor have been characterized following subcutaneous injection of the molecules to rats. Serial blood samples were drawn from the tail vein and assayed for non-pegylated or pegylated TNF inhibitor concentration vs. time curves and are plotted in FIG. 17. The subcutaneous pharmacokinetic data (Table 4) reveal variable systemic availability for the pegylated molecules, related to the size of the PEG, and related to subcutaneous injection in non-optimized formulations. Table 4 also reveals a positive influence of pegylation on the mean residence time for subcutaneously injected TNF inhibitor. As the size of the PEG is increased, the mean residence time is generally increased. While not limited by theory, this increase is likely the result of size-related slower absorption through the lymphatic circulation (longer mean absorption times) as well as delayed clearance once the pegylated molecule reaches the plasma. This prolongation is profound and will improve the pharmacokinetic character of subcutaneous TNF inhibitor in humans.

EXAMPLE XVI

Solubility of Pegylated Proteins

IL-1ra

Results of a solubility study are shown in FIG. 18. Solubility curves are shown for three different preparations of IL-1ra, and c84 IL-1ra $PEG_{8500}$. The experiments were preformed at 37° C. in a microliter plate with all proteins at 160 mg/ml. The plate was sealed with a cover and then read in a plate reader at 405 nm at various time points. An increase in absorbance is an indication of protein precipitation. There is clearly a decrease in the amount of protein falling out of solution for the PEGylated-sample relative to native IL-1ra.

30 kDa TNF inhibitor

Native 30 kDa TNF inhibitor cannot be concentrated to more than 5 mg/ml. Following PEGylation, the solubility was increased at least 5 fold.

EXAMPLE XVII

Preparation of IL-2 Inhibitor Heterodumbbell

A PEG-linked heterodumbbell may be formed by first pegylating IL-2rα in the presence of an excess of bis-maleimido PEG. The singly pegylated IL-2rα may be purified and IL-2rβ added to react with the remaining reactive maleimide group to form the heterodimer.

Potential sites for PEGylation of Il-2rα include both the amino and carboxyl terminal residues, the two N-linked glycosylation sites, as well as the native free cysteine residue in the molecule. Cysteine residue 192 in the soluble extracellular domain of IL-2rα has been identified as being uninvolved in disulfide bonding. (Miedel et al. *BBRC*, vol. 154, pg. 372 (1988)). This cysteine residue lies in an epitope of an anti-IL-2rα monoclonal antibody that does not affect IL-2 binding to IL-2rα (Lorenzo et al. *J. Immunology*, vol. 147, pg. 2970 (1991)). This indicates this residue is a likely candidate for PEGylation without affecting the activity of IL-2rα.

For IL-2rβ, the potential sites include both the amino and carboxyl termini, the 4 N-linked glycosylation sites and a region (a.a. #108–118) that is similar to a region of biological significance in the murine erythropoietin receptor (Yoshimura, Longmore and Lodish, *Nature*, vol. 348, pg. 647 (1990)). Point mutational analysis of other residues in the receptors may also allow for identification of other sites of PEGylation that yield optimal properties in the heterodumbbell molecule.

EXAMPLE XVIII

Preparation of Heterodumbbells which Inhibit the Classical Pathway of Complement System Many proteins which regulate the complement system have been identified and cloned. Some of them are membrane proteins. One of the membrane proteins is called CR1 (complement receptor 1). The soluble form of CR1 has been examined in in vivo models of diseases. The complement inhibitor inhibits post-ischemic myocardial inflammation and necrosis (Weisman et al. *Science*, vol. 149, pg. 145–151, 1990), reversed passive arthus reaction (Yet et al. *J. Immunology*, vol. 146, pg. 250–256 (1991)), and allograft rejection (Pruitt et al. *J. Surgical Research*, vol. 50, pp. 350–355 (1991)).

The soluble CR1 binds to C3b and C4b. It consists of 30 short consensus repeat sequences (SCR). Most of SCR contain one possible glycosylation site and four cysteines. All of the cysteines are likely be to involved in disulfide bonding. SCRs 1–4 are found to be involved in C4b binding. Two separate portions of CR1, SCRs 8–11 and SCRs 15–18, are involved in C3b binding (Klickstein et al. *J. Exp. Med.*, vol. 168, pp. 1699–1717 (1988): Kalli et al. *J. Exp. Med.* vol. 174, pp. 1451–1460 (1991)). According to this invention, it is possible to produce a heterodumbbell which contains the C4b binding domain and the C3b binding domain of CR1.

The SCRs which contain C4b binding and C3b binding domains of CR1 may be cloned using PCR. These SCRs will be SCRs 1 through 5 (C4b binding) and SCRs 8 through 12 (C3b binding). The genes encoding these SCRs may be cloned in *E. coli* expression vector. The *E. coli* expressed-proteins may be refolded and purified. The success of refolding can be analyzed by the capacity to bind polyC3b or polyC4b. In vitro mutagenesis of these genes may be carried out to substitute native amino acid residues to cysteine. These cysteines may then be used to link the PEG molecule. Possible sites for PEGylation will be the glycosylation site or carboxyll terminal residue of SCR 5 and SCR 12. The C4b binding and C3b binding domains which contain an extra cysteine to the carboxyl terminal residue could be constructed and used for linking PEG molecule.

The PEG linked heterodumbbell may be produced by the two step process of Example XIV. Purification may be carried out by ion-exchange chromatography.

EXAMPLE XIX

Synthesis of an IL-1ra Bis(Maleimide)-Platelet Derived Growth Factor Peptide Peg Heterodumbbell The platelet derived growth factor (PDGF) peptide YGR-PRESGKKRKRLKPT is described in Khachigian, L. et al. *J. Biol. Chem.*, vol. 267, pg. 1660–1666 (1991). A terminal C was added to permit coupling to the maleimide.

The heterodumbbell was synthesized in two steps. In the first step, 1.6 nanomoles of IL-1ra suspended in 3 $\mu$l of 0.05 M Hepes buffer, pH 7.5, was mixed with 6.4 nanomoles of bis-maleimido PEG$_{1900}$ dissolved in 11 $\mu$l of the same buffer. This reaction was carried out for 30 min at 20° C. In the second step, 32 nanomoles of the PDGP peptide dissolved in 4 $\mu$l of 0.2 N sodium phosphate buffer, pH 7.0, was added to the products of the first reaction. The reaction was allowed to proceed for 1 hr at 20° C. The reaction was then terminated by the addition of an equal volume of SDS-PAGE sample buffer containing 30 $\mu$moles of 2-mercaptoethanol.

Samples of the products of the first step of the reaction and the products of the complete two-step reaction, as well as appropriate molecular weight markers, were separated by SDS-PAGE on a 15% polyacrylamide gel which was then stained with Coomassie Blue. The two-step reaction gave an additional band consistent with the predicted size of the heterodumbbell. Approximately 33% of the starting IL-1ra was converted to heterodumbbell by the two-step reaction.

The products of the first step of the reaction can be isolated by cation exchange chromatography on the resin S-Sepharose. The heterodimer may be isolated by cation exchange chromatography due to the abundance of basic amino acids in the peptide.

It is to be understood that the application of the teachings of the present invention to a specific expression system or pegylation reagent will be within the capabilities of one having ordinary skill in the art in light of the teachings contained herein. Thus, it will be apparent to those of ordinary skill in the art that various modifications and variations can be made in the process and products of the present invention. It is intended that the present invention covers these modifications and variations provided they come within the scope of the appended claims and their equivalents.

TABLE 3

Pegylated Interleukin-1 Inhibitor Pharmacokinetics* in rats

| type of pegylation = | none [wild type] | single | single | single | single | single | single | double | dumbbell | dumbbell | dumbbell | dumbbell | dumbbell |
|---|---|---|---|---|---|---|---|---|---|---|---|---|---|
| PEG location = | | 9 | 84 | 84 | 116 | 116 | 116 | 84,116 | 84 | 84 | 84 | 116 | 116 |
| PEG size = | | 8500 | 5000 | 8500 | 5000 | 8500 | 12000 | 8500 | **3400 | **10000 | **20000 | 3400 | **10000 |
| intravenous pharmacokinetics | | | | | | | | | | | | | |
| Vd initial, mL/kg = | 24 | 51 | 72 | 90 | 52 | 63 | 61 | 50 | 45 | 48 | 58 | 47 | 40 |
| Vd steady-state, mL/kg = | 110 | 130 | 310 | 290 | 150 | 110 | 130 | 64 | 64 | 68 | 60 | 58 | 44 |
| plasma clearance, mL/min/kg = | 7.4 | 3.3 | 5.2 | 4.2 | 6.8 | 3.6 | 2.8 | 0.30 | 3.6 | 0.96 | 0.37 | 4.9 | 1.4 |
| plasma mean residence time (i.v.), hr = | 0.25 | 0.65 | 1.0 | 1.2 | 0.37 | 0.52 | 0.76 | 3.5 | 0.30 | 1.2 | 2.7 | 0.19 | 0.52 |
| t½ initial phase, min = | 1.7 | 8.8 | 5.3 | 11 | 4.6 | 11 | 13 | | | | | | |
| t½ intermediate phase, min = | 31 | 57 | 38 | 95 | 36 | 36 | 59 | 100 | 7.8 | 6.2 | 110 | 6.4 | 20 |
| t½ terminal phase, hr = | 2.8 | 3.0 | 2.3 | 6.9 | 2.3 | 3.1 | 7.0 | 7.4 | 0.74 | 0.87 | 5.7 | 1.0 | 2.6 |
| subcutaneous pharmacokinetics | | | | | | | | | | | | | |
| systemic availability, % = | 68 | 37 | 74 | 99 | 28 | 30 | 30 | 25 | 20 | 7.9 | 3.3 | 7.6 | 4.7 |
| maximum plasma IL-1ra, ng/ml = | 1300 | 530 | 940 | 2100 | 360 | 540 | 630 | 1700 | 560 | 630 | 210 | 340 | 230 |
| time of maximum plasma IL-1ra, hr = | 0.82 | 1.8 | 2.5 | 4.0 | 1.5 | 1.3 | 1.8 | 12 | 3.0 | 3.1 | 5.4 | 0.75 | 0.51 |
| plasma mean residence time (s.c.), hr = | 2.7 | 8.1 | 6.4 | 7.5 | 6.5 | 8.5 | 9.0 | 21 | 3.7 | 6.0 | 9.7 | 2.0 | 7.3 |
| mean absorption time, hr = | 2.4 | 7.4 | 5.4 | 6.3 | 6.1 | 8.0 | 8.2 | 18 | 3.4 | 4.8 | 7.0 | 1.8 | 6.7 |

*each pharmacokinetic parameter is expressed as the mean for two rats, except for C84-PEG(3400) dumbbell s.c. dose, for which n = 1
**pharmacokinetic information is caled from 1.5 mg/kg to 3 mg/kg dose

TABLE 4

| type of pegylation = | none [wild type] | none C105 0 | single C105 8500 | single C105 20000 | dumbbell C105 3500 | dumbbell C105 10000 | dumbbell C105 20000 |
|---|---|---|---|---|---|---|---|
| PEG location = | | | | | | | |
| PEG size = | | | | | | | |
| intravenous pharmacokinetics | | | | | | | |
| number of animals = | | 2 | 2 | 2 | 2 | 2 | 2 |
| Vd steady-state, mL/kg = | | 230 | 240 | 140 | 340 | 93 | 130 |

TABLE 4-continued

| type of pegylation = | none [wild type] | none C105 0 | single C105 8500 | single C105 20000 | dumbbell C105 3500 | dumbbell C105 10000 | dumbbell C105 20000 |
|---|---|---|---|---|---|---|---|
| PEG location = | | | | | | | |
| PEG size = | | | | | | | |
| plasma clearance, mL/min/kg = | | 11.0 | 1.7 | 0.17 | 0.82 | 0.16 | 0.11 |
| plasma mean residence time (i.v.), hr = | | 0.37 | 2.3 | 14 | 6.8 | 10 | 19 |
| subcutaneous pharmacokinetics | | | | | | | |
| number of animals = | 2 | | 2 | 1 | 1 | 2 | 2 |
| systemic availability, % = | 99* | | 25 | 65 | 29 | 39 | 34 |
| plasma mean residence time (s.c.), hr = | 3.5 | | 7.0 | 20 | 12 | 17 | 30 |
| mean absorption time, hr = | 3.1* | | 4.7 | 6.0 | 5.2 | 7.0 | 11 |

*referenced to C105 intravenous pharmacokinetics

What is claimed is:

1. An isolated nucleic acid molecule comprising a nucleic acid sequence encoding an interleukin-1 inhibitor (IL-1i) polypeptide, having interleukin-1 (IL-1) inhibitory activity, wherein said polypeptide is selected from the group consisting of:

A) a polypeptide comprising all or an IL-1 inhibitory fragment of the amino acid sequence:

(U) (X) P S G R K S S K M Q A F R I W D V N Q K T F Y L R N N Q L V A G Y L Q G P N V N L E E K I D V V P I E P H A L F L G I H G G K M C L S C V K S G D E T R L Q L E A V N I T D L S E N R K Q D K R F A F I R S D S G P T T S F E S A A C P G W F L C T A M E A D Q P V S L T N M P D E G V M V T K F Y F Q E D E wherein (U) is M or nothing and (X) is R or P; and B) a polypeptide that is at least about 70% homologous to the amino acid sequence set forth in A).

2. A nucleic acid molecule of claim 1, wherein the nucleic acid sequence encodes a oolypeptide that is at least 80% homologous to amino acid sequence set forth in claim 1 (A).

3. A nucleic acid molecule of claim 1, wherein the nucleic acid sequence encodes a polypeptide that is at least 95% homologous to amino acid sequence set forth in claim 1 (A).

4. A nucleic acid molecule of claim 1, wherein the nucleic acid sequence encodes a polypeptide wherein (U) is M.

5. An isolated nucleic acid molecule comprising a nucleic acid sequence encoding an interleukin-1 inhibitor (IL-1i) polypeptide, having interleukin-1 (IL-1 inhibitoty activity, wherein said polypeptide is selected from the group consisting of:

A) a polypeptide comprising all or an IL-1 inhibitory fragment of the amino acid sequence:

(U) (X) P S G R K S S K M Q A F R I W D V N Q K T F Y L R N N Q L V A G Y L Q G P N V N L E E K I D V V P I E P H A L F L G I H G G K M C L S C V K S G D E T R L Q L E A V N I T D L S E N R K Q D K R F A F I R S D S G P T T S F E S A A C P G W F L C T A M E A D Q P V S L T N M P D E G V M V T K F Y F Q E D E wherein (U) is M or nothing and (X) is R or P; and B) a polypeptide that is at least about 90% homologous to the amino acid sequence set forth in A).

6. The nucleic acid molecule of claim 5, wherein the amino acid sequence of said polypeptide is at least about 90% homologous to the following amino acid sequence:

(U) (X) P S G R K S S K M Q A F R I W D V N Q K T F Y L R N N Q L V A G Y L Q G P N V N L E E K I D V V I E P H A L F L G I H G G K M C L S C V K S G D E T R L Q L E A V N I T D L S E N R K Q D K R F A F I R S D S G P T T S F E S A A C P G W F L C T A M E A D Q P V S L T N M P D E G V M V T K F Y F Q E D E wherein (U) is M or nothing and (X) is R.

7. The nucleic acid molecule of claim 6, wherein (U) is nothing.

8. The nucleic acid molecule of claim 6, wherein (U) is M.

9. The nucleic acid molecule of claim 5, wherein the amino acid sequence of said polypeptide is at least about 95% homologous to the following amino acid sequence:

(U) (X) P S G R K S S K M Q A F R I W D V N Q K T F Y L R N N Q L V A G Y L Q s P N V N L E E K I D V V P I E P H A L F L G I H G G K M C L S C V K S G D E T R L Q L E A V N I T D L S E N R K Q D K R F A F I R S D S G P T T S F E S A A C P G W F L C T A M E A D Q P V S L T N M P D E G V M V T K F Y F Q E D E wherein (U) is M or nothing and (X) is R.

10. The nucleic acid molecule of claim 5, wherein said polypeptide comprises all or an IL-1 inhibitory fragment of the amino acid sequence:

(U) (X) P S G R K S S K M Q A F R I W D V N Q K T F Y L R N N Q L V A G Y L Q G P N V N L E E K I D V V P I E P H A L F L G I H G G K M C L S C V K S G D E T R L Q L E A V N I T D L S E N R K Q D K R F A F I R S D S G P T T S F E S A A C P G W F L C T A M E A D Q P V S L T N M P D E G V M V T K F Y F Q E D E wherein (U) is M or nothing and (X) is R or P.

11. The nucleic acid molecule of claim 10, wherein (X) is R.

12. The nucleic acid mnolecule of claim 10, wherein said polypeptide comprises the following amino acid sequence:

(U) (X) P S G R K S S K M Q A F R I W D V N Q K T F Y L R N N Q L V A G Y L Q G P N V N L E E K I D V V P I E P H A L F L G I H G G K M C L S C V K S G D E T R L Q L E A V N I T D L S E N R K Q D K R F A F I R S D S G P T T S F E S A A C P G W F L C T A M E A D Q P V S L T N M P D E G V M V T K F Y F Q E D E wherein (U) is M or nothing and (X) is R or P.

13. The nucleic acid molecule of claim 12, wherein (X) is R.

14. The nucleic acid molecule of claim 13, wherein (U) is M.

15. The nucleic acid molecule of claim 13, wherein (U) is nothing.

16. The nucleic acid molecule of claim 13, wherein said polypeptide consists of the following amino acid sequence:

(U) R P S G R K S S K M Q A F R I W D V N Q K T F Y L R N N Q L V A G Y L Q G P N V N L E E K I D V V P I E P H A L F L G I H G G K M C L S C

V K S G D E T R L Q L E A V N I T D L S E N R K
Q D K R F A F I R S D S G P T T S F E S A A C P
G W F L C T A M E A D Q P V S L T N M P D E C
V M V T K F Y Q E D E wherein (U) is M or nothing.

17. The nucleic acid molecule of claim 16, wherein (U) is M.

18. The nucleic acid molecule of claim 13, wherein said nucleic acid sequence encoding said IL-1i polypeptide further comprises a sequence encoding an N-terminal secretion leader sequence.

19. The nucleic acid molecule of claim 18, wherein the leader sequence comprises all or part of the following amino acid sequence:

M E I C R G L R S H L I T L L L F L F H S E T I C.

20. A recombinant host cell containing a DNA molecule comprising a nucleic acid sequence encoding an interleukin-1 inhibitor (IL-1i) polypeptide, said polypeptide being capable of inhibiting IL-1, wherein said polypeptide is selected from the group consisting of A) a polypeptide comprising all or an IL-1 inhibitory fragment of the amino acid sequence:

(U) (X) P S G R K S S K M O A F R I W D V N O K
T F Y L R N N O L V A G Y L O G P N V N L E E
K I D V V P I E P H A L F L G I H G G K M C L S
C V K S G D E T R L O L E A V N I T D L S E N R
K O D K R F A F I R S D S G P T T S F E S A A C
P G W F L C T A M E A D O P V S L T N M P D E
G V M V T K F Y F O E D E wherein (U) is M or nothing and (X) is R or P; and B) a polypeptide that is at least about 70% homologous to the amino acid sequence set forth in A).

21. A recombinant host cell of claim 20, wherein said polypeptide is selected from the group consisting of:

A) a polypeptide comprising all or an IL-1 inhibitory fragment of the amino acid sequence:

(U) (X) P S C R K S S K M Q A P R I W D V N Q K T
F Y L R N N Q L V A G Y L Q G P N V N L E E K
I D V V P I E P H A L F L G I H G G K M C L S C
V K S G D E T R L Q L E A V N I T D L S E N R K
Q D K R F A F I R S D S G P T T S F E S A A C P
G W F L C T A M E A D Q P V S L T N M P D E G
V M V T K F Y F Q E D E wherein (U) is M or nothing and (X) is R or P; and B) a polypeptide that is at least about 90% homologous to the amino acid sequence set forth in A).

22. The recombinant host cell of claim 21, wherein the amino acid sequence of said polypeptide is at least about 95% homologous to the following amino acid sequence:

(U) (X) P S G R K S S K M Q A F R I W D V N Q K
T F Y L R N N Q L V A G Y L Q G P N V N L E E
K I D V V P I E P H A L F L G I H G G K H C L S
C V K S G D E T R L Q L E A V N I T D L S E N R
K Q D K R F A F I R S D S G P T T S F E S A A C
P G W F L C T A M E A D Q P V S L T N M P D E
G V M V T K F Y F Q E D E wherein (U) is M or nothing and (X) is R.

23. The recombinant host cell of claim 21, wherein the amino acid sequence of said polypeptide is at least about 90% homologous to the following amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
K Q D K R F A F I R S D S G P T T S F E S A A C
P G W F L C T A M E A D Q P V S L T N M P D E
G V M V T K F Y F Q E D E wherein (U) is M or nothing and (X) is R.

24. The recombinant host cell of claim 23, wherein said host cell is not capable of glycosylation or is a non-human host cell.

25. The recombinant host cell of claim 24, wherein said host cell is selected from a yeast cell, a mouse Ltk⁻ cell, and a Chinese hamster ovary cell.

26. The recombinant host cell of claim 24, wherein said host cell is a prokaryotic cell.

27. The recombinant host cell of claim 26, wherein said host cell is *E. coil.*

28. The recombinant host cell of claim 24, wherein said host cell is a eukaryotic cell.

29. The recombinant host cell of claim 28, wherein said host cell is a mammallan cell.

30. The recombinant host cell of claim 28, wherein said host cell is a Chinese hamster ovary cell.

31. The recombinant host cell of claim 23, wherein said host cell produces glycosylated IL-1i.

32. The recombinant host call of claim 23, wherein said host cell produces nonglycosylated IL-1i.

33. The recombinant host cell of claim 23, wherein (U) is nothing.

34. The recombinant host cell of claim 23, wherein (U) is M.

35. The recombinant host cell of claim 21, wherein said polypeptide comprises all or an IL-1 inhibitory fragment of the amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
X Q D K H F A F I R S D E G P T T S F E S A A C
P G W F L C T A M E A D Q P V S L T N M P D E
G V M V T K F Y F Q E D E

Wherein (U) is M or nothing and (X) is R or P.

36. The recombinant host call of claim 35, wherein (X) is R.

37. The recombinant host cell of claim 35, wherein said polypeptide comprises the following amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
K Q D K R F A F I R S D S G P T T S F E S A A C
P G W F L C T A M E A D Q P V S L T N M P D E
G V M V T K F Y F Q E D E wherein (U) is M or nothing and (X) is R or P.

38. The recombinant host cell of claim 37, wherein (X) is R.

39. The recombinant host cell of claim 38, wherein (U) is M.

40. The recombinant host cell of claim 38, wherein (U) is nothing.

41. The recombinant host cell of claim 38, wherein said host cell is not capable of glycosylation or is a non-human host cell.

42. The recombinant host cell of claim 41, wherein said host cell is selected from a yeast cell, a mouse Ltk⁻ cell, and a Chinese hamster ovary cell.

43. The recombinant host cell of claim 41, wherein said host cell is a prokaryotic cell.

44. The recombinant host call of claim 43, wherein said host cell is *E. coli.*

45. The recombinant host cell of claim 41, wherein said host cell is a eukaryotic cell.

46. The recombinant host cell of claim 45, wherein said host cell is a mammalian cell.

47. The recombinant host cell of claim 45, wherein said host cell is a Chinese hamster ovary cell.

48. The recombinant host cell of claim 38, wherein said host cell produces glycosylated IL-1i.

49. The recombinant host cell of claim 38, wherein said host cell produces nonglycosylated IL-1 i.

50. The recombinant host cell of claim 38, wherein said DNA molecule comprises a heterologous promoter operatively linked to said nucleic acid sequence encoding said IL-1i polypeptide.

51. The recombinant host cell of claim 38, wherein said nucleic acid sequence encoding said IL-1i polypeptide further comprises a sequence encoding an N-terminal secretion leader sequence.

52. The recombinant host cell of claim 51, wherein the leader sequence comprises all or part of the following amino acid sequence:

M E I C R G L R S H L I T L L L F L F H S E T I C.

53. The recombinant host cell of claim 38, wherein said polypeptide consists of the following amino acid sequence:

(U) R P S G R K S S K M Q A E R I W D V N Q K T
F Y L R N N Q L V A G Y L Q G P N V N L E E K
I D V V P I E P H A L F L G I H G G K M C L S C
V K S G D E T R L Q L E A V N I T D L S E N R K
Q D K R F A F I R S D S G P T T S F E S A A C P
G W F L C T A M E A D Q P V S L T N M P D E G
V M V T K F Y F Q E D E wherein (U) is M or nothing.

54. The recombinant host cell of claim 53, wherein (U) is M.

55. The recombinant host cell of claim 54, wherein said host call produces nonglycosylated IL-1i.

56. The recombinant host cell of claim 55, wherein said host cell is *E. coli*.

57. The recombinant host cell of claim 53, wherein said host cell is a Chinese hamster ovary host cell.

58. The recombinant host cell of claim 53, wherein said host cell is a eukaryotic host cell.

59. The recombinant host cell of claim 53, wherein said host cell produces glycosylated IL-1i.

60. The recombinant host cell of claim 53, wherein said host cell is a mammalian host cell.

61. The recombinant host cell of claim 53, wherein said host cell is a prokaryotic host cell.

62. A process for preparing an interleukin-1 inhibitor (IL-1i) polypeptide, comprising producing the recombinant IL-1i polypeptide in a host cell according to claim 20 under suitable conditions to express the recombinant DNA molecule contained therein to produce the recombinant polypeptide.

63. The process of claim 62, further comprising harvesting the IL-1i polypeptide.

64. A process of claim 63, wherein said recombinant polypeptide is selected from the group consisting of:

A) a potypeptide comprising all or an IL-1 inhibitory fragment of the amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
K Q D K R F A F I R S D S G P T T S F E S A A C
P G W F L C T A M E A D Q P V S L T N M P D E
G V M V T K F Y F Q E D E wherein (U) is M or nothing and (X) is R or P; and B) a polypeptide that is at least about 90% homologous to the amino acid sequence set forth in A).

65. The process of claim 64, wherein the amino acid sequence of said recombinant polypeptide is at least about 95% homologous to the following amino acid sequence:

(U) (X) P S G R K S S K M Q A F R I W D V N Q K
T F Y L R N N Q L V A G Y L Q G P N V N L E E
K I D V V P T E P H A L F L G I H G G K M C L S
C V K S G D E T R L Q L E A V N I T D L S E N R
K Q D K R F A F I R S D S G P T T S F E S A A C
P G W F L C T A M E A D Q P V S L T N M P D E
G V M V T K F Y F Q E D E wherein (U) is M or nothing and (X) is R.

66. The process of claim 64, wherein the amino acid sequence of said recombinant polypeptide is at least about 90% homologous to the following amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
K Q D K R F A F I P S D S G P T T S F E S A A C
P G W F L C T A M E A D Q P V S L T N M P D E
G V M V T K F Y F Q E D E wherein (U) is M or nothing and (X) is R.

67. The process of claim 66, wherein said host cell is not capable of glycosylation or is a non-human host cell.

68. The process of claim 67, wherein said host cell is selected from a yeast cell, a mouse Ltk+ cell, and a Chinese hamster ovary cell.

69. The process of claim 67, wherein said host cell is a prokaryotic cell.

70. The process of claim 69, wherein said host cell is *E. coli*.

71. The process of claim 67, wherein said host cell is a eukaryotic cell.

72. The process of claim 71, wherein said host cell is a mammalian cell.

73. The process of claim 71, wherein said host cell is a Chinese hamster ovary cell.

74. The process of claim 66, wherein said recombinant polypeptide is glycosylated.

75. The process of claim 66, wherein said recombinant polypeptide is nonglycosylated.

76. The process of claim 66, wherein (U) is nothing.

77. The process of claim 66, wherein (U) is M.

78. The process of claim 64, wherein said recombinant polypeptide comprises all or an IL-1 inhibitory fragment of the amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
K Q D K R F A F I R S 0 S G e T T S F E S A A C
P G W F L C T A M E A D Q P V S L T N M P D E
G V M V T K F Y F Q E D E wherein (U) is M or nothing and (X) is R or P.

79. The process of claim 78, wherein (X) is R.

80. The process of claim 79, wherein said recombinant polypeptide inhibits IL-1 induced $PGE_2$ production.

81. The process of claim 78, wherein said recombinant polypeptide comprises the following amino acid sequence:

(U) (X) P S G R K S S K M Q A F R I W D V N Q K
T F Y L R N N Q L V A G Y L Q G P N V N L E E
K I D V V P I E P H A L F L G I H G G K M C L S
C V K S G D E T R L Q L E A V N I T D L S E N R
K Q D K R F A F I R S D S G P T T S F E S A A C
P G W F L C T A M E A D Q P V S L T N M P D E
G V M V T K F Y F Q E D E wherein (U) is M or nothing and (X) is R or P.

82. The process of claim 81, wherein (X) is R.

83. The process of claim 82, wherein (U) is M.

84. The process of claim 82, wherein (U) is nothing.

85. The process of claim 82, wherein said host cell is not capable of glycosylation or is a non-human host cell.

86. The process of claim 85, wherein said host cell is selected from a yeast cell, a mouse Ltk⁻ cell, and a Chinese hamster ovary cell.

87. The process of claim 85, wherein said host cell is a prokaryotic cell.

88. The process of claim 85, wherein said host cell is *E. coli*.

89. The process of claim 85, wherein said host cell is a eukaryotic cell.

90. The process of claim 89, wherein said host cell is a mammalian cell.

91. The process of claim 89, wherein said host cell is a Chinese hamster ovary cell.

92. The process of claim 82, wherein said recombinant polypeptide is glycosylated.

93. The process of claim 82, wherein said recombinant polypeptide is nonglycosylated.

94. The process of claim 82, wherein said DNA molecule comprises a heterologous promoter operatively linked to said nucleic acid sequence encoding said IL-1i polypeptide.

95. The process of claim 82, wherein said nucleic acid sequence encoding said IL-1i polypeptide further comprises a sequence encoding an N-terminal secretion leader sequence.

96. The process of claim 95, wherein the leader sequence comprises all or part of the following amino acid sequence:

M E I C R G L R S H L I T L L L F L F H S E T I C.

97. The process of claim 82, wherein said recombinant polypeptide consists of the following amino acid sequence:

(U) R P S G R K S S K M Q A F R I W D V N Q K T
F Y L R N N Q L V A G Y L Q G P N V N L E E K
I D V V P I E P H A L F L G I H G G K M C L S C
V K S G D E T R L Q L E A V N I T D L S E N R X
Q D K R F A F I R S D S G P T T S F E S A A C P
G W F L C T A M E A D Q P V S L T N M P D E G
V M V T K F Y F Q E D E wherein (U) is M or nothing.

98. The process of claim 97, wherein (U) is M.

99. The process of claim 98, wherein said recombinant polypeptide is nonglycosylated.

100. The process of claim 99, wherein said host cell is *E. coli*.

101. The process of claim 97, wherein said host cell is a Chinese hamster ovary host cell.

102. The process of claim 97, wherein said host cell is a eukaryotic host cell.

103. The process of claim 97, wherein said recombinant polypeptide is glycosylated.

104. The process of claim 97, wherein said host cell is a mammalian host cell.

105. The process of claim 97, wherein said host cell is a prokaryotic host cell.

\* \* \* \* \*